(12) United States Patent
Jovanovich et al.

(10) Patent No.: US 11,926,815 B2
(45) Date of Patent: Mar. 12, 2024

(54) METHOD AND APPARATUS FOR PROCESSING TISSUE SAMPLES

(71) Applicant: S2 Genomics, Inc., Livermore, CA (US)

(72) Inventors: Stevan Bogdan Jovanovich, Livermore, CA (US); Kaiwan Chear, Livermore, CA (US); Bruce Leisz, San Jose, CA (US); David Eberhart, Santa Clara, CA (US); John Bashkin, Fremont, CA (US)

(73) Assignee: S2 GENOMICS, INC., Livermore, CA (US)

( * ) Notice: Subject to any disclaimer, the term of this patent is extended or adjusted under 35 U.S.C. 154(b) by 0 days.

(21) Appl. No.: 18/119,810

(22) Filed: Mar. 9, 2023

(65) Prior Publication Data
US 2023/0407232 A1 Dec. 21, 2023

Related U.S. Application Data

(63) Continuation of application No. 15/734,128, filed as application No. PCT/US2019/035097 on Jun. 1, 2019, now Pat. No. 11,618,876.
(Continued)

(51) Int. Cl.
*C12M 1/33* (2006.01)
*C12M 1/00* (2006.01)
(Continued)

(52) U.S. Cl.
CPC ............ *C12M 45/02* (2013.01); *C12M 41/12* (2013.01); *C12M 45/06* (2013.01); *C12M 45/09* (2013.01);
(Continued)

(58) Field of Classification Search
CPC ...... C12M 45/02; C12M 41/12; C12M 45/06; C12M 45/09; C12M 45/20; C12N 1/066;
(Continued)

(56) References Cited

U.S. PATENT DOCUMENTS

| 4,307,846 A | 12/1981 | Spelsberg |
| 5,114,858 A * | 5/1992 | Williams ............... C12M 47/06 |
| | | 435/270 |

(Continued)

FOREIGN PATENT DOCUMENTS

| EP | 2540394 A1 | 1/2013 |
| EP | 3548603 A1 | 10/2019 |

(Continued)

OTHER PUBLICATIONS

Japan Patent Office, Notice of Reasons for Rejection for JP2021-516862 dated May 24, 2023, 4 pages.
(Continued)

*Primary Examiner* — Michael L Hobbs
*Assistant Examiner* — Lenora A Abel
(74) *Attorney, Agent, or Firm* — Storella, P.C.

(57) ABSTRACT

A system, methods, and apparatus are described to collect and prepare single cells, nuclei, subcellular components, and biomolecules from specimens including tissues and in some embodiments use the single cells to form organoids or microtissues. The system can perform enzymatic and/or physical disruption of the tissue to dissociate it into single-cells and then use a hanging droplet method to form organoids or microtissues.

42 Claims, 11 Drawing Sheets

Related U.S. Application Data

(60) Provisional application No. 62/679,494, filed on Jun. 1, 2018.

(51) Int. Cl.
| | |
|---|---|
| *C12M 1/34* | (2006.01) |
| *C12N 1/06* | (2006.01) |
| *G01N 1/28* | (2006.01) |
| *G01N 1/31* | (2006.01) |
| *G01N 1/40* | (2006.01) |

(52) U.S. Cl.
CPC ............. *C12M 45/20* (2013.01); *C12N 1/066* (2013.01); *G01N 1/286* (2013.01); *G01N 1/31* (2013.01); *G01N 1/4077* (2013.01); *G01N 2001/4088* (2013.01)

(58) Field of Classification Search
CPC ........ G01N 1/286; G01N 1/31; G01N 1/4077; G01N 2001/4088
USPC .......................................................... 435/5
See application file for complete search history.

(56) References Cited

U.S. PATENT DOCUMENTS

| | | | |
|---|---|---|---|
| 5,234,809 A | 8/1993 | Boom et al. | |
| 5,665,554 A | 9/1997 | Reeve et al. | |
| 5,898,071 A | 4/1999 | Hawkins | |
| 5,952,215 A | 9/1999 | Dwulet et al. | |
| 6,190,616 B1 | 2/2001 | Jovanovich et al. | |
| 6,391,541 B1 | 5/2002 | Petersen et al. | |
| 6,534,262 B1 | 3/2003 | McKernan et al. | |
| 6,551,839 B2 | 4/2003 | Jovanovich et al. | |
| 7,244,961 B2 | 7/2007 | Jovanovich et al. | |
| 8,288,106 B2 | 10/2012 | Fekete et al. | |
| 8,536,322 B2 | 9/2013 | Han | |
| 8,815,521 B2 | 8/2014 | Taylor et al. | |
| 8,936,933 B2 | 1/2015 | Chen et al. | |
| 9,347,086 B2 | 5/2016 | Connolly et al. | |
| 2002/0197631 A1 | 12/2002 | Lawrence et al. | |
| 2003/0066915 A1 | 4/2003 | Taylor | |
| 2003/0157523 A1 | 8/2003 | Frantz et al. | |
| 2003/0170617 A1 | 9/2003 | Pasloske | |
| 2004/0086872 A1 | 5/2004 | Childers et al. | |
| 2005/0070941 A1 | 3/2005 | Isogimi | |
| 2005/0070944 A1 | 3/2005 | Holl et al. | |
| 2005/0287670 A1* | 12/2005 | Gulliver ................. C12M 41/22 435/325 |
| 2006/0030796 A1* | 2/2006 | Xu .......................... G01N 1/286 601/2 |
| 2008/0050814 A1 | 2/2008 | Allickson | |
| 2008/0306610 A1 | 12/2008 | Wang et al. | |
| 2008/0307904 A1 | 12/2008 | Pressman et al. | |
| 2011/0206646 A1 | 8/2011 | Alfonso et al. | |
| 2014/0057255 A1 | 2/2014 | Holmes | |
| 2014/0377880 A1 | 12/2014 | Emburgh et al. | |
| 2016/0116439 A1 | 4/2016 | Kindwall et al. | |
| 2017/0106366 A1 | 4/2017 | Gross et al. | |
| 2017/0292151 A1 | 10/2017 | Connolly et al. | |
| 2018/0119218 A1 | 5/2018 | Bashir et al. | |
| 2019/0212233 A1 | 7/2019 | Jovanovich et al. | |
| 2021/0214673 A1 | 7/2021 | Jovanovich et al. | |
| 2022/0082479 A1 | 3/2022 | Jovanovich et al. | |
| 2022/0146382 A1 | 5/2022 | Jovanovich et al. | |

FOREIGN PATENT DOCUMENTS

| | | |
|---|---|---|
| JP | 2011508589 A | 3/2011 |
| JP | 2017181278 A | 10/2017 |
| WO | 0194911 A2 | 12/2001 |
| WO | 2014153072 A1 | 9/2014 |
| WO | 2017041050 A1 | 3/2017 |
| WO | 2017075293 A1 | 5/2017 |
| WO | 2017116694 A1 | 7/2017 |
| WO | 2017123970 A1 | 7/2017 |
| WO | 2018102471 A1 | 6/2018 |
| WO | 2019232504 A2 | 12/2019 |
| WO | 2020077236 A1 | 4/2020 |
| WO | 2021236666 A1 | 11/2021 |

OTHER PUBLICATIONS

European Supplementary European Search Report for Application No. EP19811211.2 dated Jan. 12, 2023, 11 pages.
Extended European Search Report for EP17875198.8, dated Sep. 29, 2020, (Completion Date Jun. 18, 2020), 11 pages.
International Search Report and Written Opinion for PCT/US2017/063811 dated Mar. 29, 2018, 15 pgs.
International Search Report and Written Opinion for PCT/US2019/035097 dated Dec. 6, 2019, 16 pgs.
International Search Report and Written Opinion of PCT/US2020/033001 dated Oct. 29, 2021, 16 pages.
Partial Supplementary European Search Report for EP17875198.8, dated Jun. 25, 2020, (Completion Date Jun. 18, 2022), 14 pages.
Supplementary European Search Report for EP19811211.2 dated Jul. 5, 2022, (Completion Date Mar. 24, 2022) 11 pages.
Supplementary Partial European Search Report for EP19811211 dated Apr. 4, 2022, (Completion Date Mar. 24, 2022), 12 pages.
U.S. Appl. No. 15/734,128, Final Office Action dated Apr. 18, 2022, 30 pages.
U.S. Appl. No. 15/734,128, Notice of Allowability dated Feb. 3, 2023, 6 pages.
U.S. Appl. No. 15/734,128, Notice of Allowance dated Nov. 21, 2022, 11 pages.
U.S. Appl. No. 17/581,940, Final Office Action dated Nov. 7, 2022, 11 pages.
U.S. Appl. No. 17/581,940, Non-Final Office Action dated Apr. 20, 2022, 7 pages.
U.S. Appl. No. 17/581,940, Notice of Allowance dated Mar. 13, 2023, 5 pages.
Chinese 1st Office Action dated Jan. 12, 2024, CN Patent Application No. 201980051401.0; English Translation of Office Action Summary, pp. 1-14.
U.S. Patent Office, U.S. Appl. No. 18/229,141, Non-Final Office Action dated Jan. 29, 2024, 9 pages.

* cited by examiner

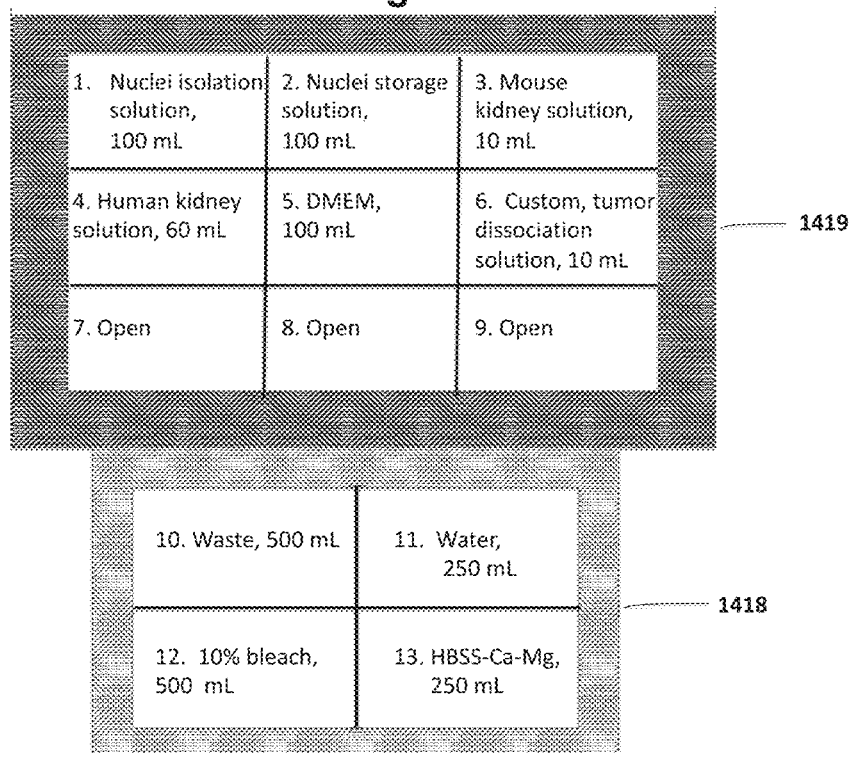
Figure 17.
FIGURE 18A.
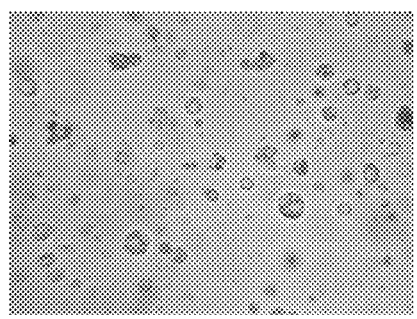
FIGURE 18B.
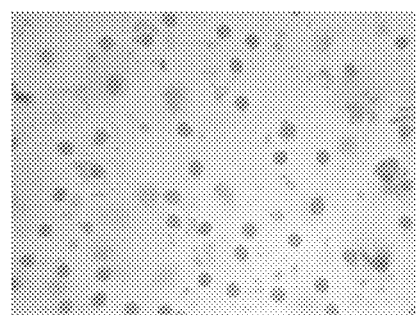

| Stress gene panel. | |
|---|---|
| Gene Name | NCBI Accession # |
| Atf3 | NM_007498.3 |
| Dusp1 | NM_013642.3 |
| EgR1 | NM_007913.5 |
| Hsp90aa1 | NM_010480.5 |
| Hsp90ab1 | NM_008302.3 |
| Junb | NM_008416.3 |
| Jund | NM_010592.5 |
| Jun | NM_010591.2 |
| Nfkbia | NM_010907.2 |
| Ubc | NM_019639.4 |
| Mt1 | NM_013602.3 |
| HMOX1 | NM_010442.2 |
| SLC9A3R2 | NM_023055.2 |
| TXNRD1 | NM_015762.2 |
| TSC22D1 | NM_009366.4 |
| RBM3 | NM_016809.6 |
| BOP1 | NM_013481.1 |
| EIF5A | NM_181582.4 |
| DNM2 | NM_007871.2 |
| CYC1 | NM_025567.3 |
| PSMD12 | NM_025894.2 |
| Actb * | NM_007393 |
| B2m | NM_009735 |
| Gapdh * | NM_008084 |

METHOD AND APPARATUS FOR PROCESSING TISSUE SAMPLES

CROSS REFERENCE TO RELATED APPLICATIONS

This application is a continuation of U.S. patent application Ser. No. 15/734,128, filed Dec. 1, 2020, which is a U.S. 371 national stage entry of PCT/US19/35097 filed Jun. 1, 2019, which claims the benefit of the priority date of U.S. provisional patent application No. 62/679,494, filed Jun. 1, 2018, which applications are incorporated herein by reference.

STATEMENT OF FEDERALLY SPONSORED RESEARCH OR DEVELOPMENT (IF ANY)

This research was supported in part by the National Human Genome Research Institute of the National Institutes of Health under award number RH010129.

THE NAMES OF THE PARTIES TO A JOINT RESEARCH AGREEMENT IF THE CLAIMED INVENTION WAS MADE AS A RESULT OF ACTIVITIES WITHIN THE SCOPE OF A JOINT RESEARCH AGREEMENT

None.

REFERENCE TO A "SEQUENCE LISTING"

None.

BACKGROUND OF THE INVENTION

A) Field of Invention

This invention relates to the field of sample preparation from biological materials. More specifically, the invention relates to the processing of solid tissues into single cells, nuclei, biomolecules, and processed samples for bioanalysis and the use of single cells to form organoids and other microtissues.

B) Description of Related Art

Analysis of single cells and groups of cells is providing information to dissect and understand how cells function individually and unprecedented insight into the range of individual cellular responses aggregated in ensemble measurements. Single cell methods for electrophysiology, flow cytometry, imaging, mass spectrometry (Lanni, E. J., et. al. J Am Soc Mass Spectrom. 2014; 25(11):1897-907.), microarray (Wang L and KA Janes. Nat Protoc. 2013; 8(2):282-301.), and Next Generation Sequencing (NGS) (Saliba A. E., et. al. Nucleic Acids Res. 2014; 42(14):8845-60.) have been developed and are driving an increased understanding of fundamental cellular processes, functions, and interconnected networks. As the individual processes and functions are understood and differentiated from ensemble measurements, the individual information can in turn lead to discovery of how network processes among cells operate. The networks may be in tissues, organs, multicellular organisms, symbionts, biofilms, surfaces, environments, or anywhere cells live and interact.

Model systems of tissues are an important tool in the understanding of tissue function, development, and regulation. Improved model systems are needed to be developed for basic research, companion diagnostics, and screening of compounds to develop therapeutics. Historically, two dimensional culture of model cell lines have been used to gain knowledge and model tissue function, typically with only one cell type at a time. However, solid tissues are three dimensional (3D) structures with complex interactions between multiple cell types. The two dimensional model can lack cell to cell interactions and the impacts of the extracellular matrix on the cells.

3D structures of tissues, which can be termed microtissues, can be constructed using many techniques including hanging droplets or using 3D supports comprised of Matricel or hydrogels to create small spheroid and other shapes that can better mimic actual tissues. Typically the size is limited by the diffusion of nutrients into the 3D structure. In some cases, the 3D is created incorporating stem cells and can be termed an organoid (N. de Souza, Organoids. Nature Methods volume 15, page 23 (2018); "Method of the Year 2017: Organoids" Nature Methods 2018/01/03/online, 15 http://dx.doi.org/10.1038/nmeth.4575. 10.1038/nmeth.4575, Yin, Xiaolei et al. Engineering Stem Cell Organoids, Cell Stem Cell, Volume 18, Issue 1, 25-38). While organoids are a promising technology, the creation of organoids suffers from process variablity and the use of cells typically not derived directly from tissue. This invention solves the problems of releasing cells from solid tissues for multiple applications including growing cells on 2D surfaces, 3D organoids, and cell suspensions.

Next Generation Sequencing (NGS) of single cells is rapidly changing the state of knowledge of cells and tissue, discovering new cell types, and increasing understanding of the diversity of how cells and tissue function. Single cell NGS RNA sequencing (Saliba A. E., et. al., Nucleic Acids Res. 2014; 42(14):8845-60.) (Shapiro E. et. al., Nat Rev Genet. 2013; 14(9):618-30.) is unveiling the complexity of cellular expression, and the heterogenity from cell to cell, and from cell type to cell type (Buettner F. et. al., Nat Biotechnol. 2015; 33(2):155-60.). In situ sequencing (Ke R et. al., Nat Methods. 2013; 10(9):857-60.), (Lee J H, et. al., Nat Protoc. 2015; 10(3):442-58.) (Lee J H, et. al., Science. 2014, 21; 343(6177):1360-3.) has shown the feasability of directly sequencing fixed cells. However, for RNA, many fewer reads are generated with in situ sequencing, biasing against detection of low abundant transcripts. Photoactivatable tags have been used to capture mRNA from single cells (Lovett, D., et. al., Nat Methods. 2014; 11(2):190-6.) from known locations in tissue, albeit with low throughput capture and manual cell collection.

The NGS market has grown explosively over the last 10 years with cost reductions and throughput increases exceeding Moore's law. The applications have expanded from whole genome sequencing to RNA-Seq, ChIP-Seq, exome sequencing, to now single-cell sequencing, single nuclei sequencing, ATAC-Seq, and many other exciting applications. The power and low cost of NGS is broadly changing life sciences and moving into translational medicine and the clinic as precision medicine begins. Until recent years essentially all of the NGS analysis was of 'bulk samples' where the nucleic acids of numerous cells had been pooled. There is a need for systems that integrate the sample preparation of single-cell suspensions, and single-cell libraries, and bulk libraries starting from original unprocessed fresh specimens as well as banks of frozen tissue and Formalin-Fixed Paraffin-Embedded (FFPE) tissue. This instant invention enables a system, cartridges, and processes to process solid tissues from many types of specimens comprising single cells, single nuclei, and nucleic acids.

Single-cell sequencing is rapidly changing the state of knowledge of cells and tissue, discovering new cell types, and increasing the understanding of the diversity of how cells and tissue function. Single-cell RNA sequencing (Shapiro E. Biezuner T, Linnarsson S. Single-cell sequencing-based technologies will revolutionize whole-organism science. Nat Rev Genet. 2013; 14(9):618-30. PMID: 23897237) has highlighted the complexity of cellular expression, and the large heterogeneity from cell-to-cell, and from cell type-to-cell type (Buettner F. Natarajan K N, Casale F P, Proserpio V, Scialdone A, Theis F J, Teichmann S A, Marioni J C, Stegle O. Computational analysis of cell-to-cell heterogeneity in single-cell RNA-sequencing data reveals hidden subpopulations of cells. Nat Biotechnol. 2015; 33(2):155-60. PMID: 25599176). Single-cell sequencing (Wang., Y. and N. E. Navin. Advanced and Applications of single-cell sequencing technologies. Molecular Cell. 2015. 58:598-609. PMID 26000845.) is being applied to development, brain structure and function, tumor progression and resistance, immunogenetics, and more.

Single cell nucleic acid sequencing technology and methods using NGS and Next Next Generation Sequencing (NNGS), such as nanopores, are rapidly evolving. Common components are incorporation of a marker or barcode for each cell and molecule, reverse transcriptase for RNA sequencing, amplification, and pooling of sample for NGS and NNGS (collectively termed NGS) library preparation and analysis. Starting with isolated single cells in wells, barcodes for individual cells and molecules have been incorporated by reverse transcriptase template switching before pooling and polymerase chain reaction (PCR) amplification (Islam S. et. al. Genome Res. 2011; 21(7):1160-7.) (RamskOld D. et. al. Nat Biotechnol. 2012; 30(8):777-82.) or on a barcoded poly-T primer with linear amplification (Hashimshony T. et. al. Cell Rep. 2012 Sep. 27; 2(3):666-73.) and unique molecular identifiers (Jaitin D. A. et. al. Science. 2014; 343(6172):776-9.).

Pioneering work has used micronozzles (Geng T. et. al. Anal Chem. 2014; 86(1):703-12) to produce nanodroplets to perform highly parallel processing of mRNA from single cells with reverse transcription incorporating cell and molecular barcodes from freed primers (inDrop) (Klein A. M. et. al. Cell. 2015,161(5):1187-201.) or primers attached to paramagnetic beads (DropSeq) (Macosko E. Z. et. al. Cell. 2015; 161(5):1202-14.); the lysis conditions and reverse transcriptase described by (Fekete R. A. and A. Nguyen. U.S. Pat. No. 8,288,106. Oct. 16, 2012) are incorporated by reference cited therein are incorporated by reference, including instrumentation, chemistry, workflows, reactions conditions, flowcell design, and other teachings. Both inDrop and DropSeq are scalable approaches have change the scale from 100s of cells previously analyzed to 1,000s and more.

Single-cell sequencing is now providing new information to biologists, genomic scientists, and clinical practitioners, and the single-cell market is growing explosively, perhaps the next great disruption in life sciences and medicine. Multiple companies are providing systems to take single-cell suspensions and create Single-cell RNA sequencing (scRNA-Seq) libraries that are analyzed by the robust NGS sequencing and analysis pipeline. No system integrates the upstream process to produce single-cell suspensions for NGS single-cell sequencing or has integrated from tissue to single-cell or single nuclei libraries.

The production of single-cells or nuclei or nucleic acids from solid and liquid tissue is usually performed manually with a number of devices used without process integration. A combination of gentle mechanical disruption with enzymatic dissociation has been shown to produce single-cells with the highest viability and least cellular stress response (Quatromoni J G, Singhal S, Bhojnagarwala P, Hancock W W, Albelda S M, Eruslanov E. An optimized disaggregation method for human lung tumors that preserves the phenotype and function of the immune cells. J Leukoc Biol. 2015 January; 97(1):201-9. doi: 10.1189/jlb.5TA0814-373. Epub 2014 Oct. 30.).

Many manual protocols for dissociating different tissues exist, for example, Jungblut M., Oeltze K., Zehnter I., Hasselmann D., Bosio A. (2009). Standardized Preparation of Single-Cell Suspensions from Mouse Lung Tissue using the gentleMACS Dissociator. JoVE. 29, doi: 10.3791/1266; Stagg A J, Burke F, Hill S, Knight S C. Isolation of Mouse Spleen Dendritic Cells. Protocols, Methods in Molecular Medicine. 2001: 64: 9-22. Doi: 10.1385/1592591507.; Lancelin, W., Guerrero-Plata, A. Isolation of Mouse Lung Dendritic Cells. J. Vis. Exp. (57), e3563, 2011. DOI: 10.3791/3563; Smedsrod B, Pertoft H. Preparation of pure hepatocytes and reticuloendothelial cells in high yield from a single rat liver by means of Percoll centrifugation and selective adherence. J Leukocyte Biol. 1985: 38: 213-30; Meyer J, Gonelle-Gispert C, Morel P, BOhler L Methods for Isolation and Purification of Murine Liver Sinusoidal Endothelial Cells: A Systematic Review. PLoS ONE 11(3) 2016: e0151945. doi:10.1371/journal.pone.0151945; Kondo S. Scheef E A, Sheibani N, Sorenson C M. "PECAM-1 isoform-specific regulation of kidney endothelial cell migration and capillary morphogenesis", Am J Physiol Cell Physiol 292: C2070-C2083, (2007); doi: Ehler, E., Moore-Morris, T., Lange, S. Isolation and Culture of Neonatal Mouse Cardiomyocytes. J. Vis. Exp. (79), e50154, doi: 10.3791/50154 (2013); Volovitz I Shapira N, Ezer H, Gafni A, Lustgarten M, Alter T, Ben-Horin I, Barzilai O, Shahar T, Kanner A, Fried I, Veshchev I, Grossman R, Ram, Z. A non-aggressive, highly efficient, enzymatic method for dissociation of human brain-tumors and brain-tissues to viable single cells. BMC Neuroscience (2016) 17:30 doi: F. E Dwulet and M. E. Smith, "Enzyme composition for tissue dissociation," U.S. Pat. No. 5,952,215, Sep. 14, 1999.

For example, solid tissue of interest is usually dissected and then minced into 1-5 mm pieces by hand or a blender type of disruptor is used. Enzymes or a mixture of enzymes, such as collagenases, hydrauronadase, papain, proteases, DNase, etc., are added and the specimen incubated, typically with shaking or rotation to aid dissociation to prepare single cells or nuclei from tissue. In many procedures, the specimen is triturated multiple times or mechanically disrupted. The mechanical disruption may be through orifices, grinding, homogenization, forcing tissue through screens or filters, sonication, blending, bead-beating, rotors with features that dissociate tissue, and other methods to physically disrupt tissue to help produce single cells.

Following dissociation, in some embodiments the dissociated sample is passed through a filter, such as a 70 μm filter, to retain clumps of cells or debris. The filtrate which contains single cells or nuclei may be further processed to change the media or buffer; add, remove, or deactivate enzymes; concentrate cells or biomolecules, lyse red blood cells, or capture specific cell types. The processing typically involves multiple steps of centrifugation and resuspension, density gradients, or magnetic bead capture of specific cell types using antibodies, or other affinity capture ligands, or fluorescent cell-activated sorting (FACS), or other methods. The titer and viability of the single-cell suspension is usually determined using optical imaging with a microscope and haemocytometer, or an automated instrument. In many cases, the viability is determined using Trypan blue or fluorescent dyes. Quality control can include characterization of the nucleic acids by gel electrophoresis on an instrument such as a BioAnalyzer, or the determination of the expression of certain genes using reverse transcriptase and quantitative polymerase chain reaction (RT-qPCR), or other relevant methods.

The rapid production of nuclei can give a snapshot of gene expression (Habib N, Li Y, Heidenreich M, Swiech L, Avraham-Davidi I, Trombetta J J, Hession C, Zhang F, Regev A. Div-Seq: Single-nucleus RNA-Seq reveals dynamics of rare adult newborn neurons. Science. 2016 Aug. 26; 353(6302):925-8. doi: 10.1126/science.aad7038. Epub 2016 Jul. 28; Grindberg R V, Yee-Greenbaum J L, McConnell M J, Novotny M, O'Shaughnessy A L, Lambert G M, Araiizo-Bravo M J, Lee J, Fishman M, Robbins G E, Lin X, Venepally P, Badger J H, Galbraith D W, Gage F H, Lasken R S. RNA-sequencing from single nuclei. Proc Natl Acad Sci USA. 2013 Dec. 3; 110(49):19802-7. doi: Epub 2013 Nov. 18.).

The production of nuclei from tissue can be performed using a Dounce homogenizer in the presence of a buffer with a detergent that lyses cells but not nuclei. Nuclei can also be prepared starting from single cell suspensions (CG000124_SamplePrepDemonstratedProtocol_-_Nuclei_RevB,10× Genomics, https://assets.contentful.com/an68im79xiti/6Fh-JX6yndYy0OwskGmMc81/48c341c178fe afa3ce21f5345e-d3367b/CG000124_SamplePrepDemonstratedProtocol_-_Nuclei_RevB.pdf) by addition of a lysis buffer such as 10 mM Tris-HCl, 10 mM NaCl, 3 mM MgCl2 and 0.005% Nonidet P40 in nuclease-free water and incubation for 5 min on ice before centifugation to pellet the nuclei followed by resuspension in a resuspension buffer such as 1× Phosphate Buffered Saline (PBS) with 1.0% BSA and 0.2 U/pIRNase Inhibitor. The nuclei may be repeatedly pelleted and resuspended to purify them or density gradients or other purification methods used. The titer and viability of the nuclei suspension is usually determined using optical imaging with a microscope and haemocytometer, or an automated instrument with viability determined using Trypan blue or fluorescent dyes.

The multi-process workflow to produce and characterize single-cells and nuclei from tissue is a usually performed manually using several devices without process integration, limiting the scalablity of single cell sequencing and the integration with downstream processes to create a sample-to-answer system. It is laborious and requires skilled technicians or scientists, and results in variability in the quality of the single-cells, and, therefore, in the downstream libraries, analysis, and data. The multiple steps and skill required can lead to differing qualities of single cells or nuclei produced even from the same specimen, limiting clinical utility. Today, the production of high quality single-cells can take months of optimization.

Standarization is necessary before routine single-cell preparation can be performed, particularly in clinical settings. In addition, the length of the process and the process of dissociation can lead to the tissue and cells changing physiology and altering their expression of biomolecules such as RNA, proteins, lipids, and metabolites in response to the stresses of the procedure, accentuated by potentially long processing times. A crucial recent insight is that cell processing methods, for example, the use of a protease to dissociate cells from tissue (Lacar B, Linker S B, Jaeger B N, Krishnaswami S, Barron J, Kelder M, Parylak S, Paquola A, Venepally P, Novotny M, O'Connor C, Fitzpatrick C, Erwin J, Hsu J Y, Husband D, McConnell M J, Lasken R, Gage F H. Nuclear RNA-seq of single neurons reveals molecular signatures of activation. Nat Commun. 2016 Apr. 19; 7:11022. doi: 10.1038/ncomms11022. PMID: 27090946.) can alter gene expression by placing cells under stress, confounding analysis of the true transcriptome.

Robust, automated sample preparation is required to simplify workflows before full process or physical integration with downstream NGS analysis can be achieved to produce true sample-to-answer solid tissue to single cell/nuclei NGS analysis systems in the future. Robust processes and automated systems are required that will input a wide range of tissues from a wide range of organisms and tissues and produce high-quality single-cell or nuclei suspensions without intervention, at acceptable viability for suspensions, with minimal changes to gene expression patterns.

To achieve a standardized process will require a system that automates the sample preparation of cells or nuclei from tissue with a single-use disposable cartridge. In some cases, microvalves can be used in cartridges. Microvalves are comprised of mechanical (thermopneumatic, pneumatic, and shape memory alloy), non-mechanical (hydrogel, sol-gel, paraffin, and ice), and external (modular built-in, pneumatic, and non-pneumatic) microvalves (as described in: C. Zhang, D. Xing, and Y. Li., Micropumps, microvalves, and micromixers within PCR microfluidic chips: Advances and trends. Biotechnology Advances. Volume 25, Issue 5, September-October 2007, Pages 483-514; Diaz-Gonzalez M., C. Fernandez-Sanchez, and A. Baldi A. Multiple actuation microvalves in wax microfluidics. Lab Chip. 2016 Oct. 5; 16(20): 3969-3976; Kim J., Stockton A M, Jensen E C, Mathies R A. Pneumatically actuated microvalve circuits for programmable automation of chemical and biochemical analysis. Lab Chip. 2016 Mar. 7; 16(5):812-9. doi: 10.1039/c51c01397f; Samad M F, Kouzani A Z. Design and analysis of a low actuation voltage electrowetting-on-dielectric microvalve for drug delivery applications. Conf Proc IEEE Eng Med Biol Soc. 2014; 2014:4423-6. doi: Samad M F, Kouzani A Z. Design and analysis of a low actuation voltage electrowetting-on-dielectric microvalve for drug delivery applications. Conf Proc IEEE Eng Med Biol Soc. 2014; 2014:4423-6. doi: Lee E, Lee H, Yoo S I, Yoon J. Photothermally triggered fast responding hydrogels incorporating a hydrophobic moiety for light-controlled microvalves. ACS Appl Mater Interfaces. 2014 Oct. 8; 6(19):16949-55. doi: Epub 2014 Sep. 25; Liu X, Li S. An electromagnetic microvalve for pneumatic control of microfluidic systems. J Lab Autom. 2014 October; 19(5):444-53. doi: Epub 2014 Apr. 17; Desai A V, Tice J D, Apblett C A, Kenis P J. Design considerations for electrostatic microvalves with applications in poly(dimethylsiloxane)-based microfluidics. Lab Chip. 2012 Mar. 21; 12(6):1078-88. doi: Epub 2012 Feb. 3; Kim J, Kang M, Jensen E C, Mathies R A Lifting gate polydimethylsiloxane microvalves and pumps for microfluidic control. Anal Chem. 2012 Feb. 21; 84(4):2067-71. doi: 10.1021/ac202934x. Epub 2012 Feb. 1; Lai H, Folch A. Design and dynamic characterization of "single-stroke" peristaltic PDMS micropumps. Lab Chip. 2011 Jan. 21; 11(2):336-42. doi: 10.1039/c01c00023j. Epub 2010 Oct. 19). The system embodiments described herein can operate cartridges with no valves, or valves can be incorporated into the cartridges to direct flow.

Fluidic connections between cartridges and the instrument fluidics can be achieved by the use of spring-loaded connectors and modular microfluidic connectors as taught by Jovanovich, S. B. et. al. Capillary valve, connector, and router. Feb. 20, 2001. U.S. Pat. No. 6,190,616 and Jovanovich; S. B. et. al. Method of merging chemical reactants in capillary tubes, Apr. 22, 2003, U.S. Pat. No. 6,551,839; and Jovanovich, S., I. Blaga, and R. McIntosh. Integrated system with modular microfluidic components. U.S. Pat. No. 7,244,961. Jul. 17, 2007. which are incorporated by reference and their teachings which describe the modular microfluidic connectors and details of modular microfluidic connectors, including their use as multiway valves, routers, and other functions including microfluidic circuits to perform flowthrough reactions and flow cells with internally reflecting surfaces.

The surface chemistries of the paramagnetic beads and conditions to bind cells or precipitate, wash, and elute nucleic acids and other biomolecules onto surfaces is well understood, (Boom, W. R. et. al. U.S. Pat. No. 5,234,809. Aug. 10, 1993.), (Reeve, M. and P. Robinson. U.S. Pat. No. 5,665,554. Sep. 9, 1997.), (Hawkins, T. U.S. Pat. No. 5,898,071. Apr. 27, 1999.), (McKernan, K. et. al. U.S. Pat. No. 6,534,262. Mar. 18, 2003.), (Han, Z. U.S. Pat. No. 8,536,322. Sep. 17, 2013.), (Dressman et al., "Transforming single DNA molecules into fluorescent magnetic particles for detection and enumeration of genetic variation" Proc. Natl. Acad. Sci. 100(15):8817-8822 (2003)), (Ghadessy et al., "Directed evolution of polymerase function by compartmentalized self-replication", Proc. Natl. Acad. Sci. 98(8): 4552-4557 (2000)), (Tawfik and Griffiths, "Man-made cell-like compartments for molecular evolution" Nat. Biotech. 16(7):652-656 (1998)), (Williams et al., "Amplification of complex gene libraries by emulsion PCR" Nat. Meth. 3(7): 545-550 (2006)), and many chemistries are possible and within the scope of the instant disclosure.

BRIEF SUMMARY OF THE INVENTION

Disclosed herein is a Sample Processing System that processes original or processed samples for bioanalysis or for the development of microtissues or organoids. The Sample Processing System processes are comprised of enzymatic and mechanical disruption mechanisms with integrated fluidic processes. This invention enables, among other things, the implementation of a Sample Processing System that inputs solid, liquid, or gaseous samples including tissue or other biological samples, and processes the samples for bioanalysis and other analyses.

In some embodiments, the sample or specimen is a tissue specimen. The tissue can be from any source such as a human, animal, or plant tissue. Examples of tissues include, without limitation, a biopsy sample, a core biopsy sample, a fine needle aspirate, cellular conglomerate, an organ fragment, whole blood, bone marrow, a biofilm, or any other solid, semi-solid, gelatinous, frozen or fixed three dimensional or two dimensional cellular matrix of biological. In another embodiment the released nucleic acid is bound to a membrane, chip surface, bead, surface, flow cell, or particle. The term specimen is used to mean samples and tissue specimens.

In one embodiment the Sample Processing System is used for tissue processing. A Tissue Processing System embodiment can be implemented as a flexible, extensible system that can process solid or liquid tissue and other samples into single cells, nuclei, organelles, and biomolecules with mechanical and enzymatic or chemical processes to produce single cells in suspension, nuclei, subcellular components, and biomolecules such as macromolecules comprised of nucleic acids, comprised of DNA and RNA; proteins; carbohydrates; lipids; biomolecules with multiple types of macromolecules; metabolites; and other biological components, including natural products for bioanalysis in suspension, in solution, or attached to a surface. In some embodiments, the Tissue Processing System performs affinity or other purifications to enrich or deplete cell types, organelles such as nuclei, mitochondria, ribosomes, or other organelles, or extracellular fluids. In some embodiments the Tissue Processing System can perform NGS library preparation. In some embodiments, the Tissue Processing System processes tissue into single-cell libraries for sequencing including Sanger, NGS, NNGS and other nucleic acid sequencing technolgies, protein sequencing, or protoeomics, or other analytical methods.

Disclosed herein are different embodiments of Sample Processing Systems that integrate two or more of the overall steps to take samples from specimens (i.e., tissue, biofilms, other multi-dimensional matrices with cells or viruses, liquids) and prepare single cell or nuclei in suspensions or on surfaces, or further process the specimens into biomolecules including macromolecules comprised of nucleic acids, comprised of DNA and RNA; proteins; carbohydrates; lipids; biomolecules with multiple types of macromolecules; metabolites; and other biological components, including natural products). In some embodiments specimen can be processed into NGS sequencing libraries, or fully integrated with an analytical system to produce a sample-to-answer systems such as a sample-to-answer genomic system.

In some embodiments the Sample Processing System can be integrated with downstream bioanalysis to create a sample-to-answer system. In a preferred embodiment of the Sample Processing System, a Tissue Processing System processing embodiment is integrated with a nucleic acid bioanalysis system to sequence nucleic acids from tissues. Integrated is used to mean the workflows directly interface or in other contexts that the physical system directly interfaces or is incorporated into a system, instrument, or device. In one embodiment, the Tissue Processing System is integrated with a nucleic acid sequencer to produce a sample-to-answer system.

In one embodiment the Tissue Processing System can be used to create microtissues or organoids directly in a cartridge using the hanging droplet method or other methods, or the output of the system can be used as the starting point for creating microtissues or organoids off of the cartridge.

The Sample Processing System can have multiple subsystems and modules that perform processing or analysis. In a preferred embodiment of the Sample Processing System, one or more cartridges performs one or more steps in the processing workflow. In some embodiments the cartridges have multiple processing sites such as processing chambers that can process more than one sample. In some embodiments a cap couples mechanical disruption on the cartridge from a Physical Dissociation Subsystem to the Enzymatic and Chemical Dissociation Subsystem in a processing chamber. In some embodiments reagents from an Enzymatic and Chemical Dissociation Subsystem are delivered to the cartridge by a Fluidic Subsystem to regions that are used as Pre-Processing Chambers and Processing Chambers to disrupt or dissociate the specimen and process the cells, subcellular components, and biomolecules for bioanalysis.

The addition of fluids can be controlled by a Fluidic Subsystem with the complete system controlled by software in a Control Subsystem which can include the user interface through a device comprised of monitor, embedded display, touch screen; or through audio commands through the system or an accessory devices such as a cell phone or microphone. In some instances the Control Subsystem can include interfaces to laboratory information management systems, other instruments, databases, analysis software, email, and other applications.

In some embodiments, the amount of dissociation is monitored at intervals during the dissociation and in some instances the viability determined during processing using a Measurement Subsystem. The degree of dissociation and/or viability can be determined inside the main dissociation compartment and/or in a separate compartment or channel, and/or in the external instrument.

In some embodiments, cell imaging solutions, such as cell type specific antibodies, stains, or other reagents, can be added to the tissue or single cells or nuclei for additional processing or imaging. The imaging can capture cells, subcellular structures, or histological or other data. In some embodiments the images can be analyzed to direct the operation and workflow of the Sample Processing System through decisions trees, hash tables, machine learning, or artificial intelligence.

In some embodiments, single cells or nuclei in suspension or on surfaces are further processed using magnetic bead or particle technologies using a Magnetic Processing module to purify or deplete cell types, nuclei, nucleic acids, or other biomolecules.

The term singulated cells is used to mean single cells in suspension or on a surface or in a well including a microwell or nanowell such that they can be processed as single cells. The term singulated cells is also used at times to encompass single nuclei.

In one embodiment, the specimen is added to a cartridge which performs both physical and enzymatic dissociation of the tissue. In some embodiments the Singulator System performs trituration and other physical dissociation modalities as a step or steps in the process of singulating cells. The physical dissociation modalities include passing the specimen through screens, filters, orifices, grinding, blending, sonication, smearing, bead beating, and other methods known to one skilled in the art to physically disrupt tissue to help produce single cells or nuclei or nucleic acids or other biomolecules.

In one embodiment, the specimen is added to a cartridge which performs both physical and chemical dissociation of the tissue into nuclei. In some embodiments the Singulator System performs trituration and other physical dissociation modalities as a step or steps in the process of producing nuclei suspensions. The physical dissociation modalities include passing the specimen through screens, filters, orifices, gaps, grinding, blending, sonication, smearing, bead beating, and other methods known to one skilled in the art to physically disrupt tissue to help produce nuclei or nucleic acids or other biomolecules when using chemical treatment of tissues.

In one embodiment, the Sample Processing System is a Singulator System embodiment. The Singulator System described can input raw, unprocessed samples, or other primary or secondary samples, and output single cells or nuclei ready for single cell or nuclei analysis or for additional processing, e.g., to purify specific cell types with antibodies or by cell sorting or growth, library preparation, or many other applications. A Singulator System embodiment dissociates single cells or nuclei from specimens such as tissue, blood, bodily fluid or other liquids or solids containining cells to produce single cells in suspensions or nuclei, or on surfaces, in matrices, or other output configurations. In a preferred Singulation System described embodiment, there is a cartridge that inputs tissue and/or other specimens and outputs single cells or nuclei, preferably of known titer in a buffer supplemented with media such as Hank's buffer with 2% fetal calf serum.

In some embodiments, the Sample Processing System, such as a Singulator System embodiment, uses enzymes to assist in the process of singulating cells including enzymes to preserve nucleic acids and prevent clumping. The enzymes and additives are comprised of but not limited to collagenases (e.g., collagenases type I, II, III, IV, and others), elastase, trypsin, papain, tyrpLE, hyaluronidase, chymotrypsin, neutral protease, pronase, liberase, clostripain, caseinase, neutral protease (Dispase), DNAse, protease XIV, RNase inhibitors, or other enzymes, protease inhibitors, active site inhibitors, EDTA, EGTA, biochemicals, or chemicals such as Triton X-100, Nonidet P40, detergents, surfactants, etc. In other embodiments, different reagents or mixtures of reagents are applied sequentially to dissociate the biological sample or specimen into single-cell suspensions.

In some embodiments, the Sample Processing System, such as a Singulator System embodiment, uses chemicals, enzymes, or both to assist in the process of producing nuclei from solid tissue in a nuclei isolation solution, assist in tissue dissociation, to preserve nucleic acids, and to prevent clumping. The chemicals are comprised of but not limited to detergents, surfactants, non-ionic surfactants, Triton X-100, Tween, Brij, CHAPS, Nonidet P40, Igepal, glycosides, HEGA, MEGA, or digitonin, the enzymes are comprised of collagenases (e.g., collagenases type I, II, Ill, IV, and others), elastase, trypsin, papain, tyrpLE, hyaluronidase, chymotrypsin, neutral protease, pronase, liberase, clostripain, caseinase, neutral protease (Dispase), DNAse, protease XIV, or other enzymes. In some embodiments inhibitors such as RNase inhibitors, protease inhibitors, active site inhibitors, or biochemicals that sequester or chelate ions essential for RNases, comprising EDTA or EGTA or sodium citrate, can be used in solutions. In some embodiments, spermine or spermidine or sodium butyrate, or sodium orthovanadate, or sodium fluoride are included in the nuclei isolation solution or in nuclei storage solutions. In other embodiments, different reagents or mixtures of reagents are applied sequentially to dissociate the biological sample or specimen into single-cell suspensions and then the single cells are processed into nuclei. In some embodiment, the viscosity of the solutions are increased using chemicals comprised of ficoll, or gylcerol, or dextran, or sucrose, or trehalose, or polyethylene glycol, or cellulose or other compounds to slow diffusion rates of RNases or DNases or other enzymes or compounds that degrade biomolecules. In some embodiments the counterions in the buffers are acetate.

In some embodiments the Singulator System produces cell suspensions of known titers and viability. In some embodiments the Singulator System produces nuclei suspensions of known titers and quality. In some embodiments the Singulator System monitors the viability and/or the amount of singulation of a sample and adjusts the treatment time and concentration of enzymes or other dissociation agents by monitoring of the dissociation, for example by the production of single cells or nuclei. The monitoring can be in real time, in intervals, or endpoints or any combinations thereof.

The Singulator System can in some embodiments select from sets of reagents to dissociate tissue and adjust according to production of single cells or viability of cells as monitored by the system, in some instances in real time, at intervals, or as an endpoint. The single-cell suspensions produced by the Singulator System can be used to generate cells with therapeutic application, e.g., re-grow new tissues and/or organs and/or organisms.

The Singulator System has advantages over existing technology and can produce single cells, nuclei, or biomolecules from tissue in an automated and standardized instrument that can in some embodiments process the specimens into NGS libraries or other preparations. The Singulator System will enable users, e.g., researchers, clinicians, forensic scientists, and many disciplines to perform identical processing on biosamples, reducing user variability, and throughput constraints of manual processing.

Embodiments of the Singulation System can prepare single-cells or nuclei or nucleic acids for analysis by methods comprised of DNA sequencing, DNA microarrays, RNA sequencing, mass spectrometry, Raman spectroscopy, electrophysiology, flow cytometry, mass cytometry, and many other analytical methods well known to one skilled in the art including multidimensional analysis (e.g., LC/MS, CE/MS, etc.). In addition, single-cell suspensions or on surfaces or matrices can be used to grow additional cells including genetically altered by methods such as CRISPR, engineered viral or nucleic acid sequences, in tissue culture, or to grow tissues or organs for research and therapeutic purposes.

The Singulator System embodiment described is compatible with commercially available downstream library preparation and analysis by both NGS and NNGS sequencers. The term NGS is used to connote either NGS or NNGS sequencers or sample preparation methods as appropriate. As contemplated herein, next generation sequencing or next-next generation sequencing refers to high-throughput sequencing, such as massivley parallel sequencing, (e.g., simultaneously (or in rapid succession) sequencing any of at least 1,000, 100,000, 1 million, 10 million, 100 million, or 1 billion polynucleotide molecules). Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumine), Digital Gene Expression (Helicos), next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, Genius (GenapSys), DNA nanoball sequencing (Complete Genomics), or nanopore (e.g., Oxford Nanopore, Roche) platforms and any other sequencing methods known in the art.

In another aspect provided herein is an apparatus, composition of matter, or article of manufacture, and any improvements, enhancements, and modifications thereto, as described in part or in full herein and as shown in any applicable Figures, including one or more features in one or more embodiment.

In another aspect provided herein is an apparatus, composition of matter, or article of manufacture, and any improvements, enhancements, and modifications thereto, as described in part of in full herein and as shown in any applicable Figures, including each and every feature.

In another aspect provided herein is a method or process of operation or production, and any improvements, enhancements, and modifications thereto, as described in part or in full herein and as shown in any applicable Figures, including one or more feature in one or more embodiment.

In another aspect provided herein is a method or process of operation or production, and any improvements, enhancements, and modifications thereto, as described in part or in full herein and as shown in any applicable Figures, including each and every feature.

In another aspect provided herein is a product, composition of matter, or article of manufacture, and any improvements, enhancements, and modifications thereto, produced or resulting from any processes described in full or in part herein and as shown in any applicable Figures.

In one embodiment the single-cell suspension is prepared for a bioanalysis module for downstream analysis including but not limited to sequencing, next generation sequencing, next next generation sequencing, protein sequencing, proteomic analysis, genomic analysis, gene expression, gene mapping, carbohydrate characterization and profiling, lipid characterization and profiling, flow cytometry, imaging, DNA or RNA microarray analysis, metabolic profiling, functional, or mass spectrometry, or combinations thereof.

In another aspect provided herein is a data analysis system that correlates, analyzes, stores, and visualizes the analytical information of a sample component such as its viability, degree of single cell or nuclei dissociation, with the processing step and measures the change over time, and/or amount of enyzmatic activity, and/or physical disruptions of the original biological specimen. In another aspect provided herein is a data analysis system that correlates, analyzes, stores, and visualizes the analytical information of a sample component and shares metadata of the sample with downstream or upstream laboratory information systems.

In another aspect provided herein is a data analysis system that correlates, analyzes, and visualizes the analytical information of a sample component such as its viability, degree of single cell or nuclei dissociation, with the processing step and measures the change over time, and/or amount of enyzmatic activity, and/or physical disruptions of the original biological specimen and adjusts the processing parameters from the analytical information.

The Singulator System is a novel platform that automates and standardizes the only portion of the single-cell NGS workflow that has not been automated. This will have broad impacts. Process standardization will be critical for comparison of data from lab to lab or research to researcher. The Human Cell Atlas project intends to freely share the multinational results in an open database. However, with no standardization of the complete process, direct comparisons will greatly suffer from widely varying impacts of the first processing step of producing single-cells or nuclei from tissue. Additionally, when single-cell or nuclei sequencing becomes clinically relevant, the standardization and de-skilling of the production of single-cells or nuclei will be required to be performed by an automated instrument such as the Singulator System.

In another aspect, provided herein is a system comprising: (a) an instrument comprising: (i) one or more cartridge interfaces configured to engage a cartridge; (ii) a fluidic subsystem comprising: (1) one or more containers containing one or more liquids and/or gasses; (2) one or more fluid lines connecting the containers with fluid ports in the cartridge interface; and (3) one or more pumps configured to move liquids and/or gasses into and/or out of the fluid port(s); (iii) one or more mechanical subsystems comprising an actuator; (iv) optionally, one or more magnetic processing modules comprising a source of magnetic force, wherein the magnetic force is positioned to form a magnetic field in one or more processing chambers; (v) optionally, one or more measurement modules; (vi) optionally, one or more control subsystems comprising a processor and memory, wherein the memory comprises code that, when executed by the processor, operates the system; and (b) one or more cartridges, each engaged with one of the cartridge interfaces, wherein each cartridge comprises: (i) a sample inlet port; (ii) one or more cartridge ports communicating with the fluid ports in the cartridge interface; (iii) a preprocessing chamber communicating with the sample inlet port and with at least one cartridge port, and comprising a tissue disruptor configured for mechanical disruption of tissue, wherein the tissue disruptor engages with and is actuated by the actuator when the cartridge is engaged with the cartridge interface; (iv) a strain chamber communicating with the preprocessing chamber configured to separate cells and/or nuclei from disrupted tissue optionally combined with either the preprocessing or processing chambers; (v) a processing chamber communicating with the strain chamber, optionally communicating with one or more cartridge ports and configured to perform one or more processing steps on separated cells and/or nuclei; and (vi) optionally, one or more waste chambers fluidically connected with the processing chamber. In one embodiment the tissue disruptor comprises a grinder, a pestle or a variable orifice. In another embodiment the system further comprises a barcode reader. In another embodiment the system comprises a measurement module that performs optical imaging to measure titer, clumping, and/or viability of cells or nuclei or properties of biomolecules. In another embodiment the system comprises a measurement module and a control system, wherein the measurement module measures, and one or more time points, characteristics of a sample in the processing chamber, and control system comprises code that determines a state of the sample, e.g., viability or degree of single cell or nuclei dissociation, and that adjusts processing parameters. In another embodiment the system further comprises (c) one or more analysis modules, wherein an input port of the analysis module is in fluid communication with the processing chamber. In another embodiment the analysis module performs an analysis selected from one or more of: DNA or RNA sequencing, next generation DNA or RNA sequencing, next next generation DNA or RNA sequencing of nucleic acids and their adducts such as epigenetic modifications; nanopore sequencing of nucleic acids and their adducts, single cell DNA sequencing of nucleic acids and their adducts; single nuclei RNA sequencing of nucleic acids and their adducts; PCR, digital droplet PCR, qPCR, RT-qPCR, genomic analysis, gene expression analysis, gene mapping, DNA fragment mapping; imaging including optical and mass spectrometry imaging; DNA or RNA microarray analysis; fluorescent, Raman, optical, mass spectrometery and other detection modalities of nucleic acids acids and their adducts with and without labels; proteomic analysis, including fluorescent, Raman, optical, mass spectrometery, protein sequencing, and other detection modalities of proteins and peptides and their adducts and modifications; carbohydrate characterization and profiling including sequencing, fluorescent, Raman, optical, mass spectrometery, and other detection modalities of carbohydrates and their adducts and other covalent polymers; lipid characterization and profiling including sequencing, fluorescent, Raman, optical, mass spectrometery, and other detection modalities of lipids and their adducts and other covalent polymers; flow cytometry; characterization of cells and profiling including fluorescent, Raman, optical, mass spectrometery, and other detection modalities of cells and their adducts and other covalent polymers; metabolic profiling including sequencing, fluorescent, Raman, optical, mass spectrometery, and other detection modalities of metabolites and their adducts and other covalent polymers; functional analysis including protein protein interactions; bioinformatic analysis of cells, organelles, and biomolecules; and mass spectrometry and other analytical methods.

In another embodiment the cartridge interface comprises a means of positioning the cartridge in the instrument that engages the fluidic subsystem and the mechanical module and optionally is temperature controlled. In another embodiment the cartridge is disposable.

In another aspect provided herein is a method comprising: (a) providing a tissue sample to a preprocessing chamber; (b) automatically performing mechanical and enzymatic/chemical disruption of the tissue in the preprocessing chamber to produce disrupted tissue comprising released cells and/or nuclei and debris; (c) automatically moving the disrupted tissue into a strain chamber comprising a strainer and/or filter and separating the released cells and/or nuclei from the debris therein; and (d) automatically moving the released cells and/or nuclei into a processing chamber which can be combined with the strain chamber in a preferred embodiment. In another embodiment automatically moving further comprises performing at least one processing step on the released cells and/or nuclei in the processing chamber. In another embodiment processing comprises one or more automatically performed processes selected from: (I) lysing cells; (II) capturing cells; (III) isolating nucleic acid; (IV) isolating protein; (V) converting RNA into cDNA; (VI) preparing one or more libraries of adapter tagged nucleic acids; (VII) performing PCR or other DNA amplification methods; (VIII) isolating individual cells or individual nuclei in nanodrops or nanoboluses or nanowells or in media such as agarose that will limit diffusion of molecules of interest between cells or nuclei; and (IX) outputting released cells and/or nuclei into output vessels such as 8 well strip tubes, microtiter plates, Eppendorf tubes, a chamber in the cartridge, or other vessels capable of receiving cell suspensions. In another embodiment the method further comprises: automatically capturing the released cells and/or nuclei in the processing chamber by binding to magnetically attractable particles comprising moieties having affinity for the cells and/or nuclei and applying a magnetic force to the processing chamber to immobilize the captured cells and/or nuclei. In another embodiment the method further comprises: automatically monitoring cell and/or nuclei titer in the preprocessing chamber and, when the titer reaches a desired level, exchanging a dissociation solution used to dissociate the tissue for a buffer. In another embodiment the method further comprises automatically monitoring a bioassay in the preprocessing or processing chambers.

In another aspect provided herein is a cartridge comprising: (i) a sample inlet port; (ii) optionally one or more cartridge ports configured to communicate with fluid ports in a cartridge interface; (iii) a preprocessing chamber communicating with the sample inlet port and with at least one cartridge port, and comprising a tissue disruptor configured for mechanical disruption of tissue, wherein the tissue disruptor engages with and is actuated by the actuator when the cartridge is engaged with the cartridge interface; (iv) a strain chamber communicating with the preprocessing chamber configured to separate cells from disrupted tissue that can optionally be combined with the preprocessing or processing chambers; (v) a processing chamber communicating with the strain chamber, optionally communicating with one or more cartridge ports and configured to perform one or more processing steps on separated cells; and (vi) optionally, one or more waste chambers fluidically connected with the processing chamber. In another embodiment the cartridge further comprises a cap that opens and closes the sample inlet port. In another embodiment the cap comprises a tissue disruptor element that moves, for example, about rotationally and back and forth along an axis. In another embodiment the cartridge further comprises a holder. In another embodiment the cartridge further comprises a top piece and a bottom piece connected by collapsible element which allow the top piece and/or the bottom piece to move relative to the holder. In another embodiment the holder comprises a mesh screen. In another embodiment the cartridge further comprises a grinding element for grinding tissue in the preprocessing chamber. In another embodiment the cartridge further comprises an identifier, such as a barcode or other identification system that comprises information about the cartridge and/or its use. In another embodiment the cartridge further comprises a plunger configured to move slideably within the preprocessing chamber. In another embodiment, the cartridge has one or more valves.

In another aspect provided herein is a variable orifice device for disrupting tissue comprising: (a) a first container and a second container fluidically connected through a flexible tube comprising a lumen; (b) an adjustable clamp positioned to clamp the flexible tube, wherein adjusting the clamp alters the cross-sectional area of the lumen; and (c) one or more pumps or devices operatively coupled with the first and/or second containers configured to push liquid in one container through the flexible tubing into the other container. In another embodiment the adjustable clamp comprises an eccentric cam operatively coupled to a motor, wherein rotating the cam closes or opens the clamp.

In another aspect provided herein is a method for disrupting tissue comprising: (a) providing a variable orifice device comprising first container and a second container fluidically connected through a flexible tube comprising a lumen; (b) moving a sample comprising tissue from one of the containers through the flexible tube to another one of the containers; (c) decreasing the cross-sectional area of the lumen and moving the sample from one of the containers through the flexible tube to another one of the containers; (d) repeating step (c) one or more times to disrupt the tissue.

In another aspect provided herein is a system comprising: (a) an instrument comprising: (i) one or more cartridge interfaces, each configured to engage a cartridge and comprising one or more fluid ports; (ii) a fluidics subsystem comprising: (1) one or more sources of liquids and/or gasses; (2) one or more fluid lines communicating with the sources and with fluid ports in the cartridge interface; and (3) one or more pumps configured to move liquids and/or gasses from the sources into and/or out of the one or more fluid ports; (iii) a subsystem comprising an actuator to actuate a tissue disruptor in a cartridge engaged with a cartridge interface (e.g., a mechanical, pneumatic, electromagnetic, or hydraulic actuator); and (b) one or more cartridges, each engaged with one of the cartridge interfaces, wherein each cartridge comprises: (i) one or more cartridge ports communicating with the fluid ports in the cartridge interface; (ii) a preprocessing chamber comprising an opening and, positioned in the opening, a tissue disruptor configured for mechanical disruption of tissue, wherein the tissue disruptor engages with and is actuated by the actuator when the cartridge is engaged with the cartridge interface; and (iii) a processing chamber communicating with the preprocessing chamber, and with one or more cartridge ports and configured to collect a suspension of biological material from the preprocessing chamber. In one embodiment, the instrument further comprises: none, one or a plurality of valves configured to direct positive or negative pressure from the one or more pumps through fluid lines and/or the one or more containers connecting the one or more fluid lines to the fluid ports. In another embodiment the instrument further comprises: a magnetic processing module comprising a source of a magnetic field, wherein the source is positioned to form a magnetic field in a processing chamber of an engaged cartridge. In another embodiment, the instrument further comprises: a measurement subsystem. In another embodiment, the instrument further comprises: a control subsystem comprising a processor, memory, and a local or remote database wherein the memory comprises code that, when executed by the processor, operates the system and can store information of the instrument processes or analytical results from the system in a database. In another embodiment, the instrument further comprises: a waste container communicating with the one or more pumps. In another embodiment, the instrument further comprises: a temperature subsystem configured to regulate temperature in a chamber of the cartridge. In another embodiment, the temperature subsystem comprises a temperature regulating element (e.g., a Peltier, a resistive heater, a circulating fluid), a controller to control the temperature-regulating element and a thermal transfer element that transfers heat from the temperature-regulating element to or from the cartridge chambers. In another embodiment, the temperature subsystem comprises a temperature regulating element (e.g., a Peltier, a resistive heater, a circulating fluid), a controller to control the temperature-regulating element and a thermal transfer element that transfers heat from the temperature-regulating element to or from the reagents and reagent containers. In another embodiment, the actuator comprises a drive head selected from slotted, phillips, quadrex, tri-wing, spanner and hex. In another embodiment, the at least one pump comprises a syringe pump. In another embodiment, the pump communicates through a fluid line with a fluid port in the cartridge interface that engages a cartridge port that communicates with the processing chamber, wherein vacuum applied through the fluid line pulls fluid from the preprocessing chamber into the processing chamber. In another embodiment, the pump communicates through a first fluid line with a container of fluid and with a second line with a fluid port in the cartridge interface that engages a cartridge port that communicates with the preprocessing chamber or the processing chamber, wherein negative pressure applied through the first fluid line pulls fluid from container and positive pressure applied through the second fluid line pushes the fluid into the preprocessing chamber or the processing chamber. In another embodiment, each cartridge interface further comprises a reagent inlet port that communicates with a port in the preprocessing chamber configured to introduce reagent directly into the prepossessing chamber. In another embodiment, the preprocessing chamber communicates with the processing chamber directly through a fluid line, or indirectly, through one or more fluid lines in the interface that communicate with ports in each of the preprocessing chamber and the processing chamber. In another embodiment, the preprocessing chamber comprises no direct cartridge ports. In another embodiment, the cartridge comprises no more than any of one, two, three or four ports communicating with the cartridge interface or with the environment. In another embodiment, the cartridge comprises a plurality of ports communicating with the cartridge interface or with the environment, wherein at least one port is covered by a cap. In another embodiment, the tissue disruptor comprises: (i) a sheath, (ii) a plunger configured to move slidably within the sheath and comprising a coupler to engage the actuator and a head for disrupting tissue, and (iii) a bias mechanism, e.g., spring, that biases the plunger toward a retracted position, i.e. wherein actuation is required to actuate the plunger to a forward position. In another embodiment, the plunger also can rotate around the longitudinal axis of the sheath. In another embodiment, the head has a circumference which, when the head moves within the preprocessing chamber, provides a gap between the head and a wall of the preprocessing chamber between about 25 microns and 400 microns, e.g., sufficient to allow cells or nuclei or microstructures of cells to pass between the head and the wall without rupturing. In another embodiment, the head comprises a disruption surface comprising raised features for disrupting tissue. In another embodiment, the plunger comprises a top side comprising a feature for engaging the actuator. In another embodiment, the tissue disrupter is seated on a seat, e.g., an annular seat, in the preprocessing chamber. In another embodiment, the tissue disrupter head comprises an annular bevel, and the seat in the preprocessing chamber is configured to mate with the bevel such that when the plunger is actuated toward the bottom of the preprocessing chamber, there is a defined annular gap between the head and a wall of the preprocessing chamber, and no gap or a defined minimum gap between the disruption surface of the head and the bottom of the preprocessing chamber. In another embodiment, the preprocessing chamber comprises a bottom surface comprising raised features for disrupting tissue. In another embodiment, the preprocessing chamber communicates with the processing chamber through a fluidic channel connecting a port in a side of the preprocessing chamber with a port in a top of the processing chamber. In another embodiment, the processing chamber further comprises a strainer (e.g., filter or a mesh screen) positioned to strain suspension of biological material entering the processing chamber from the preprocessing chamber. In another embodiment, the processing chamber communicates with a cartridge port configured such that when vacuum is applied to the cartridge port, liquid in the preprocessing chamber is pulled into the processing chamber. In another embodiment, the cartridge further comprises a vacuum trap fluidically connected with and positioned between the cartridge port with the processing chamber. In another embodiment, the processing chamber comprises a drain section and a more narrow slot section and wherein the processing chamber comprises a slanted floor configured to direct fluid in the drain section toward the slot section. In another embodiment, the processing chamber comprises a depression for collecting a suspension of biological material. In another embodiment, the processing chamber communicates with a cartridge port configured to introduce fluids into the processing chamber. In another embodiment, the processing chamber comprises a cover comprising a port that communicates through a fluidic channel with the preprocessing chamber. In another embodiment, the preprocessing chamber comprises a cover comprising a seal (e.g. a friable seal, or septum) that, when removed or opened (e.g., punctured), allows access to the processing chamber. In another embodiment, the processing chamber comprises a cover comprising a seal (e.g. a friable seal, or septum) that, when removed or opened (e.g., punctured), allows access to the processing chamber. In another embodiment, the cartridge further comprises: one or more waste chambers fluidically connected with the processing chamber. In another embodiment, the cartridge further comprises an identifier comprising information about the cartridge and/or its use (e.g., a barcode, an RFID, an EE PROM), and wherein the instrument comprises a reader for reading information in the identifier. In another embodiment, the one or more sources of liquids and/or gasses are comprised in a fluidic subsystem.

In another aspect provided herein is a method comprising: (a) providing a system as disclosed herein, wherein the preprocessing chamber comprises a tissue sample; (b) disrupting the tissue sample by using the actuator to actuate the tissue disrupter to produce a suspension of biological material; and (c) using the fluidic subsystem to move the suspension of biological material from the preprocessing chamber into the processing chamber. In one embodiment, the method further comprises: removing the suspension of biological material from the processing chamber. In another embodiment, the prepossessing chamber further comprises one or more enzymes for digesting extracellular matrix. In another embodiment, the prepossessing chamber further comprises one or more detergents for lysing cell membranes. In another embodiment, the prepossessing chamber further comprises liquid having a viscosity that slows the rate of degradation of RNA or other biomolecules during or after tissue disruption. In another embodiment, disrupting comprises positioning a disruption surface of the head a defined distance from a bottom surface of the preprocessing chamber and rotating the head to disrupt tissue in the preprocessing chamber. In another embodiment, disrupting comprises positioning a disruption surface of the head with respect to a bottom surface of the preprocessing chamber at a plurality of different gap distances and, at each gap distance, rotating the head. In another embodiment, at at least one gap distance at least some portion of the disruption head contacts some portion of the bottom surface. In another embodiment, the widest gap distance between a flat portion of the head surface and flat portion of the bottom of the chamber is no more than any of 6 mm, 5 mm 4 mm, 3 mm, 2 mm, 1 mm, 500 µm, 250 µm, 100 µm, 75 µm, 50 µm, 25 µm, 20 µm, 15 µm, 10 µm, 5 µm, 4 µm, 3 µm, 2 µm, or 1 µm. In another embodiment, the plurality of gap distances between a flat portion of the head surface and flat portion of the bottom of the chamber is any of 2, 3, 4, 5, 6, 7, 8, 9 or 10 and the largest gap distance is no is no more than any of 6 mm, 5 mm 4 mm, 3 mm, 2 mm, 1 mm, 500 µm, 250 µm, 100 µm, 75 µm, 50 µm, 25 µm, 20 µm, 15 µm, 10 µm, 5 µm, 4 µm, 3 µm, 2 µm, or 1 µm. In another embodiment, the method comprises: disrupting tissue with the tissue disruptor; incubating the disrupted tissue with at least one enzyme that digests extracellular matrix; and disrupting the incubated tissue with the tissue disruptor. In another embodiment, the fluidic subsystem applies a vacuum to a cartridge port communicating with the processing chamber to move the suspension of biological material. In another embodiment, the cartridge further comprises a strainer and the suspension of biological material entering the processing chamber is strained to remove particulate matter, e.g., clumps of cells or nuclei or subcellular biomolecules. In another embodiment, the method further comprises, after moving the suspension of biological material, using the fluidics subsystem to introduce a liquid into the preprocessing chamber through a cartridge port and then using the fluidics subsystem to move the liquid into the processing chamber. In another embodiment, the method further comprises using the fluidics subsystem to introduce one or more liquids comprising one or more reagents through a cartridge port into the processing chamber. In another embodiment, the reagent comprises an enzyme or a particle comprising a binding agent (e.g., a binding agent directed against a target on a cell surface or a surface of a nucleus or surface of a virus, or other biological target). In another embodiment, the tissue comprises a target cell and the method further comprises: contacting the suspension of biological material in the processing chamber with solid particles comprising binding agents that bind to the target cells and sequester bound target cells within the suspension of biological material. In another embodiment, the method further comprises separating the bound target cells from the suspension. In another embodiment, the tissue is tumor tissue and the target cells are tumor infiltrating lymphocytes. In another embodiment, the target cells are stem cells or partially differentiated cells. In another embodiment, the method further comprises: determining the expression of one or more genes in cells, nuclei, mitochondria or other organelles of the suspension of biological material. In another embodiment, the one or more genes is a panel comprising a plurality of genes. In another embodiment, the panel comprises genes distinguishing a target cell type, e.g., hepatocytes, neurons, kidney glomerulus parietal cell, cardiomyocytes. In another embodiment, the panel comprises genes distinguishing a CRISPR modified target cell. In another embodiment, the panel comprises genes that are differentially expressed when cells experience stress, e.g., anoikis. In another embodiment, the method comprises preparing a suspension of biological material on each of a plurality of tissue samples under different tissue disruption conditions, and identifying conditions that produce cells or nuclei having a gene expression profile closest to or furthest away from that of cells in the pre-disrupted tissue sample. In another embodiment, the panel comprises one or more housekeeping genes, e.g., a gene constitutively expressed at a relatively constant level in cells regardless of cellular stress states, e.g., Actb, gapdh.

In another aspect provided herein is a cartridge comprising: (i) a preprocessing chamber comprising: (1) an opening and, positioned in the opening, a tissue disruptor configured for mechanical disruption of tissue, and (2) a preprocessing chamber port; and (ii) a processing chamber comprising a processing chamber port communicating with the preprocessing chamber port through a fluid line, and (iii) a cartridge port that communicates with the processing chamber, wherein a vacuum applied to the cartridge port pulls material from the preprocessing chamber into the processing chamber. In one embodiment, the cartridge port communicates with the processing chamber directly or through a vacuum trap.

In another aspect provided herein is a cartridge comprising: (i) a preprocessing chamber comprising an opening and, positioned in the opening, a tissue disruptor configured for mechanical disruption of tissue; (ii) a strain chamber comprising a strainer, wherein the strain chamber communicates with the preprocessing chamber; (iii) a first processing chamber communicating with the strain chamber; (iv) an optional second processing chamber communicating with the first processing chamber; (v) one or more cartridge ports communicating with the processing chamber and the second processing chamber if present.

In one embodiment, the cartridge further comprises: one or more waste chambers communicating with the first processing chamber and second processing chamber when present. In one embodiment, the first processing chamber comprises an element (e.g., a nozzle) configured to produce a hanging drop of liquid from the strain chamber.

In another aspect provided herein is a method of creating a microtissue comprising: (a) providing a cartridge of as described herein comprising a tissue; (b) disrupting the tissue with the tissue disruptor to produce a cell suspension; (c) straining the cell suspension with the strainer to produce strained cell suspension; and (d) forming a hanging drop from the strained cell suspension using the element. In one embodiment, the microtissue is an organoid. In another embodiment, the method further comprises: after forming the hanging drop, adding a liquid or gas to the processing chamber to support survival of the cells in the hanging drop.

In another aspect provided herein is a method of creating a microtissue comprising: (a) providing a cartridge of as described herein comprising a tissue; (b) disrupting the tissue with the tissue disruptor to produce a cell suspension; (c) straining the cell suspension with the strainer to produce strained cell suspension; (d) selecting stem cells from strained cell suspension; and (e) removing or growing the selected stem cells in the cartridge.

In another aspect provided herein is a method of creating a microtissue comprising: (a) providing a cartridge of as described herein comprising a tissue; (b) disrupting the tissue with the tissue disruptor to produce a cell suspension; (c) straining the cell suspension with the strainer to produce strained cell suspension; (d) differentiating cells from strained cell suspension into stem cells; and (e) growing or removing the differentiated stem cells in the cartridge.

In another aspect provided herein is a system comprising: (a) an instrument comprising: (i) one or more cartridge interfaces, each configured to engage a cartridge and comprising one or more fluid ports; (ii) a module comprising an actuator to actuate a tissue disruptor in a cartridge engaged with a cartridge interface (e.g., a mechanical, pneumatic, electromagnetic, or hydraulic actuator); and (b) one or more cartridges, each engaged with one of the cartridge interfaces, wherein each cartridge comprises: (i) a preprocessing chamber comprising an opening and, positioned in the opening, a tissue disruptor configured for mechanical disruption of tissue. In one embodiment the cartridge does not include any chambers other than the preprocessing chamber.

In another aspect provided herein is a cartridge comprising: (i) a preprocessing chamber comprising an opening and, positioned in the opening, a tissue disruptor configured for mechanical disruption of tissue.

In another aspect provided herein is a tissue disruptor comprising: (i) a sheath, (ii) a plunger configured to move slidably within the sheath and comprising a coupler to engage the actuator and a head for disrupting tissue, and (iii) a bias mechanism, e.g., spring, that biases the plunger toward a retracted position, i.e., wherein actuation is required to actuate the plunger to a forward position. In one embodiment, the sheath comprises a seater element adapted to seat the tissue disruptor on a seat. In another embodiment, the seater element comprises a flange adapted to sit on an annular ring. In another embodiment, the seater element comprises one or more tabs adapted to sit in one or more slots.

BRIEF DESCRIPTION OF THE DRAWINGS

The skilled artisan will understand that the drawings, described below, are for illustration purposes only. The drawings are not intended to limit the scope of the present teachings in any way.

FIG. 17 shows the reagent module with reagents loaded in an exemplary setup.

FIG. 18A shows an example of a single cell suspension of mouse kidney dissociated on the Singulator system. FIG. 18B shows an example of a nuclei suspension of mouse kidney dissociated on the Singulator system.

DETAILED DESCRIPTION OF THE INVENTION

Figure 1:
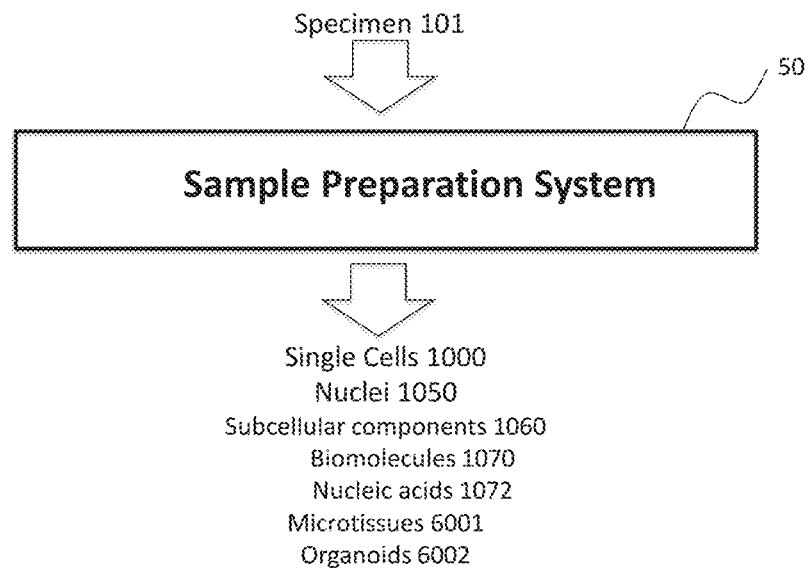
FIG. 1 shows a Sample Processing System that processes specimens or tissue specimens into biocomponents such as single cells or nuclei for bioanalysis.

NGS, mass spectrometry, FACS, and other modern high-throughput analysis systems have revolutionized life and medical sciences. The progression of information has been from the gross level of organism, to tissue, and now to single cell analysis. Single cell analysis of genomic, proteomic including protein expression, carbohydrate, lipid, and metabolism of individual cells is providing fundamental scientific knowledge and revolutionizing research and clinical capabilities.

Specimen: The term "specimen," as used herein, refers to an in vitro cell, cell culture, virus, bacterial cell, fungal cell, plant cell, bodily sample, or tissue sample that contains genetic material. In certain embodiments, the genetic material of the specimen comprises RNA. In other embodiments, the genetic material of the specimen is DNA, or both RNA and DNA. In certain embodiments the genetic material is modified. In certain embodiments, a tissue specimen includes a cell isolated from a subject. A subject includes any organism from which a specimen can be isolated. Non-limiting examples of organisms include prokaryotes, eukaryotes or archaebacteria, including bacteria, fungi, animals, plants, or protists. The animal, for example, can be a mammal or a non-mammal. The mammal can be, for example, a rabbit, dog, pig, cow, horse, human, or a rodent such as a mouse or rat. In particular aspects, the tissue specimen is a human tissue sample. The tissue specimen can be liquid, for example, a blood sample, red blood cells, white blood cells, platelets, plasma, serum. The specimen, in other non-limiting embodiments, can be saliva, a cheek, throat, or nasal swab, a fine needle aspirate, a tissue print, cerebral spinal fluid, mucus, lymph, feces, urine, skin, spinal fluid, peritoneal fluid, lymphatic fluid, aqueous or vitreous humor, synovial fluid, tears, semen, seminal fluid, vaginal fluids, pulmonary effusion, serosal fluid, organs, bronchio-alveolar lavage, tumors, frozen cells, or constituents or components of in vitro cell cultures. In other aspects, the tissue specimen is a solid tissue sample or a frozen tissue sample or a biopsy sample such as a fine needle aspirate or a core biopsy or a resection or other clinical or veterinary specimen. In still further aspects, the specimen comprises a virus, archae, bacteria, or fungus. The specimen can be an ex vivo tissue or sample or a specimen obtained by laser capture microdissection. The specimen can be a fixed specimen, including as set forth by U.S. Published Patent Application No. 2003/0170617 filed Jan. 28, 2003, or a FFPE specimen.

In some embodiments, the single cells can be analyzed further for biomolecules including one or more polynucleotides or polypeptides or other macromolecules. In some embodiments, the polynucleotides can include a single-stranded or double-stranded polynucleotide. In some embodiments, the polypeptide can include an enzyme, antigen, hormone or antibody. In some embodiments, the one or more biomolecules can include RNA, mRNA, cDNA, DNA, genomic DNA, microRNA, long noncoding RNA, ribosomal RNA, transfer RNA, chloroplast DNA, mitochondrial DNA, or other nucleic acids including modified nucleic acids and complexes of nucleic acids with proteins or other macromolecules.

It will be readily apparent to one of ordinary skill in the art that the embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

One version of tissue processing system is decribed in International patent application PCT/US2017/063811 filed Nov. 29, 2017 (WO 2018/102471) (Jovanovich, Chear, McIntosh, Pereira, and Zaugg, "Method and Apparatus for Processing Tissue Samples"), incorporated herein in its entirely for all purposes.

FIG. 1 shows a Sample Processing System 50 that can input specimen 101 and process them to produce biologicals such as single cells 1000 or nuclei 1050, microtissues 6001, organoids 6002, or other biocomponents comprised of subcellular components 1060, and biomolecules 1070 such as macromolecules 1071 and nucleic acids 1072, comprised of DNA 1073 and RNA 1074; proteins 1075; carbohydrates 1076; lipids 1077; biomolecules 1070 with multiple types of macromolecules 1071; metabolites 1078; and other biological components, including natural products 1079 for bioanalysis.

Figure 2:
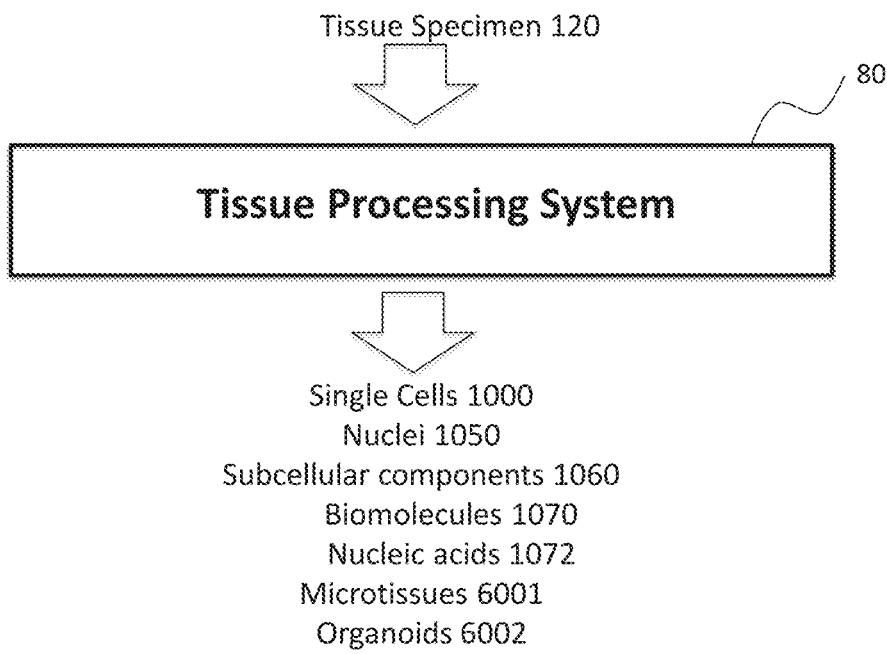
FIG. 2 shows a Tissue Processing System that processes tissue specimens into biocomponents such as single cells or nuclei or other for bioanalysis.

FIG. 2 shows a Tissue Processing System 80 that can input tissue specimens 120 and other specimens 101 and process them to produce biologicals such as single cells 1000 or nuclei 1050, microtissues 6001, organoids 6002, or other biocomponents comprised of subcellular components 1060, and biomolecules 1070 such as macromolecules 1071 and nucleic acids 1072, comprised of DNA 1073 and RNA 1074; proteins 1075; carbohydrates 1076; lipids 1077; biomolecules 1070 with multiple types of macromolecules 1071, metabolites 1078; and other biological components, including natural products 1079 for bioanalysis.

Figure 3:
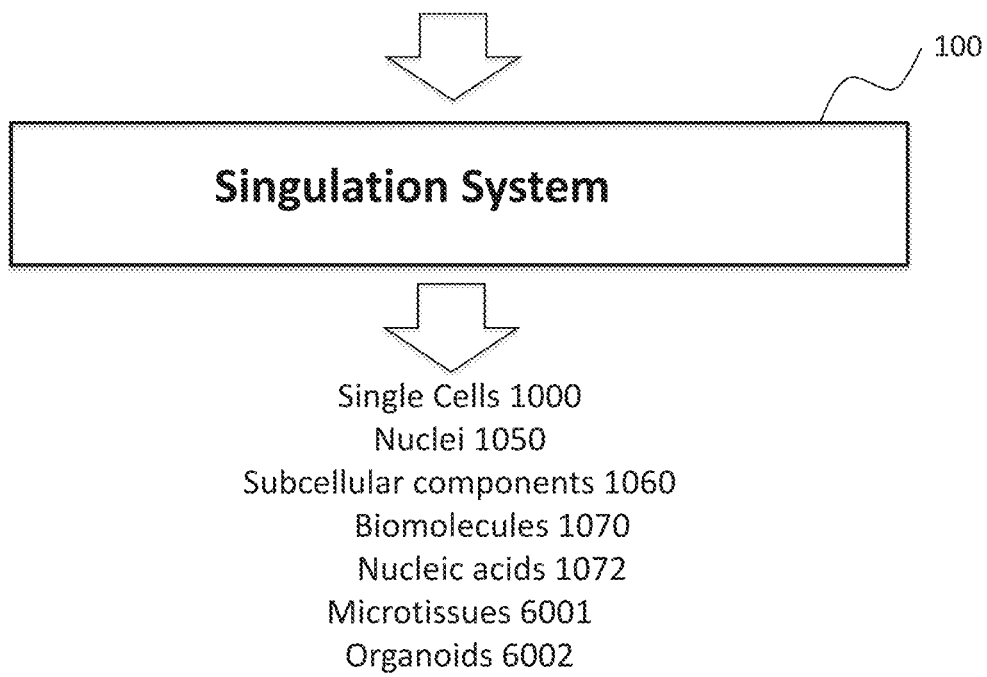
FIG. 3 shows a high level overview of the workflow for a Singulator System to generate for example single cell or nuclei or biomolecules from a specimen or tissue specimen.

Referring to FIG. 3, the Singulation System 100 accepts one or more specimens 101 or tissue specimens 120 and processes them to produce biologicals such as single cells 1000 or nuclei 1050, microtissues 6001, organoids 6002, or other biocomponents comprised of subcellular components 1060, and biomolecules 1070 such as macromolecules 1071 and nucleic acids 1072, comprised of DNA 1073 and RNA 1074 and single cell libraries 1200 for bioanalysis.

Figure 4:
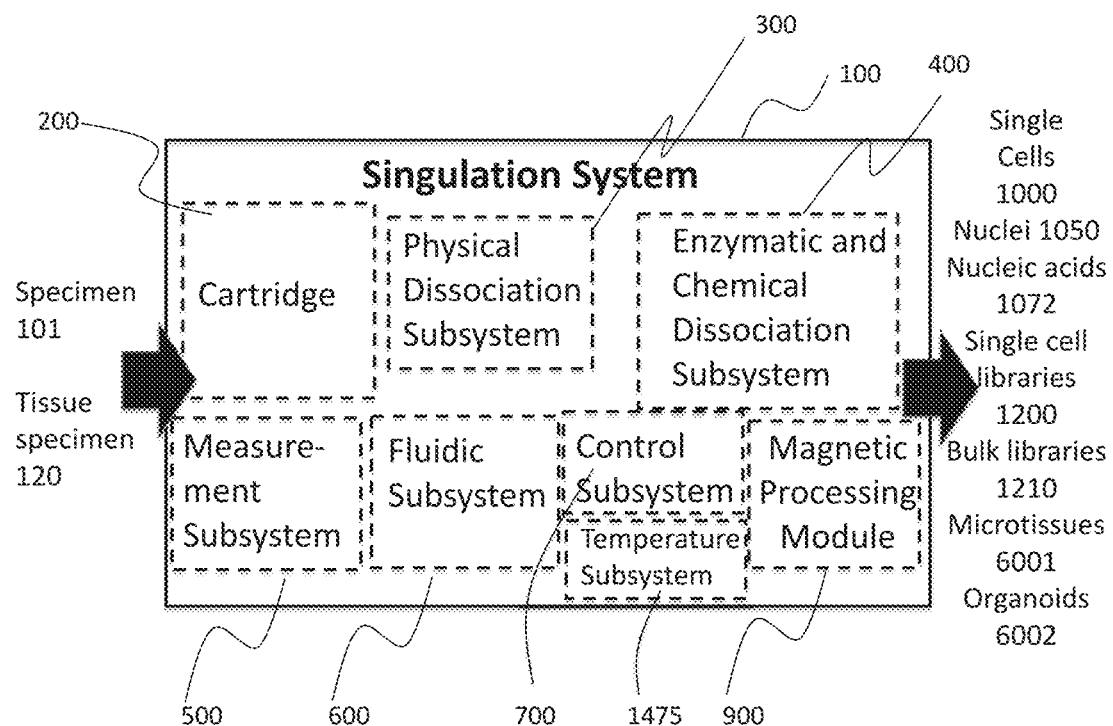
FIG. 4 shows an overview of an embodiment of the Singulator System and some exemplary modules. Tissue specimens or other specimens processed into single cells, nuclei, nucleic acids, single-cell libraries, microtissues, organoids and other biologicals through the use of one or more cartridges and one or more of the Physical Dissociation Subsystem, Enzymatic and Chemical Dissociation Subsystem, Measurement Subsystem, Fluidic Subsystem, Control Subsystem, or a Magnetic Module.

Referring to FIG. 4, in some embodiments, the Singulation System 100 processing is performed in cartridge(s) 200 in the system. Tissue specimens 120 or other specimens 101 are converted to single cells 1000, nuclei 1050, nucleic acids 1072, single cell libraries 1200, single nuclei libraries 1250, bulk libraries 1210, or other biocomponents comprised of subcellular components 1060, or biomolecules 1070 such as macromolecules 1071 and nucleic acids 1072, comprised of DNA 1073 and RNA 1074, or microtissues 6001, or organoids 6002 through the use of one or more cartridges 200 with one or more of the Physical Dissociation Subsystem 300, the Enzymatic and Chemical Dissociation Subsystem 400, the Measurement Subsystem 500, the Fluidic Subsystem 600, the Control Subsystem 700, Temperature Subsystem 1475, and the Magnetic Module 900.

The Physical Dissociation Subsystem 300 (which can include a preprocessing chamber, a tissue disruptor and an actuator) can perform physical disruption by passing the specimen through orifices, grinding, rotating a rotor with or without features to dissociate tissue, moving a head with or without features to dissociate tissue, forcing tissue through filters or screens or mesh or strainers, moving a pestle or Dounce like element, sonication, blending, homogenization, bead beating, pressure, and other methods known to one skilled in the art to physically disrupt tissue to help produce single cells or nuclei.

The Enzymatic and Chemical Dissociation Subsystem 400 (which can include or use a source of fluid (e.g., comprising one or more enzymes or chemicals) and portions of the fluidic subsystem and cartdrige interface that deliver liquids to a preprocessing or other chambers) can perform enzymatic disruption by adding formulations of a reagents or mixture of components comprised of but not limited to collagenases (e.g., collagenases type I, II, Ill, IV, and others), elastase, trypsin, papain, hyaluronidase, chymotrypsin, neutral protease, clostripain, caseinase, neutral protease (Dispose), DNAse, protease XIV, RNase inhibitors, DNAse inhibitors, or other enzymes, biochemicals, or chemicals such as EDTA, EGTA, protease inhibitors, buffers, acids, or base.

In another aspect, the Enzymatic and Chemical Dissociation Subsystem 400 can perform chemical disruption or chemical and enzymatic disruption is by adding formulations of chemicals that might disrupt tissue or cellular integrity such as Triton X-100, Tween, Nonident P40, other surfactants or detergents, digitonin, or biomolecules or chemicals that can dissociate tissue into cells or produce nuclei or other organelles directly from tissues or from single cell 1000 suspensions. Many different nuclei isolation solutions 412 have been developed, including NST buffer (146 mM NaCl, 10 mM Tris base at pH 7.8, 1 mM $CaCl_2$), 21 mM $MgCl_2$, 0.05% BSA, 0.2% Nonident P-40) (L. Martelotto, T Baslan, J, Kendall, F. C Geyer, K. A Burke, L. Spraggon, S. Piscuoglio, K. Chadalavada, G. Nanjangud, C. Ng, P. Moody, S. D'Italia, L. Rodgers, H. Cox, A. da Cruz Paula, A. Stepansky, M. Schizas, H. Y. Wen, T. A King, L. Norton, B. Weigelt, J. B Hicks, and J. S. Reis-Filho. Whole-genome single-cell copy number profiling from formalin-fixed paraffin-embedded samples. Nat Med. 2017 Mar. 23(3): 376-385. doi:10.1038/nm.4279.) or Homogenization buffer (10 mM Tris pH 8.0, 250 mM sucrose, mM KCl, 5 mM $MgCl_2$, 0.1% Triton-X 100, (v/v), 0.4 U/μL RNasin Plus RNase inhibitor (Promega), 1× protease inhibitor, 0.2 U/μL Superasin (ThermoFisher), 10 ng/mL Hoechst 33342, and 0.1 μM DTT) (Krishnaswami S R, Grindberg R V, Novotny M, Venepally P, Lacar B, Bhutani K, Linker S B, Pham S, Erwin J A, Miller J A, Hodge R, McCarthy J K, Kelder M, McCorrison J, Aevermann B D, Fuertes F D, Scheuermann R H, Lee J, Lein E S, Schork N, McConnell M J, Gage F H, Lasken R S. Using single nuclei for RNA-seq to capture the transcriptome of postmortem neurons. Nat Protoc. 2016 March, 11(3):499-524. doi: 10.1038/nprot.2016.015. PMID: 26890679.), or nuclear homogenization buffer (10 mM HEPES-KOH, pH 7.9, 25 mM KCl, 1 mM EDTA, 2 M sucrose, 10% glycerol, 0.15 mM spermine, 0.5 mM spermidine, 10 mM NaF, 1 mM orthovanadate, 1 mM PMSF, 0.5 mM DTT, and 1× protease inhibitor cocktail (Sigma)) (Ling G, Waxman D J. Isolation of nuclei for use in genome-wide DNase hypersensitivity assays to probe chromatin structure. Methods Mol Biol. 2013; 977:13-9.

doi: PubMed PMID: 23436350; PubMed Central PMCID: PMC3815455.) or 0.1× Lysis Buffer (1 mM TrisHCl, pH7.4, 1 mM NaCl, 0.3 mM MgCl2, Tween-20, 0.01% NonIdent P40, 0.001% digitonin, 0.1% bovine serum albumin) (Demonstrated Protocol—Nuclei Isolation from Mouse Brain Tissue for Single Cell ATAC Sequencing, Rev A, 10× Genomics) or 1×NIB: (10 mM MES-KOH (pH 5.4), 10 mM NaCl, 10 mM KCl, 2.5 mM EDTA, 250 mM sucrose, 0.1 mM spermine, 0.5 mM spermidine, 1 mM DTT. (S. Sikorskaite, M.-L. Rajamaki, D. Baniulis, V. Stanys and J. PT Valkonen. Protocol: Optimised methodology for isolation of nuclei from leaves of species in the Solanaceae and Rosaceae families. Plant Methods 2013, 9:31 http://www.plantmethods.com/content/9/1/31).

Similarly many different nuclei storage solutions 413 have been developed including Nuclei Wash and Resuspension Buffer (1×PBS with 1% BSA and 0.2 u/mL RNase Inhibitor (Sigma-Aldrich 3335399001)) (Demonstrated Protocol—Isolation of Nuclei for Single Cell RNA Sequencing, Rev B, 10× Genomics), or nuclear storage buffer (20 mM Tris-HCl, pH 8.0, 75 mM NaCl, 0.5 mM EDTA, 50% (v/v) glycerol, 1 mM DTT, and 0.1 mM PMSF) (Ling G, Waxman D J. Isolation of nuclei for use in genome-wide DNase hypersensitivity assays to probe chromatin structure. Methods Mol Biol. 2013; 977:13-9. doi: 10.1007/978-1-62703-284-1_2. PubMed PMID: 23436350; PubMed Central PMCID: PMC3815455.) or nuclear storage buffer (20% glycerol, 20 mM HEPES-KOH (pH 7.2), 5 mM $MgCl_2$, 1 mM DTT) (S. Sikorskaite, M.-L. Rajamäki, D. Baniulis, V. Stanys and J. PT Valkonen. Protocol: Optimised methodology for isolation of nuclei from leaves of species in the Solanaceae and Rosaceae families. Plant Methods 2013, 9:31 http://www.plantmethods.com/content/9/1/31) or NSB (166.6 mM sucrose, 5 mM $MgCl_2$, 10 mM Tris buffer, pH 8.0) (Krishnaswami S R, Grindberg R V, Novotny M, Venepally P, Lacar B, Bhutani K, Linker S B, Pham S, Erwin J A, Miller J A, Hodge R, McCarthy J K, Kelder M, McCorrison J, Aevermann B D, Fuertes F D, Scheuermann R H, Lee J, Lein E S, Schork N, McConnell M J, Gage F H, Lasken R S. Using single nuclei for RNA-seq to capture the transcriptome of postmortem neurons. Nat Protoc. 2016 March; 11(3):499-524. doi: 10.1038/nprot.2016.015. PMID: 26890679.).

In other embodiments, different reagents or mixtures of reagents are applied sequentially to dissociate the biological sample or specimen into single cells or nuclei. The physical and enzymatic/chemical dissociation and other subsystems can be separate from each other, or they can be co-located (e.g., acting upon the sample simultaneously or sequentially). The preprocessing, strain, and processing chambers can be separate from each other, or they can be co-located (e.g., acting upon the sample simultaneously or sequentially).

In some embodiments, the amount of dissociation is monitored at intervals during the dissociation or at the endpoint, and in some instances the viability is determined during processing using a Measurement Subsystem 500. The Measurement Subsystem 500 can be an optical imaging device to image cells using brightfield, phase contrast, fluorescence, chemiluminescence, near-field, Raman, or other optical readouts, or an optical measurement, or an electrical measurement, such as an impedance measurement of the change in conductivity, when a cell passes through a sensor, or thermal, or other types of measurement. In other embodiments Measurement Subsystem 500 can be a mass spectrometer, mass cytometer, or other system that determines mass.

The addition and movement of fluids can be performed by a Fluidic Subsystem 600. The Fluidic Subsystem 600 can use pumps, such as syringe pumps, piezopumps, electroosmotic pumps, peristalic pumps, on-cartridge pumps and valves, micropumps, pressure, pneumatics, or other components well known to one skilled in the art.

The Singulation System 100 can be controlled by software in a Control Subsystem 700 which can be comprised of a user interface 740 through a monitor, embedded display, or a touch screen 730. In some instances the Control Subsytem 700 can include interfaces to laboratory information management systems, other instruments, analysis software, display software, databases, email, and other applications. The Control Subsystem 700 can include control software 725 and scripts that control the operation and in some embodiments the scripts can be revised, created, or edited by the operator.

The Singulation System 100 can have temperature subsystem 1475 for temperature regulation that can set the temperature of various parts of the system such as at reagent storage, or in fluidic lines, or in cartridge 200. The temperature subsystem 1475 can use heating and or cooling from devices comprised of resistive heaters, Peltiers, circulating fluids, or other methods well known to one skilled in the art, with a temperature sensing element, such as a thermistor, thermocouple, thermoresponse color change, etc., and a temperature control board.

In another aspect provided herein is a device for the dissociation of a biological sample, the device comprising: (i) a biological sample or specimen 101; (ii) a cartridge 200 capable of dissociating tissue; (iii) an instrument to operate the cartridge 200 and provide fluids as needed (iv) a measurement module 500 such as an optical imaging to measure titer, clumping, and/or viability, or realtime PCR, (v) exchange of dissociation solution for buffer or growth media at the desired titer, and (vi) output vessels such as a chamber in the cartridge, 8 well strip tubes, microtiter plates, Eppendorf tubes, nanowells, or other vessels capable of receiving cell suspensions or an organoid 6002 or microtissue 6001.

In another aspect provided herein is a device for the dissociation of a biological sample and the production of single-cell 1000 or nuclei 1050 suspensions or matched bulk nucleic acids 1010 or single cell libraries 1200 or matched bulk libraries 1210, the device comprising: (i) a chamber or area to input a biological sample or specimen; (ii) a cartridge capable of dissociating tissue or specimen; (iii) an instrument to operate the cartridge and provide fluids as needed (iv) a measurement module such as an optical imaging to measure titer, clumping, and/or viability, or the quantity of one or more biomolecules 1070, (v) exchange of dissociation solution for buffer or growth media at the desired titer, (vi) the production of single-cell 1000 or nuclei 1050 suspensions or single cell libraries 1200, and matched bulk nucleic acid libraries 1210, in output vessels such as 8 well strip tubes, microtiter plates, Eppendorf tubes, a chamber in the cartridge, or other vessels capable of receiving cell suspensions.

Still referring to FIG. 4, a Magnetic Processing module 900 can use magnetic processing of magnetic and paramagnetic particles or surfaces or beads, referred to as beads, to separate single cells 1000, or cell types or nuclei 1050, or other biocomponents comprised of subcellular components 1060, and biomolecules 1070 such as macromolecules 1071 and nucleic acids 1072, comprised of DNA 1073 and RNA 1074; proteins 1075; carbohydrates 1076; lipids 1077; biomolecules 1070 with multiple types of macromolecules 1071; metabolites 1078; and other biological components, including natural products 1079 for bioanalysis. The magnetic processing module can introduce a magnetic field into parts of the cartridge, e.g., a processing chamber or other chamber or part of a chamber. This field can be used exert a magnetic force on magnetic and paramagnetic materials in the field, such as particles, such as beads, such as surfaces. Such particles can be sequestered from fluids in the chamber and, ultimately, separated from the fluids. In some embodiments the beads have a surface chemistry that facilitates the purification of the biologicals in conjunction with the chemical conditions. In other embodiments the bead have affinity molecules comprised of antibodies, aptamers, biomolecules, etc. that specifically purify certain biologicals such as cell types, organelles, nucleic acids 1072, nuclei 1050, or other components of tissue or samples.

In another aspect provided herein is a device for the dissociation and single-cell or single nuclei library preparation of a biological sample, the device comprising: (i) a chamber or area to input a biological sample or specimen; (ii) a cartridge 200 capable of dissociating tissue specimens 120 into single-cells 1000 or single nuclei 1050 and then producing single-cell libraries 1200 or single-nuclei libraries 1250; (iii) an instrument to operate the cartridge 200 and provide fluids as needed (iv) a measurement subsystem 500 such as an optical imaging to measure titer, clumping, and/or viability, (v) exchange of dissociation solution for buffer at the desired titer, (vi) a magnetic processing or other processing chamber or tubing to perform magnetic separations, normalizations, purifications, and other magnetic processes, for example, to purify nucleic acids, couple enyzmatic reactions such as library preparation reactions, and other processes including producing single-cells or nuclei in isolation, such as nanodrops, nanoboluses, or physical separation or solutions including agarose, polyethylene gycol, and other chemicals and materials that slow diffusion, (vii) output vessels such as 8 well strip tubes, microtiter plates, Eppendorf tubes, a chamber in the cartridge, or other vessels capable of receiving cell suspensions including nanowells.

In another embodiment, herein is a device and method for the dissociation of tissue into single cells which are then used to form microtissues 6001 or organoids 6002 on the cartridge 200 or the single-cells 1000 are used off the cartridge 200 to create microtissues 6001 or organoids 6002.

The basic elements of the Singulation System 100 can be configured in multiple ways depending on the specimen(s) 101 and analytes to be analyzed. In the following examples, a few of the numerous configurations are described in detail but in no way is the invention limited to these configurations as will be obvious to one skilled in the art. The Singulation System 100 can accommodate many different types of specimens 101, comprised of fresh tissue; snap-frozen tissue; microtome slices (cryo, laser or vibrating) of tissue; fixed tissue; FFPE; bulk material obtained by surgical excision, biopsies, fine needle aspirates; samples from surfaces, and other matrices.

There is a need to fill gap in the single-cell sample preparation for microtissues 6001 or organoids 6002 by starting the workflow at processing raw solid tissues into single-cell 1000 suspensions. The instant disclosure teaches how to produce a system that processes tissue specimens 120 and other samples into single cell 1000 suspensions nd then form microtissues 6001 or organoids 6002 with little or no intervention by the operator once the process is started. This requires adapting to the widely varying starting types of tissue, with different requirements depending on the tissue, species, age, and state. In some embodiments, the cells are used to isolate tumor infiltrating lymphocytes which can be characterized by sequencing or flow cytometery, or cultured with lymphokines such as interleukin-1 to produce therapeutic tumor infiltrating lymphocytes. The therapeutic tumor infiltrating lymphocytes can then be infused into the patient to lyse tumor cells and combat disease progression.

In the instant invention, many embodiments are possible and are incorporated by reference from patent application PCT/US2017/063811 filed Nov. 29, 2017 (Jovanovich, Chear, McIntosh, Pereira, and Zaugg, "Method and Apparatus for Processing Tissue Samples") and from provisional patent application 62/679,466 filed Jun. 1, 2018 (Jovanovich, "Method and Apparatus for Processing Tissue Samples); the contents of all are incorporated herein in their entirety as well as the number system used therein. Systems with increasing capabilites can be developed as a series of embodiments, six are described: two embodiment as a Single Sample Singulator System 2000, one as a Two Sample Singulator System 2200, a Four Sample Singulator System 2400, an Enhanced Singulator System 2500, and the Single Librarian 3000 embodiments.

This disclosure describes how to automate, integrate, and importantly standardize the complete process to create single-cell 1000 and then produce microtissues 6001 or organoids 6002 in a single Singulator System 100 system embodiment. The Singulator System 100 will greatly enable basic researchers, students, and translational researchers as well as clinicians and others with its ease of use and high performance.

Single-use cartridge designs.

Cartridges 200 can be used to process tissue into single-cell 1000 suspensions or nuclei 1050 and are preferrably single-use. The major workflow steps to produce single-cell suspensions 1000 for the production of microtissues 6001 or organoids 6002 is to first mechanically disrupt solid tissue by enzymatic dissociation, and straining to remove clumps.

Figure 5:
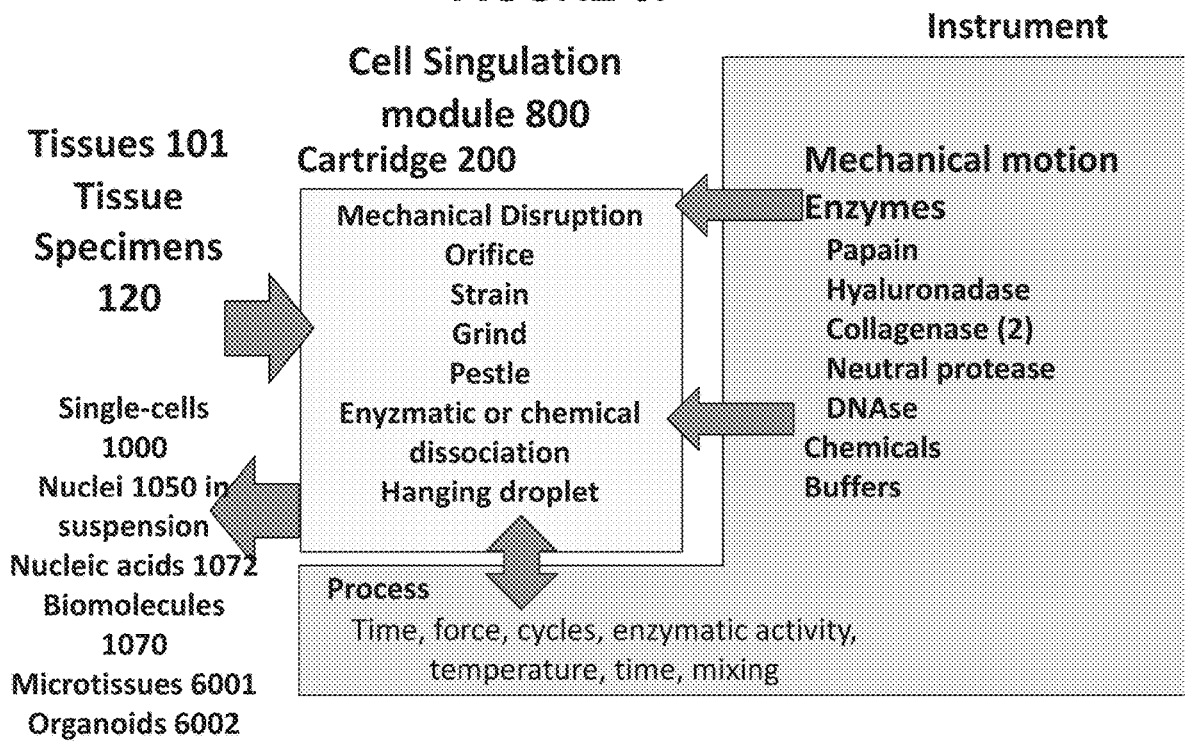
FIG. 5 shows the overall design concept of the Cell Singulation module for a prototype showing functional modules and a few example modalities of mechanical disruption and example enyzmatic formulation to dissociate solid tissue specimens into single cells, nuclei, and other biomolecules.
Figure 19A:
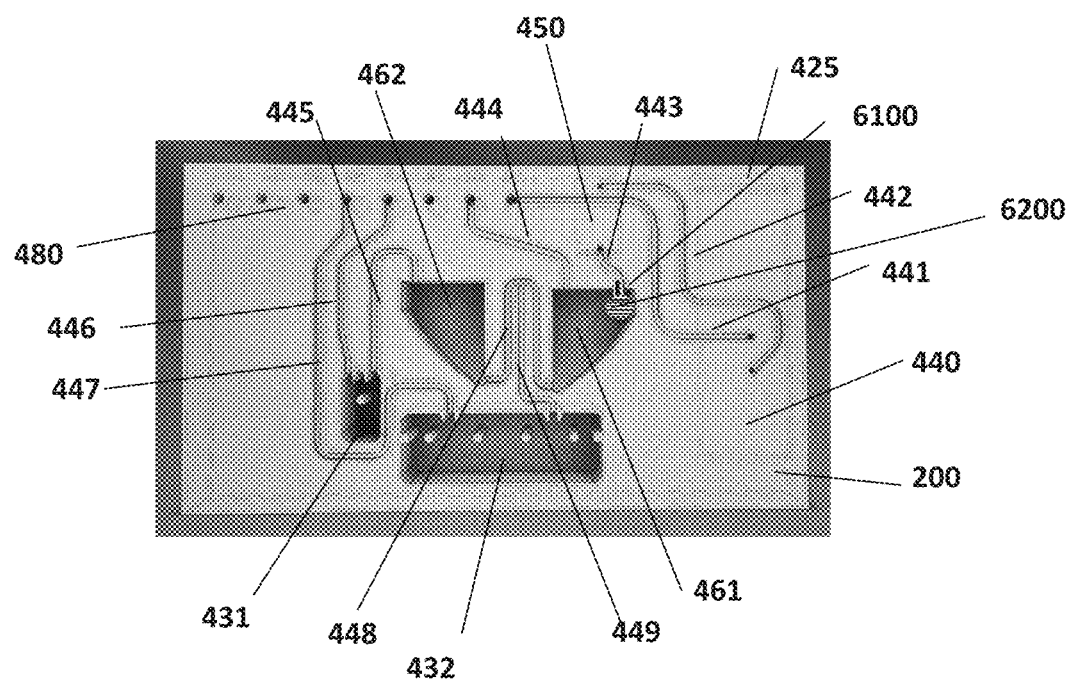
FIG. 19A shows an example of a vertical cartridge that integrates processing of tissue with the formation of an organoid by the hanging drop method and FIG. 19B is an illustration of the backside of the exemplary vertical cartridge.
Figure 19B:
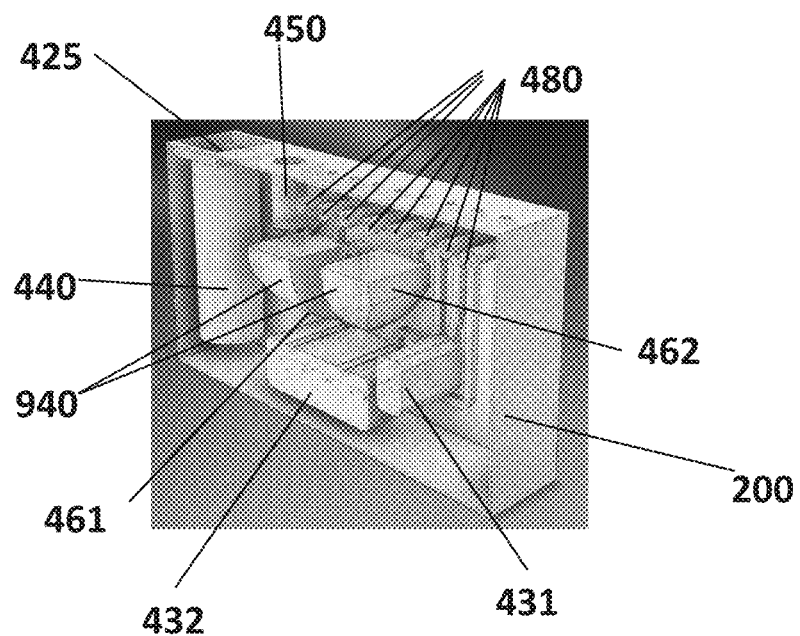
Figures 20, 21:
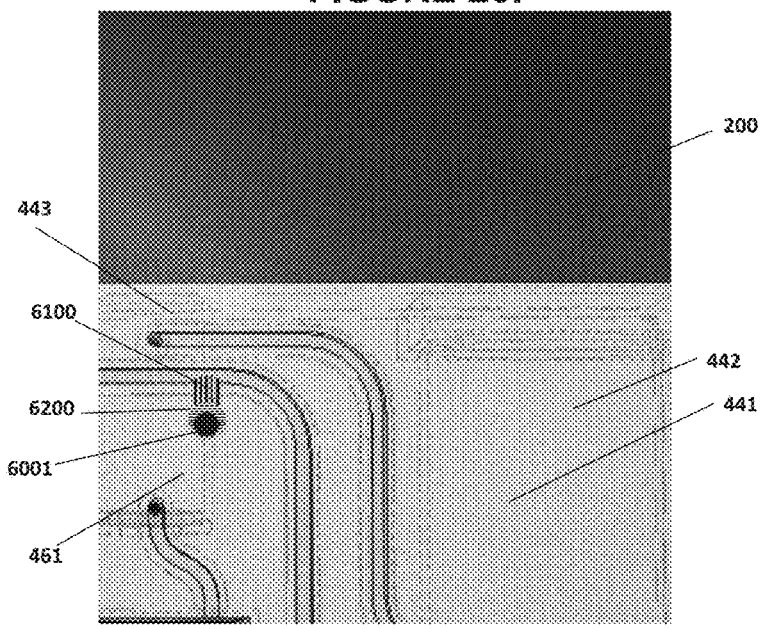
FIG. 20 shows a closeup of a vertical cartridge with a hanging droplet being formed on a noozle.
FIG. 21 shows a panel of genes useful in measuring stress induced gene expression changes.

Referring to FIG. 5, cartridge 200 will input specimen 101 and output viable singulated cells 1000 that are used to create microtissues 6001 or organoids 6002 or in some embodiments, as illustrated in FIGS. 19 and 20 by a hanging droplet 6200 in the cartridge 200. It is desirable that disposable cartridge 200 process multiple types of samples with mechanical disruption and enzymatic or chemical dissociation according to the tissue type and condition. The cartridge 200 can be designed to process tissue as quickly and as gently as possible, not expose the operator to the tissue being processed, and be manufacturable at low cost. Multiple mechanical methods may be needed to accommodate the wide range of tissues and their individual requirements: designs are shown that can be readily adapted to multiple different mechanical disruption methods comprising variable orifice 490, grinding with rotating plungers 336, pestles 361, and straining and filtering using a plunger 362 as well as other mechanical methods without limitation.

Cartridges 200 can be designed for 3D printing, injection molding in plastics with single or double pulls and low labor assembly, or layered assembly of fluidic and other layers, combinations of methods, and other methods well known to one skilled in the art. Fluids can be delivered to cartridge 200 by a syringe pump 2130 or can be preloaded onto cartridge 200 or many combinations. In some embodiments, flexible tubing 493 can connect chambers and creates simple pinch valves 491 to direct flow or can be used to create a peristaltic pump. In other embodiments, channels are created in the cartridge 200 and valves can be incorporated such as pneumatic valves, or other valves.

Singulator System Embodiment

In one embodiment of the Sample Processing System 50 as a Tissue Processing System 80, as shown in FIG. 2, the Singulator System 100 can perform powerful integrated tissue-to-genomics or sample-to-other answer (genomic, proteomic, metabolomic, or epigenetic, multi-omics, etc.) analysis functionality for scientists to simply and standardize the production and or analysis of single-cell 1000 or nuclei 1050 suspensions, affinity purified single cells 1100, affinity purified nuclei 1105, nucleic acids 1072, and bulk libraries 1210 from solid or liquid tissues. As will be obvious to one skilled in the art, the biological materials produced such as single cells 1000, nuclei 1050, nucleic acids 1072, single cell libraries 1200, single nuclei libraries 1250, bulk libraries 1210, or other biocomponents comprised of subcellular components 1060, or biomolecules 1070 such as macromolecules 1071 and nucleic acids 1072, comprised of DNA 1073 and RNA 1074, or microtissues 6001, or organoids 6002 can also be used for many genomic, cell biology, proteomics, metabolomics, and other analytical methods.

The Singulator System 100 can integrate the preparation of biological materials from liquid or solid tissue(s) with measurement subsystems 500 that perform an analysis selected from one or more of: DNA or RNA sequencing, next generation DNA or RNA sequencing, next next generation DNA or RNA sequencing of nucleic acids and their adducts such as epigenetic modifications; nanopore sequencing of nucleic acids and their adducts; single cell DNA sequencing of nucleic acids and their adducts; single nuclei RNA sequencing of nucleic acids and their adducts; PCR, digital droplet PCR, qPCR, RT-qPCR, genomic analysis, gene expression analysis, gene mapping, DNA fragment mapping; imaging including optical and mass spectrometry imaging; DNA or RNA microarray analysis; fluorescent, Raman, optical, mass spectrometery and other detection modalities of nucleic acids acids and their adducts with and without labels; proteomic analysis including fluorescent, Raman, optical, mass spectrometery, protein sequencing, and other detection modalities of proteins and peptides and their adducts and modifications with and without labels; carbohydrate characterization and profiling including sequencing, fluorescent, Raman, optical, mass spectrometery, and other detection modalities of carbohydrates and their adducts and other covalent polymers with and without labels; lipid characterization and profiling including sequencing, fluorescent, Raman, optical, mass spectrometery, and other detection modalities of lipids and their adducts and other covalent polymers with and without labels; flow cytometry; characterization of cells and profiling including fluorescent, Raman, optical, mass spectrometery, and other detection modalities of cells and their adducts and other covalent polymers with and without labels; metabolic profiling including sequencing, fluorescent, Raman, optical, mass spectrometery, and other detection modalities of metabolites and their adducts and other covalent polymers with and without labels; functional analysis including protein-protein interactions, protein-lipid interactions, protein-DNA interactions, RNA-DNA interactions, and other interactions between molecules derived from biological materials, with and without labels; bioinformatic analysis of cells, organelles, and biomolecules; and mass spectrometry and other analytical methods.

In this preferred embodiment a Cell Singulation module 800 and a Magnetic Processing module 900 are integrated into a Single-Sample Singulator System 2000 or into a Two-Sample Singulator System 2200 or a Four-Sample Singulator System 2400 or other Singulator system that processes more than four samples. Mechanical and enzymatic dissociation is performed in single-use cartridges 200 in one or more preprocessing chambers 440 to produce single-cell suspension 1000 or nuclei suspensions 1200, nucleic acids 1072, biomolecules 1070, subcellular components 1060, or other products from pre-processing. The samples can then be processed in the one or more processing chamber(s) 460 by optional bead-based affinity purification of cell types by surface antigens to produce affinity purified single-cell suspensions 1100 or nuclear suspensions by nuclear antigens 1105 or nucleic acids 1072, biomolecules 1070, subcellular components 1060 can be further processed into purified mRNA, NGS libraries, or other sample types. In some embodiments, one or more of the preprocessing 440 and processing chambers 460 and strain chambers 450 and vacuum trap chambers 468 and waste chambers 430 or other chambers can be combined.

In a preferred embodiment, a Single-Sample Singulator System 2000 was designed with reagents 411 on-board or in a reagent module 1430 adjacent to the Single-Sample Singulator instrument 2050 and with cartridges 200 incorporating one or more tissue-specific mechanical disruption modalities to accommodate the wide diversity of processing needs for tissue specimens 120. The system can input raw, unprocessed tissue samples and output single-cells 1000 or nuclei 1050 in suspension, ready for processing into single cell NGS libraries off device or can process the single cells 1000 or nuclei 1050 into bulk libraries on the system or perform analysis of the processed tissues.

Example: A Single-Sample Singulation System to Create Microtissues or Organoids

Figure 6:
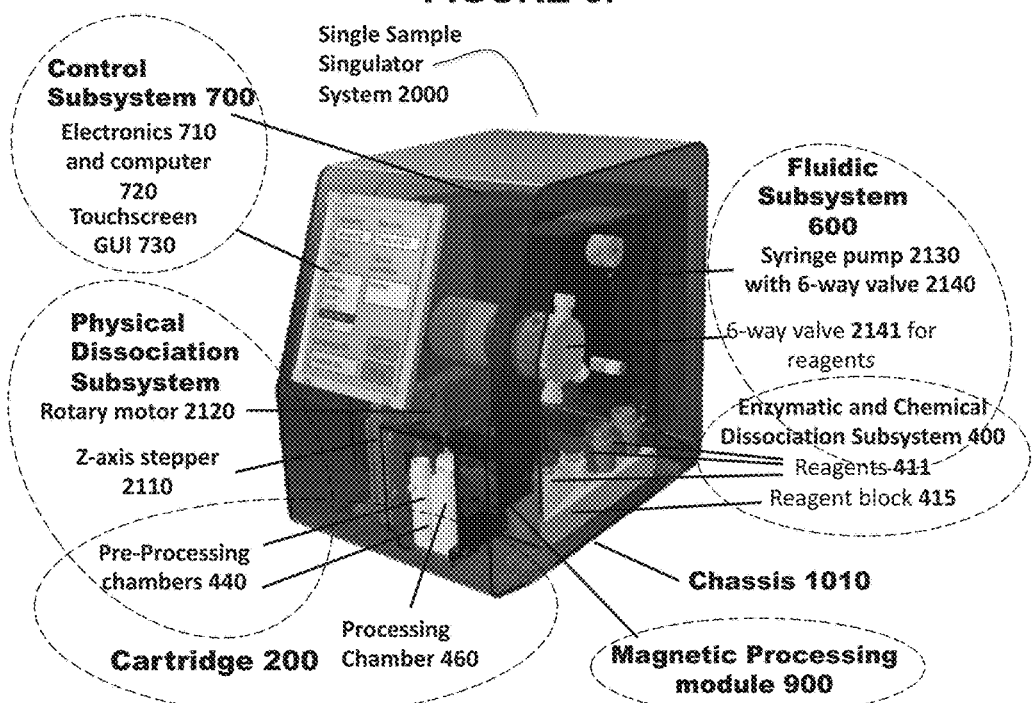
FIG. 6 shows an example of a Single-Sample Singulation System with mechanical disruption in a single cartridge with a bank of enzymes and reagents located in the instrument to dissociate solid tissue specimens into single cells, nuclei, and other biomolecules.

The Singulator System 100 can mechanically disrupt tissue and enzymatically dissociate the disrupted tissue in a cartridge 200 into single-cells 1000. As shown in the FIG. 5 in one embodiment, a Cell Singulation module 800 or, as shown in FIG. 6, a Single Sample Singulator System 2000 can combine the Physical Dissociation Subsystem 300 and the Enyzmatic and Chemical Dissociation Subsystem 400 to produce single-cell 1000 or nuclei 1050 suspensions. The instrument provides the mechanical motion and fluidics to the cartridge which in turn mechanically and enzymatically or chemically process the tissue into single cells 1000 or nuclei 1050. Multiple reagents 411 can be stored on the instrument or reagent module 1430 with cooling as needed. The single cell 1000 suspension can in turn be used to generate microtissues 6001 or organoids 6002.

The Cell Singulation module 800 as shown conceptually in FIG. 5 combines the mechanical disruption of specimen 101 on cartridge 200, adds enzymatic or chemical dissolution solution 410 and other fluids according to the protocols, and controls sample movement, pressures, and temperature. The Cell Singulation module 800 can move or rotate mechanical tissue disruptor elements comprised of without limitation a syringe plunger, pestle, Dounce pestle, or grinder, using a z axis stepper 2110 with a rotary motor 2120 coupled through the cap 210.

A 3D CAD representation of one embodiment of a Single-Sample Singulator System 2000 design packaged with a 'skin' is shown in FIG. 6 and another embodiment is shown in FIGS. 7, 8, 9, and 10. Both embodiments have a two axis mechanical motion (Z axis stepper 2110 and rotary motor 2120) integrated with fluidics based on a syringe pump, for example, with 1.6 µL resolution with a six-way valve (C2400MP, TriContinent) controlled by control software 725.

Referring to FIG. 6, a computer 720 with an operating system, for example, such as Windows 10 and 85 Gbytes H D (Beelink, AP42), can run control software 725 to control the system with display on a 10" touchscreen 730 (eleduino, Raspberry Pi10) or on a tablet 750. Chassis 1010 provides the framework to mount components and the exterior case of the system.

The embodiment of the Single-Sample Singulator System 2000 shown in FIG. 6 has a fluidic subsystem 600 with a single syringe pump 2130 with a single six-way valve 2140 to supply liquids, pressure, or vacuum to cartridge 200 from reagent block 415. In one embodiment, cartridge 200 has two preprocessing chambers 440 and a single processing chamber 460. In a preferred embodiment, magnetic processing module 900 can apply magnetic force to cartridge 200 under software control to enable the use of paramagnetic beads, paramagnetic surfaces, paramagnetic nanoparticles, and other magnetic or paramagnetic particles to purify and analyze single cells 1000, including stem and other types of cells, nuclei 1050, microtissues 6001, organoids 6002, nucleic acids 1072, biomolecules 1070, subcellular components 1060, or other products.

Figure 7:
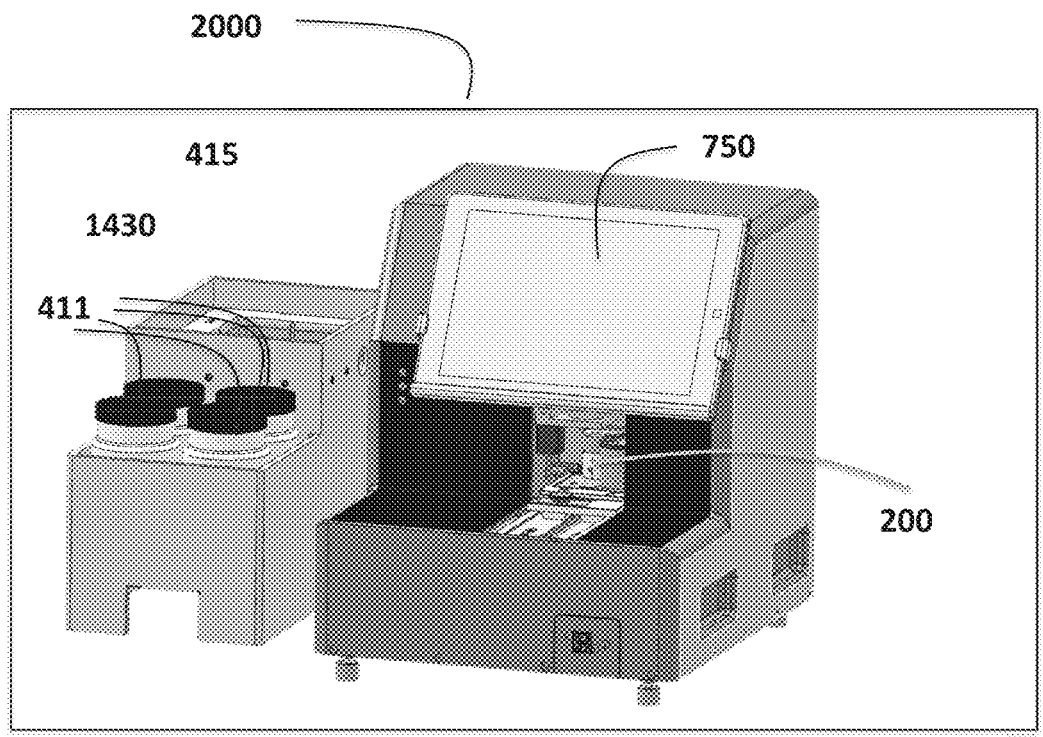
FIG. 7 shows another example of a Single-Sample Singulation System with mechanical disruption in a single cartridge with a bank of enzymes and reagents located separately from the instrument in a reagent module.

A preferred embodiment of the Single-Sample Singulator System 2000 with a case on is shown in FIG. 7. This embodiment has a reagent module 1430 which can be separate from Single Sample Singulator Instrument 2050 as shown in FIG. 7 with power and control provided by Single Sample Singulator Instrument 2050 or a separate power source and processor can be used or as shown in FIG. 6 reagent module 1430 be integrated inside a single instrument case.

Figure 8A:
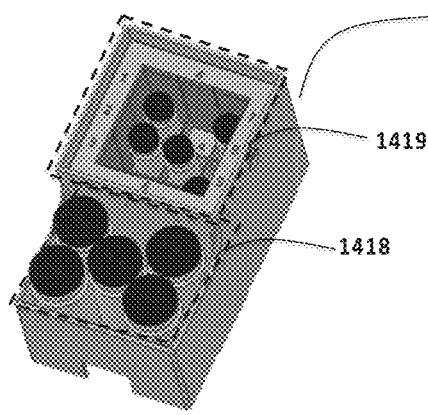
FIG. 8A and FIG. 8B shows an example of a reagent module for the Single-Sample Singulation System to dissociate solid tissue specimens into single cells, nuclei, and other biomolecules.

As shown in FIG. 8A, in a preferred embodiment reagent module 1430 has reagent Peltier 1420 attached to temperature distribution plate 1421. The temperature of reagent Peltier 1420 can be changed under control of computer 720 and control software 725 to heat or cool temperature distribution plate 1421 inside reagent storage chamber 1419 by monitoring temperature sensor 1417, which may be a thermocouple, or a thermistor, or optical detection of a thermochromic surface or other method. In a preferred embodiment, as shown in FIG. 8A, reagent Peltier 1420 maintains a set of reagents 411 at 4° C. in temperature-controlled reagent storage chamber 1419 and room temperature reagent storage chamber 1418 maintains a second set of reagents 411 at ambient temperature. It will be obvious to one skilled in the art that embodiments can have a one or more temperature controlled chambers containing one or more reagents.

Figure 8B:
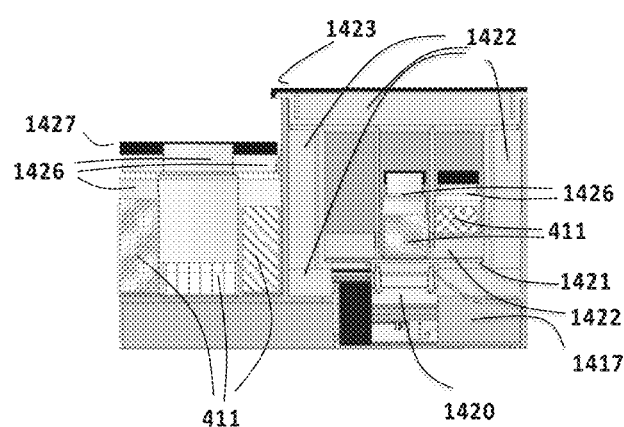

Referring to FIG. 8B, reagent storage chamber 1419 has insulation 1422 and lid 1423. Fluidic bundle 1424 fluidically connects syringe pump 2130 with reagent module 1430. In one embodiment, a power and control bundle 1425 from reagent Peltier relay board 2240 on Single Sample Singulator Instrument 2050 controls reagent Peltier 1420. In another embodiment, reagent module 1430 is powered by separately plugging into electrical power and reagent Peltier 1420 is controlled by a separate microprocessor, allowing reagent module 1430 to operate independently of Single Sample Singulator Instrument 2050 and is connected fluidically by fluidic bundle 1424 comprised of tubing such as 1/16 ID tygon tubing or other tubing, capillaries, microchip, or other fluidic vessels. In some embodiments, reagent container 1426 has reagent container lid 1427 contains one or more reagent container sensors 1428 to monitor the amount of reagent in the container, for example by weight, or by an phase interface using optics or other electromagnetic measurement methods, or by conductivity, or to determine the identity of reagent container 1426 by RFID, EEPROM, or other identification technologies. Information from reagent container sensor(s) 1428 can be stored in system log or be used to alert users to issues with reagent container sensor 1428 or other actions such as the need to changes reagents 411. In some embodiments, reagent container lid 1427 has one or more openings that may allow tubing or capillaries or fittings to be inserted or a hole with an optional filter. In a preferred embodiment, reagent module 1430 has reagent Peltier exhaust duct 1417.

Figure 9:
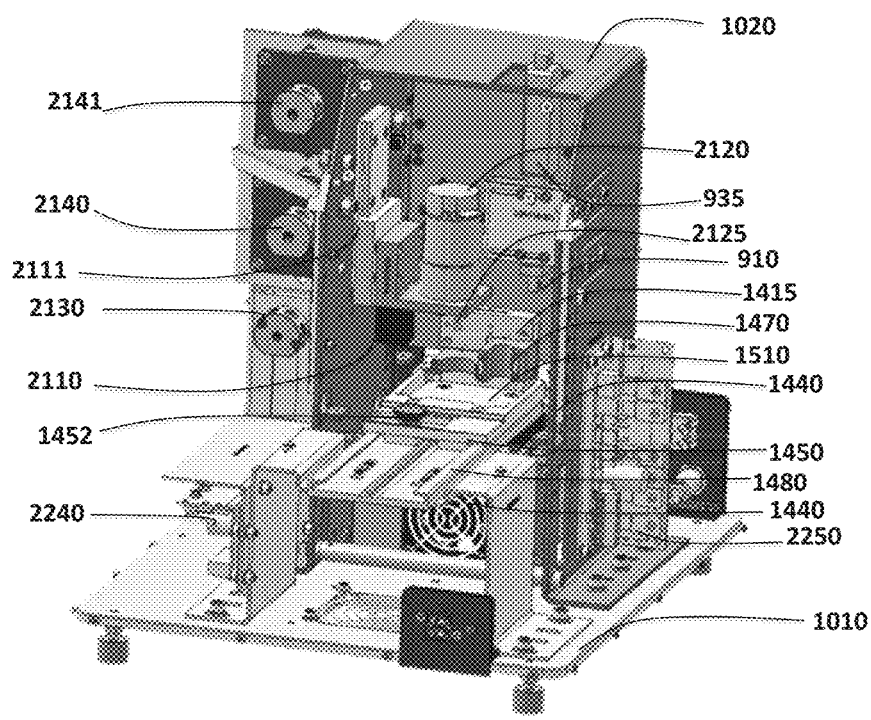
FIG. 9 shows the front of an example of the Single-Sample Singulation System to dissociate solid tissue specimens into single cells, nuclei, and other biomolecules using a cartridge.

Referring to FIG. 9, in a preferred embodiment, Single Sample Singulator Instrument 2050 has z-axis stepper motor 2110, which may have an optional encoder, that controls the vertical position of rotary motor 2120 mounted on z-axis stepper slide 2111 attached to the inverted 'U' shaped structural frame 1020 mounted on chassis 1010. A force gauge can be incorporated into the z-stage stepper 2110 to provide force-feedback control of the mechanical force on the specimen 101; this can help ensure very gentle mechanical processing steps. Syringe pump 2130 connects fluidically with tubing or capillaries or microchips or other fluidic connectors with six-way valve 2141 and six-way valve 2142 to supply reagents, pressure, or vacuum to cartridge 200 (not shown) from reagent module 1430.

Cartridge 200 is placed into cartridge receiver tray 1510 on cartridge slide 1450 which is designed to hold cartridge 200 precisely, with the center of preprocessing chamber 440 concentric with the center of rotary motor shaft 2121 of rotary motor 2120 within a distance or 1 or, 5, or 10, or 15, or 20, or 25, or 50, or 100, or 250 µm, or more when inserted by moving cartridge 200 in cartridge receiver tray 1510 on cartridge slide 1450 on cartridge slide rail 1480 until spring-loaded cartridge slide knob 1452 locks into place into a hole in cartridge slide 1450 with cartridge 200 held in place near or in contact with the thermal transfer plate 1470 and making fluidic connections with the pogo pins 1415 of cartridge interface 1500.

The temperature regulating subsystem 1475 can set the thermal transfer plate 1470 to a given temperature by cartridge Peltier 1440 or other temperature regulating device such as strip resistive heaters, circulating fluids, etc. to set the cartridge temperature in the preprocessing chamber 440 and processing chamber 460 under control of board 2250. In some embodiments, the temperature of the preprocessing chamber 440 and processing chamber 460 can be set independently.

In a preferred embodiment, fluidic ports on cartridge 200 dock with spring-loaded pogo pins 1415 to connect fluids, gases, or vacuum to cartridge 200 on cartridge insertion. In another embodiment, pogo pins 1415 or cannula 1416 are moved to connect with cartridge 200 after cartridge insertion. In another embodiment, cannula 1416 connected to fluidic lines from syringe pump 2130 are held rigidly attached to the thermal transfer plate 1470 or other part of instrument and cartridge 200 has flexible materials on cartridge ports that seal with the cannula(s) 1416 after cartridge insertion, as described below. Cartridge ports are ports opening out of a cartridge. A cartridge port may communicate directly with a chamber by being a port in the chamber, or indirectly. e.g., through another chamber comprising the port and communicating with the chamber in question.

The embodiment of the single-sample Singulator System 2000 shown in FIG. 9 has a Magnetic Processing Module 900 and magnet 910 is moved by magnetic actuator 935 mounted on inverted 'U' shaped structural frame 1020 under control of control software 725 using controller 2122. Magnet 910 can be far from cartridge 200 as shown in FIG. 9 and not interact with any magnetic beads 685 in cartridge 200 or in an extended position magnet 910 is moved to be near cartridge 200 for magnetic capture and processing of magnetic beads 685.

Figure 10:
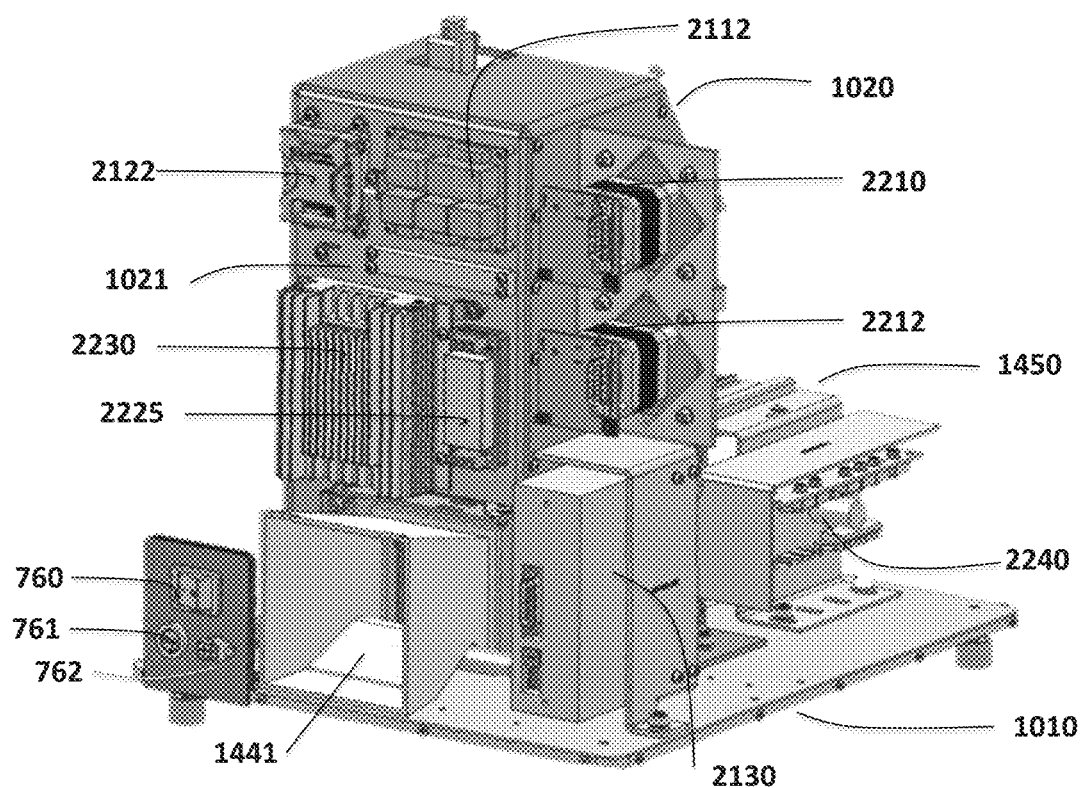
FIG. 10 shows the back of an example of the Single-Sample Singulation System.

Referring to FIG. 10, in a preferred embodiment, the Single-Sample Singulator System 2000 has a back structural frame 1021 on structural frame 1020 that mounts electronics 710 comprising rotary motor controller 2122, z-axis stepper controller 2112, 24 V to 5 V step down power supply 2230 and 24 V to 12 V step down power supply 2225. Power can be supplied to single-sample Singulator System 2000 by plugging a 24 V power supply into plug 762 connecting to fuse 761 and power switch 760. Six way valves 2141 and 2142 are controlled by boards 2210 and 2212. Reagent Peltier relay board 2240 can control reagent Peltier 1420.

Figure 11:
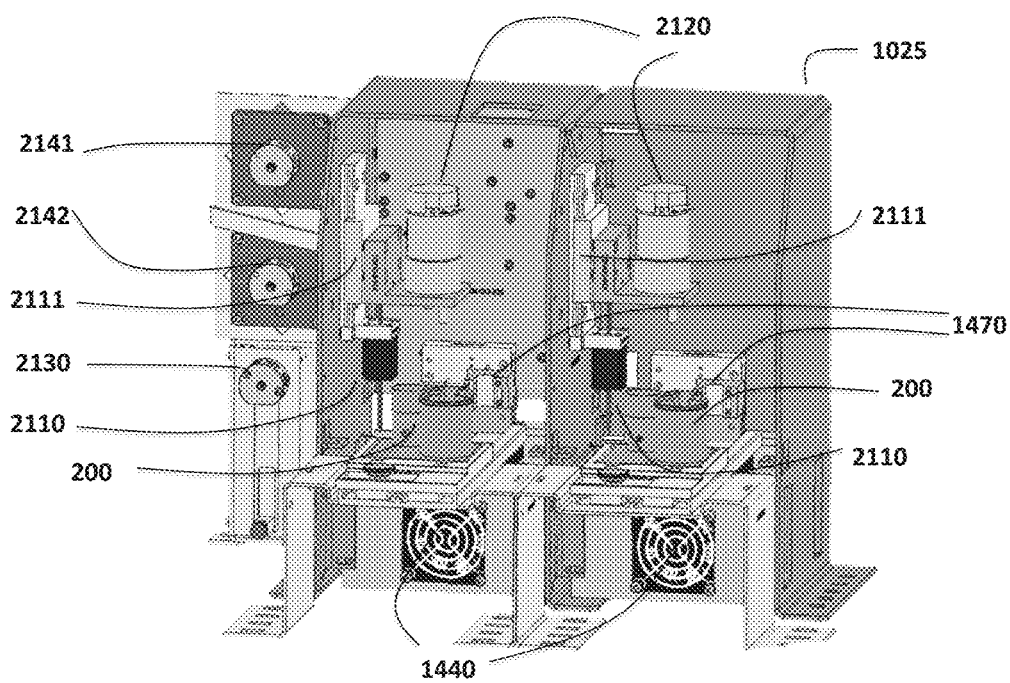
FIG. 11 shows an example of a two sample Singulation System to dissociate solid tissue specimens into single cells, nuclei, and other biomolecules using a two cartridges.

Singulator systems that process one or more cartridges simultaneously are within the scope of the present invention. FIG. 11 illustrates a Two Sample Singulator instrument 2200 that can process two specimens 101 in two cartridges 200. The embodiment shown in FIG. 11 has two z-axis stepper motors 2110 that independently controls the vertical position of two rotary motors 2120 mounted on two z-axis stepper slides 2111 attached to the inverted 'M' shaped structural frame 1025 mounted on chassis 1010. Syringe pump 2130 connects fluidically with tubing or capillaries or microchips or other fluidic connectors with six-way valve 2141 and six-way valve 2142 to supply liquids, pressure, or vacuum to cartridges 200 from reagent module 1430 (not shown) through pogo pins 1415 (not shown) mounted above thermal transfer plate preprocessing chamber 440 and processing chamber 460. A third 6 way valve (not shown) can provide fluids to the second cartridge interface 1500.

The cartridge 200 can have one or more Pre-Processing Chamber(s) 440 and none, one, or more Processing Chamber(s) 460 as well as none, one or more other chambers such as cartridge waste chamber 435 or vacuum trap chamber 468.

Figure 12:
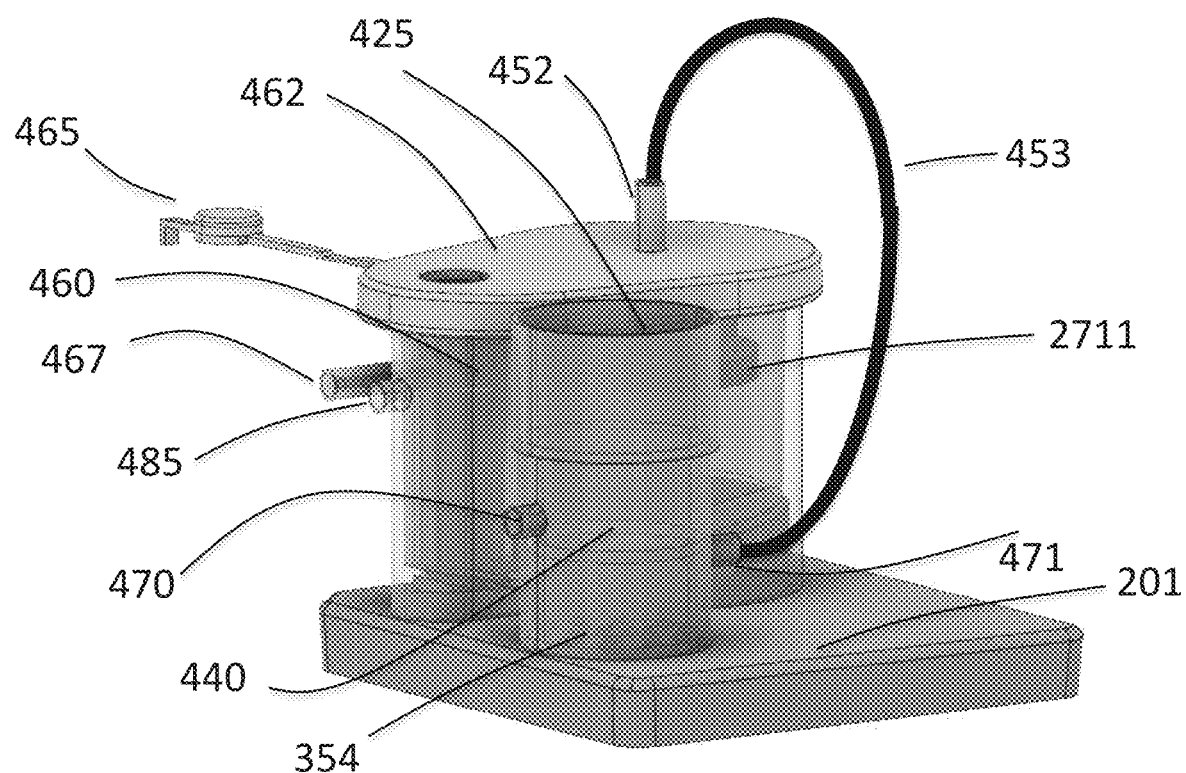
FIG. 12 shows an example of a cartridge with preprocessing, processing, and vacuum trap chambers for processing solid tissue specimens into single cells, nuclei, and other biomolecules.

In a preferred embodiment, illustrated in FIGS. 12 and 13, cap 210, alternatively referred to as a tissue disruptor, is placed on top of preprocessing chamber 440 after specimen 101 or tissue specimen 120 is added through sample inlet port 425 into preprocessing chamber 440 of cartridge 200. After cartridge 200 is inserted into the instrument, pogo pins 1415, cannula 1416, or other fluidic connectors can connect with none, one, or more of cartridge ports 470 to supply reagents to preprocessing chamber 440, cartridge port 485 to supply reagents or vacuum to processing chamber 460, and cartridge vacuum trap port 467 to supply vacuum to vacuum trap chamber 468.

A preferred embodiment illustrated in FIG. 12 fluidically connects preprocessing chamber 440 to processing chamber 460 using fluidic line 453, which can be tubing, connecting from preprocessing chamber nipple 471 to lid nipple 452 positioned over strainer 2711 inserted into processing chamber 460, eliminating the need for a separate strain chamber 450. In other embodiments, strainer 2711 can be incorporated as an in-line filter, for example in a swinney filter holder 347 attached to the output of preprocessing chamber 440 or in fluidic line 453 or attached to lid 462. Lid 462 produces a vacuum tight seal of processing chamber 460 and vacuum trap chamber 468 when cap 465 is closed onto lid 462, and can be attached to cartridge body 201 by ultrasonic welding, glue, epoxy, adhesives, and other methods to produce a vacuum tight seal and prevents changing strainer 2711 ensuring single usage of cartridge 200.

In some embodiments, cartridge 200 can have on-cartridge valves which can be pinch valves 491 on fluidic lines such as fluidic line 453 which the instrument actuates to open and close lines, or by using a 'T' junction and two lines, rout fluids down different paths such as to a optics imaging system 520. In another embodiment, fluidic lines such as fluidic line 453 can be partially closed to create a variable orifice 2160 that can disrupt partially dissociated tissue. Actuators can open and pinch close tubing in the cartridge 200, or operate the variable orifice 2160 using variable orifice device 2150 when desired. In other embodiments, cartridge 200 can have on-cartridge valves which can be miniaturized pneumatic valves, or microvalves. In some embodiments, microfluidics or microchips are used for fluidic lines. In a preferred embodiment there are no valves on the cartridge 200 with all fluidic control from the instrument.

Figure 13A:
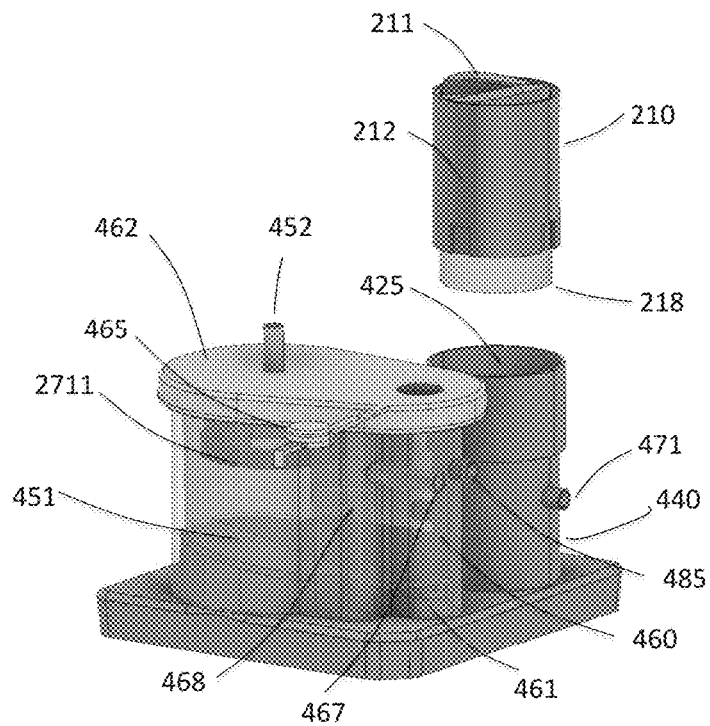
FIG. 13A-13C show an example of a cap with a cartridge with a preprocessing, processing, and vacuum trap chambers for processing solid tissue specimens into single cells, nuclei, and other biomolecules and details of the assembly of the cap.

Referring to FIG. 13A, when vacuum is applied to vacuum trap port 467 or to reagent port 485, liquids including single cell suspensions 1000, nuclei 1050, and other subcellular components 1060, and biomolecules 1070 are pulled from preprocessing chamber 440 through fluidic line 453 and strainer 2711 into strain drain 451 and into output collector region 461 of processing chamber 460. Strainer 2711 can have pore sizes such as 2, 5, 10, 15, 20, 25, 30, 40, 50, 70, 100, 125, 200 µm, or larger to filter the suspension of biological material. Multiple in-line or stacked strainers 2711 can be employed to successively remove different sized components of the dissociated tissue specimen 110. Cap 210 with cap coupler 211, and head 218 is shown ready to be inserted into sample inlet port 425. Head 218 can have a surface for disrupting tissue that can comprise raised features 355 that aid in mechanically disrupting a tissue, organ, microtissue 6001, organoid 6002 or other biological material.

Figure 13B:
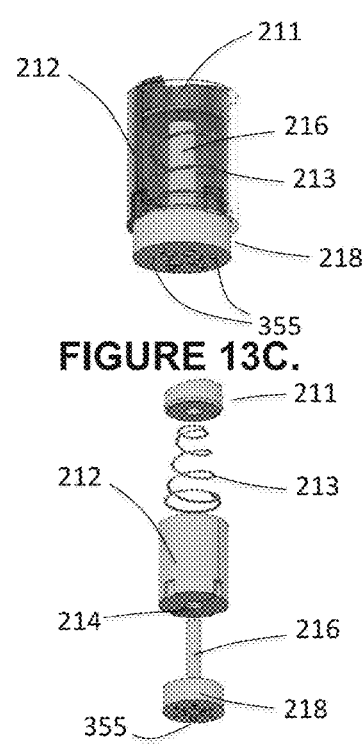
Figure 13C:
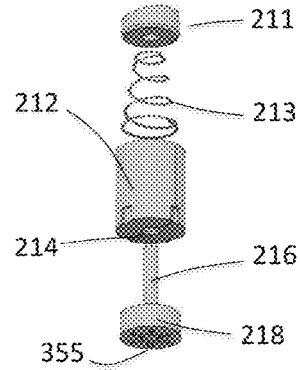

Referring to FIG. 13B and FIG. 13C, the cap coupler (also referred to as "drive head") 211 is held inside cap sheath 212 which in one embodiment has cap sheath hole 214. Cap coupler 211 is attached to cap shaft 216 which passes through cap sheath hole 214 and is attached to the head 218 which can be a rotor 353 with grinding teeth 355. The assembly of cap coupler 211 attached to cap shaft 216 and head 218 are referred to as a plunger 336 which is a type of moveable mechanical tissue disruptor 345.

Figure 14A:
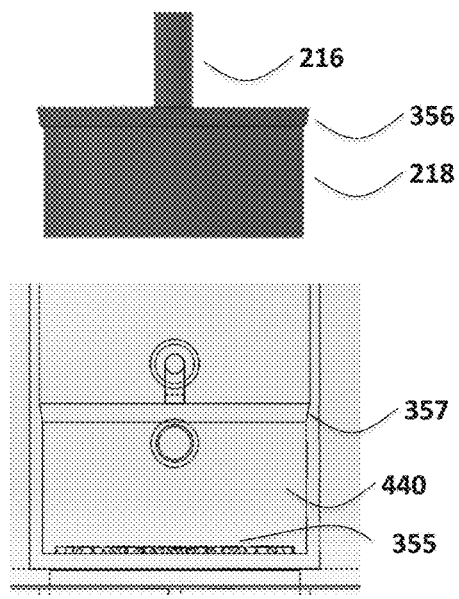
FIG. 14A-14B shows an example of a tissue disruptor with a feature designed to center the head of the disruptor in a preprocessing chamber and set the bottom gap and side gaps between the disruptor head and the wall of the preprocessing chamber.
Figure 14B:
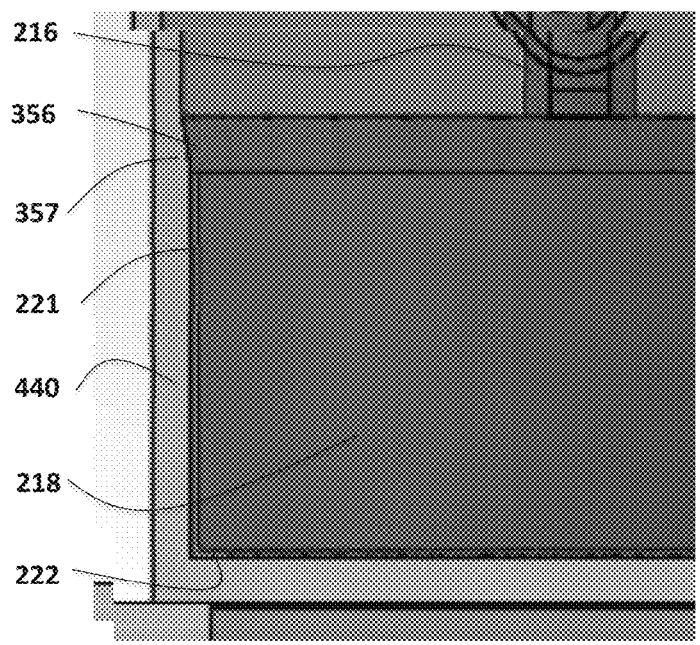
Figure 15A:
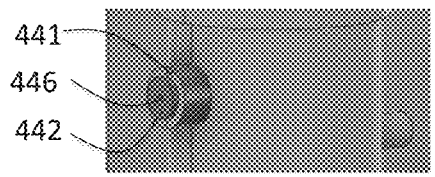
FIG. 15A-15D show a port cover with low durometer over a port secured by a port cover retaining cylinder, or a crimp, or a heat staked port cover retaining cylinder.
Figure 15B:
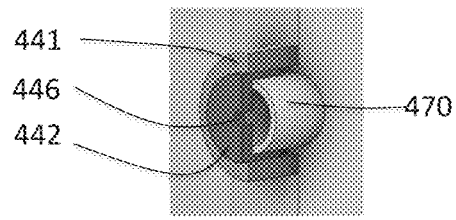
Figure 15C:
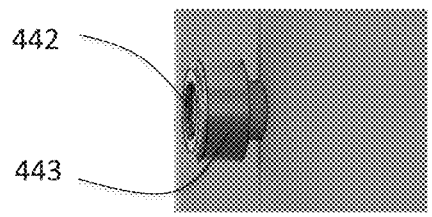
Figure 15D:
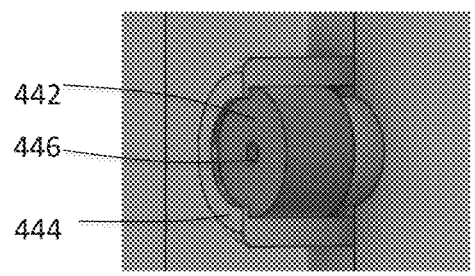

Referring to FIG. 14A, in a preferred embodiment, head 218 attached to cap shaft 216 has a outwardly annular beveled head feature 356 designed to improve centricity of head 218 inside preprocessing chamber 440 and thereby the uniformity of side gap 221 at the bottom of travel. When z-axis stepper motor 2110 lowers and cap coupler 211 is pushed down by rotary motor coupler 2125, head 218 will lower until outwardly annular beveled feature 356 engages with inwardly annular beveled preprocessor chamber feature 357 on the inside wall of preprocessing chamber 440 to produce a centered head 218 as shown in FIG. 14B. The centering of head 218 will produce a uniform side gap 221 between head 218 and the inner wall of preprocessing chamber 440. In addition, if the height of head 211 is less than the height of the preprocessing chamber 440 below inwardly beveled feature 357, the engagement of outwardly annular beveled head feature 356 with inwardly annular beveled preprocessor chamber feature 357 will set a uniform bottom gap 222. The size of the side gap and the bottom gap can be optimized for different cell types or for different sized nuclei or subcellular organelles, or multicellular structures such as intestinal crypts. In addition, to allow passage of disrupted tissue when head 218 is seated on inwardly annular beveled preprocessor chamber feature 357, the inwardly annular beveled preprocessor chamber feature 357 can be fluted to have sections with the same or different depths. The side gap 221 between the head 218 of moveable mechanical disruptor 345 and the inside wall is preferrably greater than or equal to 1 µm, or 2 µm, or 5 µm, or 10 µm, or 15 µm, or 20 µm, or 25 µm, or 30 µm, or 40 µm, or 50 µm, or 75 µm, or 100 µm, or 150 µm, or 200 µm, or 250 µm, or 500 µm, and 1000 µm or more, as well as any size in between. The bottom gap 222 between the bottom of head 218 of moveable mechanical disruptor 345 and the bottom of preprocessing chamber 440 is preferably greater than or equal to 1 µm, or 2 µm, or 5 µm, or 10 µm, or 15 µm, or 20 µm, or 25 µm, or 30 µm, or 40 µm, or 50 µm, or 75 µm, or 100 µm, or 150 µm, or 200 µm, or 250 µm, or 500 µm, and 1000 µm or more, as well as any size in between. In some embodiments, different heads can be selected to be used with the same diameter preprocessing chamber 440 to produce different side gaps 221 or bottom gaps 222 to simplify manufacturing and inventory management requirements. A bottom gap between a flat surface of the head and the flat bottom surface of the preprocessing chamber can also be limited by the position of the flutes, or half domes, or other structures that prevent or define gaps between a flat surface of the head and the flat bottom surface of the preprocessing chamber.

Referring to FIG. 15, none, one, or more of the ports to cartridge 200 can have flexible or low durometer port covers 442, for example without limitation 40 to 100 durometer. As illustrated in FIG. 15A and in cutout FIG. 15B, port cover 442 can be inserted into the space between the port and port cover retaining cylinder 441 to secure the port cover 442 in place over, for example as shown, reagent addition port 470. A fluidic cannula 1416 or fluidic pogo pin 1415 with an outside diameter larger than port cover center hole 446 can engage the port covered by port cover 442 and, because of the relatively low durometer, the port cover 442 will be deformed by fluidic cannula 1416 or fluidic pogo pin 1415 to create a seal around the fluidic cannula 1416 or fluidic pogo pin 1415. In some configurations, the deformation can be used to eliminate the need for springs and the use of the fluidic pogo pin 1415 can be replaced by a non-movable fluidic cannula 1416. FIG. 15C shows port cover 442 retained by crimp seal 443. FIG. 15D shows port cover 442 retained by forming port cover retaining cylinder 442 higher than the port cover 442 and melting the port cover retaining cylinder 442 to form a heat stake lip 444 that retains port cover 442.

Figure 16A:
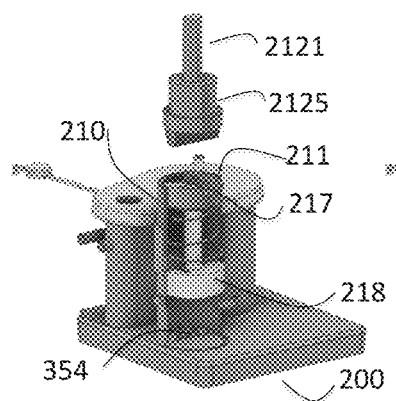
FIG. 16A-16E shows a cap engaging with a rotor motor adaptor and with a cartridge with a preprocessing, processing, and vacuum trap chambers for processing solid tissue specimens into single cells, nuclei, and other biomolecules.
Figure 16B:
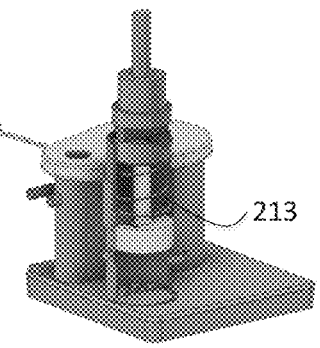
Figure 16C:
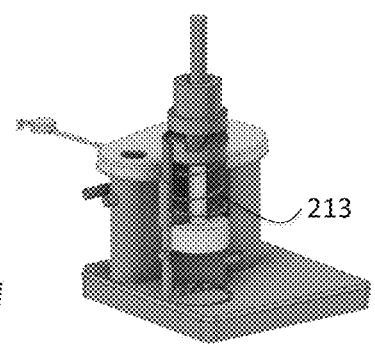
Figure 16D:
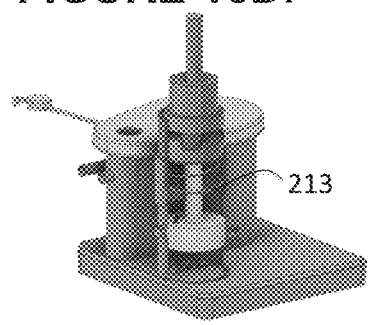
Figure 16E:
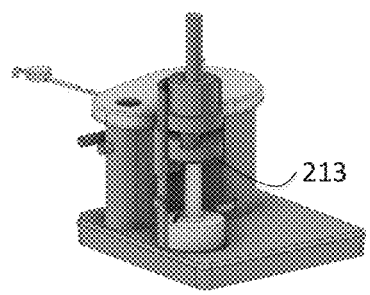

In a preferred embodiment the Single Sample Singulator Instrument 2050 has an actuator for mechanical processing that has a stepper motor 2110 that controls the vertical position of rotary motor 2120 and rotary motor shaft 2121 attached to rotary motor coupler 2125 that in turn can mechanically couples with cap coupler 211 of the cap 210 when inserted into cartridge 200. The coupler can have a drive head that takes any appropriate form, such as a slot, a phillips head, a quadrex, atri-wing, aspanner or a hex. Rotary motor coupler 2125 has one or more facets that reversibly engage cap coupler 211 by actions such as moving downward and slowly rotating. As shown in FIG. 16A, in a preferred embodiment, rotary motor coupler 2125 has a single blade to engage cap coupler 211 in cap 210. As shown in the cutaway in FIG. 16 B, when stepper motor 2110 lowers, the rotary motor coupler 2125 attached to rotary motor shaft 2121 engages cap coupler 211 in cap 210 and if the rotary motor coupler 2125 is not lined up with cap coupler groove 217, the rotary motor coupler 2125 can not directly insert into the cap coupler groove 217. In a preferred embodiment, cap coupler 211 has two surfaces on either side of cap coupler groove 217 which slope in opposite directions across the cap coupler 211 such that each side has a higher and lower wall on either side of cap coupler groove 217. When rotary motor shaft 2121 turns in the dockside direction (looking from above), rotary motor coupler 2125 blade spins in the dockside direction and encounters the high side of the wall of cap coupler groove 217 and begin to rotate cap coupler 211 clockwise. As stepper motor 2110 lowers, the rotary motor coupler 2125 will engage the cap coupler groove 217, as shown in FIG. 16C. As shown in FIG. 16D, when stepper motor 2110 continues to lowers, the rotary motor 2120 and rotary motor shaft 2121 attached to rotary motor coupler 2125 will lower, pushing on cap coupler groove 217 and the cap coupler 211 will compress cap spring 213 against the bottom of cap sheath 212 and lower head 218. As shown in FIG. 16E, head 218 can be lowered close to or in contact with the bottom of preprocessing chamber 440, which can be a stator 354, and head 218 can be rotated to disrupt tissue. When stepper motor 2110 raises, rotary motor 2120 and rotary motor coupler 2125 raise up and cap spring 213 decompresses to push cap coupler 211 against rotary motor coupler 2125 to continue engagement.

In another embodiment of the Single Sample Singulator Instrument 2050, stepper motor 2110 controls the vertical position of rotary motor 2120 which is magnetically coupled to moveable disruptor 345 with a magnetic or paramagnetic element embedded with cap 210 as part of cap coupler 211 or as part of moveable disruptor 345 or head 218.

When rotary motor coupler 2125 is engaged with cap coupler 211 by mechanical coupling, magnetic coupling, pneumatic, or fluidic coupling, or other coupling methods, and rotary motor 2120 rotates, moveable disruptor 325 and head 218 are rotated. Stepper motor 2110 controls the vertical position of the rotary motor 2120 and thereby the vertical position of rotary motor coupler 2125, to raise or lower moveable disruptor 345 and head 218 in preprocessing chamber 440. Combining rotation of rotary motor 2120 and movement of stepper motor 2110 enables many patterns of motion of moveable tissue disruptor 345 and head 218.

The inside walls of preprocessing chamber 440 can be embodied in many different shapes. The inside walls of preprocessing chamber 440 can be fluted to have sections with different depths. In a preferred embodiment, the inside wall can have a circular profile with the largest gap between the head 218 of moveable mechanical tissue disruptor 345 and the inside wall of preferrably greater than or equal to 1 µm, or 2 µm, or 5 µm, or 10 µm, or 15 µm, or 20 µm, or 25 µm, or 30 µm, or 40 µm, or 50 µm, or µm, or 100 µm, or 150 µm, or 200 µm, or 250 µm, or 500 µm, and 1000 µm or more, as well as any size in between.

Moveable tissue disruptor 345 can be embodied in many different shapes with many different profiles. In one embodiment, moveable tissue disruptor 345 can have a head 218 which is a rotor 353 with optional features, for example, grinding teeth 355 on the bottom of rotor 353 and grinding teeth 355 on stator 354 which is on the top surface of the bottom of the preprocessing chamber 440 to assist in disruption of large pieces of tissue specimens 120 into smaller pieces or assist in the dissociation into single cells 1000 or nuclei 1050 or biomolecules 1070. As shown in FIGS. 13 and 14, the sides of head 218 can be a cylinder to create an inside gap 221 with the inside wall over the length of the cylinder. By raising and lowering head 218 without turning head 218, thereby using it as a moveable disruptor 345, the system can process specimen 101 by trituration. In another embodiment the sides of the head 218 can form a ball-like structure to create a gap with the inside wall in a small area and the bottom of preprocessing chamber 440 can be rounded to match the ball-like structure to create a Dounce-like mechanical tissue disruptor 345. In other embodiments, multiple regions with gaps of the same or different sizes can be created by varying the side profile of moveable tissue disruptor 345 and the inner wall of preprocessing chamber 440.

Disruption of tissue can include a plurality of disruption steps, each involving positioning the head a different distance from floor of the chamber to produce gaps of different sizes. Typically, at each position, the head will rotate, further facilitating disruption or mixing. In certain embodiments, an organ can be auto-minced by the disrutor before tissue disruption into single cells 1000 or nuclei 1050 or other biological materials. Such a method can involve a first disruption step, which can include setting the head at a plurality of different distances from the floor of the chamber and rotating at each gap distance, to provide tissue with greater surface area and less distance for access by enzymes. A next step can involve incubating the auto-minced organ with enzymes or chemicals for tissue disruption into single cells 1000 or nuclei 1050. A next step can involve a second disruption step, which, in turn, can include setting the head at a plurality of different distances from the floor of the chamber and rotating the head.

Example: Production of a Single Cell Suspension from Fresh Mouse Kidney

The Single Sample Singulator System 2000 can be operated in many configurations. As an example, an operator may wish to process a fresh mouse kidney specimen 101 into a single cell suspension 1000 and use reagents stored on Reagent Module 1430. The operator would remove cap 210 from cartridge 200 as shown in FIG. 13A and add a whole mouse kidney, or a part of mouse kidney, or part of a kidney that had been preminced to sample inlet port 425. The cap 210, which is a moveable disruptor, is replaced on preprocessing chamber 440 with the bottom of cap sheath 212 seated on an annular seat in preprocessing chamber 440. The now complete cartridge with a tissue specimen is placed on cartridge receiver tray 1510 and inserted into the Single Sample Singulator instrument 2050 with cartridge slide 1450. After the appropriate protocol is selected through user interface 740 on tablet 750, the Single Sample Singulator instrument 2050 heats thermal transfer plate to hold the preprocessing chamber 440 at 37° C. and then begins processing kidney specimen 101.

After initialization of electronic boards, the z-axis stepper motor 2110 moves the rotary motor 2120 down to engage rotary motor coupler 2125 with cap coupler 211. The control software 725 then selects the proper valve settings to pull two mL of mouse kidney reagent solution from Position 3 in temperature-controlled reagent storage chamber 1419 of reagent module 1430, as shown in FIG. 17, and deliver it through port 470 to preprocessing chamber 440 where the mouse kidney has been placed.

If selected by the protocol, an auto-mince procedure to macerate the tissue is performed by the z-axis stepper motor 2110 moving rotary motor 2120, and therefore the mechanical tissue disruptor and head 218, which is functioning as a rotor 353, to 1.5 mm from the bottom of the preprocessing chamber 440 and then rotor 353 is rotated clockwise for four seconds and then counterclockwise for four seconds at 95 rpm. Rotor 353 is lowered to 0.6 mm from the bottom and rotated clockwise for four seconds and counterclockwise for four seconds at 95 rpm. Rotor 353 is lowered to 0.3 mm from the bottom and rotated clockwise for four seconds and counterclockwise for four seconds at 95 rpm to complete the standard automince portion of the protocol.

For mouse kidney, the now auto-minced kidney specimen 101 is then incubated for twenty minutes with continuous top immersion mixing where rotor 353 is lowered into the top third of the mouse kidney reagent solution with kidney specimen 101 in preprocessor chamber 440 and the rotary motor 210 spins rotor 353 clockwise at rpm in a continuous immersion mixing mode while the enzymatic formulation digests the extracellular matrix in the solid tissue to release cells.

After 20 min, the tissue is mechanically disrupted by lowering rotor 353 until it is 4.2 mm from the bottom, approximately 20% immersed into mouse kidney reagent solution with kidney specimen 101, and then the first mechanical disruption cycle is performed with rotor 353 rotating clockwise for four seconds and then rotating counterclockwise for four seconds at 95 rpm. The second disruption cycle is performed by lowering rotor 353 by 1.5 mm and rotating clockwise for four seconds and then counterclockwise for four seconds at 95 rpm. The third disruption cycle is by lowering rotor 353 by 0.9 mm and rotating clockwise for four seconds and counterclockwise for four seconds at 95 rpm. Then, the fourth and fifth disruptions cycles are performed with lowering rotor 353 by 0.6 mm each cycle with rotation clockwise for four seconds, counterclockwise for four seconds, then rotation clockwise for four seconds, and counterclockwise for four seconds at 95 rpm for each disruption cycle. For the sixth disruption cycle, the rotor 353 is raised 0.3 mm and then rotated clockwise for four seconds, counterclockwise for four seconds, clockwise for four seconds, and counterclockwise for four seconds at 95 rpm. For the seventh disruption cycle, the rotor 353 is lowered 0.6 mm and rotated clockwise for four seconds, counterclockwise for four seconds, rotated clockwise for four seconds, and counterclockwise for four seconds at 95 rpm. For the eight and final disruption cycle, the rotor 353 is lowered 0.3 mm in contact with the bottom surface of preprocessing chamber 440 and rotated clockwise for four seconds, counterclockwise for four seconds, rotated clockwise for four seconds, and counterclockwise for four seconds at 95 rpm. Many other possible disruption profiles are enabled by this instant invention.

The mechanical tissue disruption occurs at two places: first, at the bottom of rotor 353 by grinding teeth 355 and the top of stator 354 with complementary grinding teeth 355 to mechanically dissociate the solid tissue in bottom gap 222 and secondly, the gap between the circumference of the rotor 353 and the inner wall of preprocessing chamber 440 acts as an orifice to disrupt the tissue.

With the rotor 353 positioned at the bottom of preprocessing chamber 440, syringe pump 2130 then pulls vacuum through the appropriate six way valve settings on vacuum trap port 467 to pull the dissociated mouse kidney single cell suspension through line 453, through 70 μm strainer 2711 where it drains down strain drain 451 and into output collector region 461 in processing chamber 460.

The control software 725 sets the selection of valve settings to pull two mL of HBSS-Ca—Mg from Position 13 in room temperature reagent storage chamber 1418 of reagent module 1430 as shown in FIG. 17 and deliver it through port 470 to preprocessing chamber 440. Rotor 353 can be moved to mix any remaining dissociated cells with the HBSS-Ca—Mg and then with rotor 353 positioned at the bottom of preprocessing chamber 440, syringe pump 2130 then pulls vacuum through the appropriate six way valve settings on vacuum trap port 467 to pull the HBSS-Ca—Mg and any remaining dissociated mouse kidney single cells suspension through line 453, through 70 µm strainer 2711, down strain drain 451 and into output collector region 461 in processing chamber 460. This process is then repeated to deliver and pull a second two mL of HBSS-Ca—Mg through preprocessing chamber 440 and into processing chamber 460. The mouse kidney single cell 1000 suspension can then be pipetted out by opening processing chamber cap 465 and withdrawing the cell suspension from output collector region 461 using a pipettor.

The mouse kidney single cell 1000 suspension can be centrifuged at 300 g for five min to collect the cells as a pellet, the red blood cells lyzed for five min with a RBC lysis buffer, and the suspension centrifuged at 300 g for five min to collect the cells. As an example, a 262 mg of mouse kidney produced a single cell suspension 1000 by this process with a cell titer of 14,670,000 cells at a 85.5% viability as determined by counting on a Countess II with Trypan blue staining as shown in FIG. 18A.

Other tissues or organs may benefit from different modes of mixing. The Single Sample Singulator System 2000 is designed to perform a plurality of mixing modalities. For example, top mixing is designed to position the bottom of head 218 at mm above the bottom and rotate head 218 to mix the enzymatic or chemical dissolution solution 410 with the specimen 101. Shallow immersive mixing can be performed by continuously rotating head 218 as it is moved from 17.7 mm above the bottom down to 16.8 mm and back up again. Trituration mixing can be performed by moving head 218 without rotation from 12.3 mm above the bottom down to 0.3 mm above the bottom. Many other mixing modalities are enabled.

Example: Production a Single Nuclei Suspension from Flash Frozen Human Brain

The Single Sample Singulator System 2000 can be operated in many configurations to produce nuclei 1050 suspensions. As an example, an operator may wish to process a fresh mouse kidney specimen 101 into a single nuclei suspension 1050 and use reagents stored on Reagent Module 1430. The operator would remove cap 210 from cartridge 200 as shown in FIG. 13 and add a whole mouse kidney, or a part of a kidney, or part of a kidney that had been preminced to sample inlet port 425. The cap 210, which is a tissue disruptor, is replaced on preprocessing chamber 440 and the now complete cartridge with a tissue specimen 101 is placed on cartridge receiver tray 1510 and inserted into the Single Sample Singulator instrument 2050 with cartridge slide 1450. After the appropriate protocol is selected through user interface 740 on tablet 750, the Single Sample Singulator instrument 2050 cools thermal transfer plate 1470 to hold the preprocessing chamber 440 and processing chamber 460 at 4° C. and then begins processing kidney specimen 101. The thermal transfer plate 1470 can also be preheated or precooled as needed.

After initialization of boards, the z-axis stepper motor 2110 moves the rotary motor 210 down to engage rotary motor coupler 2125 with cap coupler 211. The control software 725 then selects the valve settings to pull two mL of nuclei isolation solution 412 from Position 1 in temperature-controlled reagent storage chamber 1419 of reagent module 1430 as shown in FIG. 17 and deliver it through port 470 to preprocessing chamber 440.

The tissue is then mechanically disrupted by lowering head 218 which will function as rotor 353 until it is 4.2 mm from the bottom, approximately 20% immersed into the nuclei isolation solution 412 with kidney specimen 101, and then the first mechanical disruption cycle is performed with moveable mechanical disruptor 345 and head 218 acting as a rotor 353 rotated clockwise for four seconds and then rotated counterclockwise for four seconds at 135 rpm. The second disruption cycle is by lowering rotor 353 by 1.5 mm and rotating clockwise for four seconds and then counterclockwise for four seconds at 135 rpm. The third disruption cycle is by lowering rotor 353 by 0.9 mm and rotating clockwise for four seconds and then rotating counterclockwise for four seconds at 135 rpm. Then, the fourth and fifth disruptions cycles are performed with lowering rotor 353 by 0.6 mm with rotation clockwise for four seconds, counterclockwise for four seconds, rotation clockwise for four seconds, and counterclockwise for four seconds at 135 rpm for each disruption cycle. For the sixth disruption cycle, the rotor 353 is raised 0.3 mm and then rotated clockwise for four seconds, counterclockwise for four seconds, clockwise for four seconds, and counterclockwise for four seconds at 135 rpm. For the seventh disruption cycle, the rotor 353 is lowered 0.6 mm and rotated clockwise for four seconds, counterclockwise for four seconds, rotated clockwise for four seconds, and counterclockwise for four seconds at 135 rpm. For the eighth disruption cycle, the rotor 353 is lowered 0.3 mm and rotated clockwise for four seconds, counterclockwise for four seconds, rotated clockwise for four seconds, and counterclockwise for four seconds at 135 rpm.

The mechanical tissue disruption again occurs both at the bottom of rotor 353 by grinding teeth 355 and the top of stator 354 with complementary grinding teeth 355 mechanically dissociating the solid tissue in bottom gap 222 as well as any tissue passing between the circumference of the rotor 353 and the inner wall of preprocessing chamber 440 in side gap 221.

With the rotor 353 positioned at the bottom of preprocessing chamber 440, syringe pump 2130 then pulls vacuum through the appropriate six way valve settings on vacuum trap port 467 to pull the dissociated mouse kidney nuclei suspension through line 453, through a 40 µm strainer 2711 in processing chamber 460, down strain drain 451 and into output collector region 461.

The control software 725 sets the selection of valve settings to pull two mL of nuclei storage solution 413 from Position 2 in temperature-controlled reagent storage chamber 1419 of reagent module 1430 as shown in FIG. 17 and delivers it through port 470 to preprocessing chamber 440. Rotor 353 can be moved to mix any remaining dissociated nuclei 1050 with the nuclei storage solution 413 and then with rotor 353 positioned at the bottom of preprocessing chamber 440, syringe pump 2130 pulls vacuum through the appropriate six way valve settings on vacuum trap port 467 to pull the nuclei storage solution 413 and any remaining dissociated mouse kidney single nuclei 1050 suspension through line 453, through a 40 µm strainer 2711, down strain drain 451 and into output collector region 461. The mouse kidney single nuclei 1050 suspension can then be pipetted out by opening processing chamber cap 465 and withdrawing the cell suspension from output collector region 461.

The mouse kidney single cell 1050 suspension can be centrifuged at 500 g for min to collect the cells as a pellet before resuspension in nuclei storage solution 413 or other media. As an example, a 108 mg mouse kidney produced by this process yielded a nuclei suspension 1050 with a titer of 24,225,000 as determined by counting on a Countess II with Trypan blue staining; a picture of the nuclei suspension 1050 is shown in FIG. 18B.

Example: Processing FFPE Tissue into Cells or Nuclei

FFPE tissue is commonly used by pathologists to examine biopsy samples. Massive banks of FFPE tissue contain archives of tissue samples from many disease states including cancers. Currently, isolating single cells or nuclei from FFPE is challenging and not automated.

In one embodiment, one or more thin sections from an FFPE block are added into cartridge 200, the cap 210 added, and the cartridge 200 placed into the Single Sample Singulator instrument 2050. In some embodiments cartridge 200 has a filter, such as a 25 µm filter added in or over the channel leading to preprocessing chamber nipple 471 to prevent loss of the undissociated FFPE thin section through the preprocessing chamber nipple 471.

After selection of the appropriate cell or nuclei FFPE protocol, and using the appropriate setup of reagent module 1430, the instrument can add, for example, 2 mL of xylol from the reagent module 1430 and incubate for a time period selected from the range of 10 sec, 30 sec, 1 min, 5 min, 10 min, 15 min, 30 min or longer at room temperature or other temperature. The xylol is then pulled into the processing chamber 460 as described and the process repeated two additional times with xylol. Xylene, histolene, and other compatible solvents can replace xylol. In some embodiments, the volume of processing chamber 460 is enlarged to accommodate the deparaffinization materials. In other embodiments, a separate waste chamber is added and pinch valves 491 are used to direct flow either to a waste chamber or processing chamber 460.

The instrument can then perform reverse sequential ethanol washes, for example, by adding two mL of 100% ethanol from the reagent module 1430 to cartridge 200 and incubating for a time period selected from the range of 10 sec, 30 sec, 1 min, 5 min, 10 min, 15 min, 30 min or longer at room temperature or other temperature. The 100% ethanol is then pulled into the processing chamber 460 as described and the process repeated none, one, or more additional times with 100% ethanol.

The instrument can add 2 mL of 70% ethanol from the reagent module 1430 to cartridge 200 and incubate for a time period selected from the range of 10 sec, 30 sec, 1 min, 5 min, 10 min, 15 min, 30 min or longer at room temperature or other temperature. The 70% ethanol is then pulled into the processing chamber 460 as described and the process repeated none, one, or more additional times with 70% ethanol.

The instrument can add 2 mL of 50% ethanol from the reagent module 1430 to cartridge 200 and incubate for a time period selected from the range of 10 sec, 30 sec, 1 min, 5 min, 10 min, 15 min, 30 min or longer at room temperature or other temperature. The 50% ethanol is then pulled into the processing chamber 460 as described and the process repeated none, one, or more additional times with 50% ethanol. In some embodiments, a 30% ethanol step or other additional reverse sequential ethanol wash steps can be added. In some embodiments, the ethanol washes and other solutions can be supplemented with PBS, bovine serum albumin, RNAse inhibitors, protease inhibitors, or other supplements.

The instrument can add 2 mL of purified water, such as double distilled water with RNAse inhibitors, from the reagent module to cartridge 200 and incubated for a time period selected from the range of 10 sec, 30 sec, 1 min, 5 min, 10 min, 15 min, 30 min, 60 min, 2 hours, 4 hours, 8 hours, 12 hours, 24 hours at at 4° C., room temperature or other temperatures. The water is then pulled into the processing chamber 460 as described and the process repeated none, one, or more additional times with purified water. The waste in processing chamber 460 can be removed at this time or previously as needed if it has not been directed to a waste chamber.

The deparaffinized FFPE can then be treated by different methods. In one method, an enzymatic digestion is performed by adding up to two mL of proteinase K solution (0.005% proteinase K, 30 U/mg protein, in 50 mM Tris hydroxymethyl aminomethane hydrochloride (pH 7.0), 10 mM EDTA, and 10 mM sodium chloride), with optional DNase addition, and incubating for a time period selected from the range of 1 min, 5 min, 10 min, 15 min, 30 min, 60 min, 2 hours, 4 hours, 8 hours, 12 hours, 24 hours at 37° C. or up to 60° C. or other temperatures.

If cells are to be produced, the proteinase K solution can be diluted by the addition of up to 2 mL of a solution to dissolve residual extracellular matrix such as adding formulations of a reagents or mixture of components comprised of but not limited to collagenases (e.g., collagenases type I, II, III, IV, and others), elastase, trypsin, papain, hyaluronidase, chymotrypsin, neutral protease, clostripain, caseinase, neutral protease (Dispose), DNAse, protease XIV, RNase inhibitors, or other enzymes, biochemicals, or chemicals such as EDTA, protease inhibitors, buffers, acids, or base. In one embodiment, two mL of an enzymatic cocktail containing 1 mg/ml of Collagenase/Dispase (Roche) and 100 units/ml of Hyaluronidase (Calbiochem) in PBS/0.5 mM $CaCl_2$) are added with optional DNase addition and incubated for a time period selected from the range of 1 min, 5 min, 10 min, 15 min, 30 min, 60 min, 2 hours, 4 hours, 8 hours, 12 hours, 24 hours at 37° C. or other temperatures. The released single cell 1000 suspension is then pulled into the processing chamber 460 through a µm filter as described and removed. The released cells are then centrifuged at 300 rpm for 5 minutes, and resuspended in buffer, such as PBS or HBSS, and optionally again filtered through a 70 µm or other filter. Additional processing can then be performed as appropriate for downstream procedures.

If nuclei are to be produced, 2 mL of nuclei isolation buffer 412, such as NST buffer (146 mM NaCl, 10 mM Tris base at pH 7.8, 1 mM $CaCl_2$), 21 mM $MgCl_2$, 0.05% BSA, 0.2% Nonidet P-40) can be added to the proteinase K solution and incubated for a time period selected from the range of 1 min, 5 min, 10 min, 15 min, 30 min, 60 min, 2 hours, 4 hours, 8 hours, 12 hours, or 24 hours. The released nuclei 1050 suspension is then pulled into the processing chamber 460 through a 40 µm or other filter as described and removed. The released nuclei are then centrifuged at 500 rpm for 5 minutes, and resuspended in nuclei storage buffer 413, and optionally again filtered through a 40 µm or other filter. Additional processing can then be performed as appropriate for downstream procedures.

Example Using a Vertical Cartridge in the Singulator System to Generate Microtissues or Organoids Another preferred embodiment of cartridge 200 is shown in FIGS. 19A and B. This vertical cartridge 200 is designed to be injection molded and then sealed with a material such as a heat sealable plastic laminate, or laser welded, or ultrasonically welded or other means to seal cartridge 200. It has two processing chambers 460 for processing samples which facilitates improved mixing during processing steps.

Referring to FIGS. 19A and B, a typical process flow is as follows. The operator inserts tissue specimen 120 into the preprocessing chamber 440 through sample inlet port 425 and places cap 210 (not shown) onto cartridge 200 and inserts cartridge 200 into the Singulator System 100, Tissue Processing System 80, or Sample Processing System 50 as described above. After selection of the appropriate program, the instrument makes the mechanical connection to cap 210 through rotary motor coupler 2125 (not shown) and fluid/gas connections to the fluid/gas inlets/outlets 480. The instrument also contacts the preprocessing chamber 440 and the two processing chambers 461 and 462 from the back of cartridge 200 with elements such as cartridge Peltier 1440 which can heat or cool said fluid chambers.

The appropriate enzymatic or chemical dissolution solution 410 is moved by fluidic subsystem 600 from reagent module 1430 into the preprocessing chamber 440 from fluid/gas inlets/outlets 480 through fluid channel 441. The solution may be heated or cooled by the action of the temperature regulating subsystem 1475 engaged with preprocessing chamber 440. The enzymatic or chemical dissolution solution 410 can contain enzymes or chemicals to help dissociate the tissue specimen 120 into a cell suspension 1000 or nuclei suspension 1050. The tissue disruptor in cap 410 acting as grinder rotor 420 is then mechanically rotated and brought up/down by the Singulator System 100 whereby tissue specimen 120 is separated into smaller and smaller pieces by the action of the grinding features on the head 218 which can be a grinder rotor 420 and grinder stator 421 on the bottom of preprocessing chamber 440. Single cell 1000 or nuclei suspension 1050 production is achieved by the combined action of the grinding elements and incubation/exposure of the tissue specimen 120 to reagents 411, e.g., enzymes, or chemicals, or combinations of enzymes and chemicals as described herein. After the tissue disruption is sufficiently advanced, the grinder rotor 420 can be brought completely down until it touches the grinder stator 421 whereby the singulated cells 1000 in the enzymatic dissolution solution 410 or nuclei suspension 1050 in chemical dissolution solution 414 are pushed around and above the grinder rotor 420 through the side gap 211 between the rotor and the wall of preprocessing chamber 440.

All the fluid/gas inlets/outlets 480 are then sealed by the syringe pump 2130 and appropriate valves and the singulated cells 1000 or nuclei 1050 suspension, or nucleic acids 1072 are pulled from the preprocessing chamber 440 through channel 442 to strain chamber 450 and then through channel 443 towards processing chamber 461 by applying negative pressure through channels 446 or 444. A filter in strain chamber 450 prevents undissociated tissue, cell aggregates, and large debris from entering processing chamber 461. Waste chamber 431 can containing a liquid absorbent or solid absorbent to prevent any liquid from exiting through the fluid/gas inlets/outlets 480 and into the Singulator System 100.

To generate microtissues 6001 or organoids 6002 from a single cell 1000 suspension, as shown in the closeup of FIG. 19 in FIG. 20, a nozzle 6100 at the end of channel 443 can be used to create hanging droplets 6200 which can generate microtissues 6001 or organoids 6002. This is achieved by control of the flow from strain chamber 450 to gently pull the single cell 1000 suspension until a droplet is formed on nozzle 6100. Processing chamber 461 can be prefilled with water or buffer with in some embodiments saturated with 5% $CO_2$ to provide hydration to hanging droplet 6200 to control evaporation. The temperature control of cartridge 200 by the instrument can incubate the microtissues 6001 or organoids 6002 at the desired temperature, for example, 37° C. The incubation can be for minutes, hours or days before harvesting of the microtissues 6001 or organoids 6002 by removing the seal on processing chamber 461, or cutting it open depending on cartridge design. In other embodiments, once the hanging droplet 6200 has formed microtissues 6001 or organoids 6002, the hanging droplet 6200 in processing chamber 461 can be released by pulling vacuum or pushing fluids through channel 442 and into channel 441. Once the microtissues 6001 or organoids 6002 are in processing chamber 461 the microtissues 6001 or organoids 6002 can be further grown by suppling sterile growth media through channel 444 or other channels.

If desired, the microtissues 6001 or organoids 6002 can be mixed with any added reagents by applying alternative negative (and or positive) pressure to channels 444 and 445 to move the sample back and forth from processing chamber 461 to processing chamber 462 through channel 448. If no further processing is desired, the operator can pull out the microtissues 6001 or organoids 6002 through an opening or processing chamber cap 465 (not shown) in the top wall of processing chamber 461 or processing chamber 462 or by removing the seal on the surface of the cartridge 200.

The microtissues 6001 or organoids 6002 can also be processed in vertical cartridge 200 by use of magnetic beads for the positive selection or depletion of specific cell types, such as stem cells, or for washing the cells and/or for exchanging the buffer. The microtissues 6001 or organoids 6002 can be further processed by using cell-specific affinity reagents coupled to magnetic beads. For example, cell-type specific affinity magnetic beads and reaction solutions are injected through channel 444 into processing chamber 461. The beads are incubated with the microtissues 6001 or organoids 6002 by mixing though channel 448 as described above, whereby the magnetic beads bind to their target cells. Then, magnet(s) 910 is/are applied to the frontside of processing chambers 462, whereby the magnetic beads (and attached microtissues 6001 or organoids 6002) are attracted to and held at the processing chamber 462 wall. The microtissues 6001 or organoids 6002 that does not contain the specific targets is pulled into the waste chamber 432 by applying negative pressure to through channels 447 and 449. Waste chamber 432 which can optionally contain a liquid or solid absorbent substance.

Simultaneously or subsequently, washing solution can be injected through channel 444 and pulled into chamber 462 by applying vacuum on channel 446 to wash the beads attached to magnet 910 by combinations of mixing, magnetic release/application and pulling liquid to the waste chamber 432 as described. This process can be repeated one or more times.

After the microtissues 6001 or organoids 6002 are in the desired output media, the magnet 910 is released, the cells homogeneously resuspended by mixing by moving the cells back and forth through channel 448, and then the microtissues 6001 or organoids 6002 is pulled either into processing chamber 461 or 462. The operator can then pull out the microtissues 6001 or organoids 6002 through an opening in the top wall of Processing Chamber 461 or 462 covered by a foil-seal, or septum, or processing chamber cap 465 or other mechanism (not shown). Other processing/reaction/fluidic elements can be added to the cartridge as desired to enable additional processing modes in including without limitation tangential flow filtration, optical interrogation, library preparation, and nucleic acid purification.

Similar processing methods can also be used to resuspend the microtissues 6001 or organoids 6002 in a specific media, buffer, or growth solution, such as Matricel, or to perform labeling with chemicals such as mass tags, or fluorescent dyes, or Raman labels, or other labels. In addition, similar methods can be used to chemically or biochemically modify single cells 1000 or nuclei 1050 or microtissues 6001 or organoids 6002 including screening of potential therapeutic compounds, or inhibitors of growth or viability. In some embodiments, Measurement Subsystem 500 can interrogate the microtissues 6001 or organoids 6002 inside cartridge 200.

In another embodiment, a single cell 1000 suspension is pulled directly into processing chamber 461 and stem cells purified by magnetic bead processing as described with non-stem cells removed. In another embodiment, a single cell 1000 suspension is pulled directly into processing chamber 461 and chemically induced into stem cells, or with transcription factors, or by retroviral-mediated expression of the four transcription factors Oct4, Sox2, cMyc, Klf4. Many other modalities are possible.

Example: Decreasing the Degradation of Biomolecules in Nuclei and Subcellular Components The degradation of RNA in nuclei during and after nuclei isolation can alter the amount and representation of RNA. The degradation is tissue specific and currently can prevent single nuclei sequencing of the transcriptome from tissues with high RNAse activity such as pancreas. Similarly, RNA or other biomolecules from other subcellular components such as nuclei and mitochondria can be degraded during isolation procedures. A method to improve the quality of RNA and other biomolecules comprised of proteins, lipids, polysaccharides, etc. isolated from solid tissue samples is described.

Current methods to dissociate solid tissues into nuclei, using reagents alone or in combination with mechanical disruption techniques, can result in RNA becoming severely degraded and therefore not useful for downstream genomic analyses. Current methods to preserve RNA quality include the use of high concentrations of RNAse inhibitors, performing operations at low temperature, and performing operations quickly. The action of RNAses on RNA within a nucleus are rapid enzymatic reactions. Addition of RNAse inhibitors that bind to RNAses can be ineffective for tissue types that exhibit high levels of RNAse activity. Performing operations at 4° C. can lower the rate of enzymatic activity, but again, if there are high levels of RNAses in the tissue sample, simply lowering the temperature, even in the presence of RNAse inhibitors, can fail to adequately protect RNA from degradation. Isolating nuclei from solid tissue samples in the 1-1000 mg range may also require total reagent volumes of 0.5 to 5 ml, and including RNAse inhibitor reagents at the typical one unit/microliter concentration can cost hundreds of dollars per sample.

This instant invention describes the use of additives to reduce the rate of degradation. In one method, proteinase K, a serine protease, or other proteases are added to degrade RNAses or DNases released from the extracellular matrix or upon lysis of cell membranes.

In another embodiment, reagents to increase the viscosity are added during the isolation of nuclei or other subcellular components, thereby reducing the rate of diffusion of DNases, RNAses, lipases, nucleases, proteases, and other degradatory enzymes, and therefore reducing the level of RNA degradation or other biomolecule degradation during the isolation procedure for nuclei, mitochondria or other subcellular components. Examples of such additives include, but aren't limited to, crowding agents, and biocompatible high molecular weight polymers comprised of ficoll, dextran, sucrose, trehalose, cellulose, and polyethylene glycol. Typical concentrations of such reagents used are approximately but not limited to 0.01% to 50% w/v.

A preferred embodiment of the method applied to isolating nuclei from solid tissues or previously prepared single cell suspensions is to include one or more of the additives in either a nuclei isolation solution 412, nuclei storage solution 413, or both as used to isolate nuclei from tissue samples. For example, when using the Singulator System 100 for isolating nuclei, the nuclei isolation solution 412 might have 5% w/v ficoll added or the nuclei storage solution 413 might have 5% w/v ficoll. One or both of these solutions might also contain one or more protease inhibitors, and one or more RNAse inhibitor reagents including but not limited to SUPERase• In RNase Inhibitor, RNaseOUT Recombinant Ribonuclease Inhibitor, RNAsecure RNase Inactivation Reagent, Recombinant RNase Inhibitor and small molecule reagents including, but not limited to nucleotides and inorganic phosphates.

A protocol for improved isolation of mouse kidney nuclei from 300 mg of fresh or flash frozen mouse kidney tissue might be comprised of:

1) Loading the nuclei isolation solution 412 and nuclei storage solution 413 with additives to increase viscosity onto the reagent module 1430.

2) Placing a fresh or flash frozen mouse kidney tissue specimen 120 in a cartridge 200 precooled at 4° C. and adding tissue disruptor cap 210.

3) Placing cartridge 200 in a Single Sample Singulator instrument 2050 set to 4° C. operating temperature.

4) Selecting the nuclei isolation protocol from the software user interface 740 and selecting "Run". The Singulator then delivers 2 mL of the nuclei isolation solution 412 to the mouse kidney tissue specimen 120 in the preprocessing chamber 440; mechanically disrupts the tissue at 135 rpm; pulls the sample through a 40 micron strainer into the processing chamber 460; adds 2 mL of the nuclei storage soluion 413 to preprocessing chamber 440 to rinse residual material and decrease the final detergent concentration to quench disruption; pulls the added nuclei storage solution 413 through the filter into the processing chamber 460.

5) The sample cartridge 200 is then removed from the Single Sample Singulator instrument 2050, the nuclei 1050 suspension pipetted into a 5 ml tube, and 2 mL of 4° C. nuclei storage buffer 413 added. The sample is then centrifuged at 4° C. for 5 minutes at 500 g. The supernatant is pipetted out and discarded. The nuclei pellet is then resuspended in one mL of nuclei storage buffer 413.

Example: Gene Expression Panels to Optimize the Performance of Dissociation Methods Disrupting intact tissue into single cells can induce transcriptional changes in the cells, through a process known as anoikis or other stress-response pathways. Such changes can lead to cell death or confound later genomic or proteomic analyses. Use of quantitative PCR (qPCR assays) on a panel of targeted genes known to be involved in anoikis or other cell-stress pathways can be used to characterize the dissociation-related transcriptional changes in the single cells produced by dissociation. The qPCR data can also be used to inform and optimize the dissociation process to reduce the stress-induced changes. While panels of genes have been described for monitoring specific cell stress pathways, none have been created to inform anoikis-induced stress or stress resulting from mechanical and/or enzymatic/chemical tissue disruption.

qPCR panels can be used to identify specific cell types or sub-cell types that are present in a mixture of dissociated cells or characterize individual cells that have been isolated. The cell identity information can in turn be used to inform and optimize the dissociation process for desired cell types.

The panel may also be used to characterize RNA isolated from nuclei as opposed to single cells. Processes for isolating nuclei can be much faster than for isolating cells. The shorter process time may reduce the amount of cell stress evident in the gene expression data. In addition, isolated nuclei will lack RNA from the cell cytoplasm and will therefore provide complementary data. The qPCR data can also be used to inform and optimize the dissociation process to reduce the stress-induced changes or to identify specific cell types of origin for nuclei.

The structure of an exemplary panel for cell stress shown in Table 1 is a collection of PCR primers chosen to amplify genes associated with cell stress, and that have been optimized to amplify RNA sequences rather than genomic DNA. The panels can consists of 1 to over 200 genes, and may include at least one housekeeping gene used as an internal control.

To use the panel, after isolation of cells from solid tissue using a device such as, but not limited to, the Singulator System 100, a user would perform RT-qPCR on a panel of genes involved in cell stress responses or cellular identity on a known number of cells, or nuclei, or known quantity of isolated RNA. The levels of gene expression would be determined and may be (1) compared to the level of expression of so-called housekeeping genes whose expression is not affected by cell stress responses, (2) compared to the level of gene expression obtained from cells isolated using a different isolation protocol, or (3) used to identify the presence or absence or specific cell types. Other analyses are also possible.

One example of a gene panel is shown below, with 38 genes suspected of being involved in cellular stress responses and two housekeeping genes used as internal controls. The genes have been chosen because they are broadly expressed in most tissues, enabling the panel to be used with cells derived from a variety of tissue samples. The panel shown in Table 1 was developed for use with mouse tissues. Genes marked with an asterix are the control housekeeping genes.

As an example, a user would disrupt a fresh mouse liver sample into a suspension of cells using the Singulator System 100 and a protocol for mouse liver. The user would then remove the cell suspension 1000 from the Singulator sample cartridge 200. After using a Countess, hemocytometer, FACS, or similar method to determine cell concentration, the user could employ a "Cells to Ct" kit (Invitrogen), or alternative method for performing cell lysis, cDNA synthesis and qPCR with the primer sets for the genes listed in the panel. Alternatively, the user could purify RNA from the isolated cells using an RNA isolation kit, e.g., RNA Easy kit (Qiagen), or alternatively, quantify the RNA concentration and purity, then perform a cDNA synthesis and qPCR experiment using the panel of genes. The qPCR amplification would be run on a Real Time PCR instrument with a thermal cycling profile appropriate to the kit or methods used. The qPCR experiment will return a cycle threshold (Ct) values for each gene and these data can be used to assess relative gene expression patterns.

Other assays for cell stress responses are available, including those based on measuring apoptosis or necrosis of cells. The panel defined in Table 1 is unique in that it represents genes that span several cell stress pathways, whether known or uncharacterized, and can be used to measure cell stress responses specifically to a tissue disruption process. It is designed to encompass an array of genes that may respond to tissue dissociation, which may trigger multiple stress pathways, rather than monitor one or a limited number of defined stress genes or pathways.

Example: Determining the Extent and Specificity of Gene Editing Methods

The use of CRISPR, TALENS, and other gene editing techniques are being increasingly used to experimentally manipulate biological systems for both research and clinical applications. Key metrics for the success or failure of such manipulations are the number of cells with effectively altered genomes and the specificity of such alterations at the desired locations as opposed to off-target editing. Off target gene editing can lead to disease-causing changes to cells. It is difficult to assess the penetrance of editing or the specificity through DNA or RNA sequencing of bulk tissue, as rare events may not be observable. It is important to perform an evaluation of gene editing using single cell sequencing techniques.

In this example, a biological test subject, such as but not limited to cell cultures, adherent cells, organoids, model organisms, or human patients has been treated with a gene editing process. Subsequent to the treatment, a sample or samples of cells or tissue is removed from the test organism or culture media. The sample, such as a tissue specimen 120 or microtissue 6001 or organoid 6002, is processed in the Singulator 100 or alternative device for tissue disruption to obtain a suspension of cells or nuclei. The cells or nuclei are then subjected to single cell or single nuclei DNA or RNA sequencing to determine the presence or absence of an edited genome and the representation within the single cell population.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The term "or" is, unless indicated otherwise, non-exclusive, i.e., encompassing both "and" and "or."

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present). Both plural and singular means may be included. The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

What is claimed is:

1. A system comprising:
   (a) an instrument comprising:
      (i) one or more cartridge interfaces, each configured to engage a cartridge and comprising one or more fluid ports;
      (ii) a fluidics subsystem comprising:
         (1) one or more sources of liquids and/or gasses;
         (2) one or more fluid lines communicating with the sources and with fluid ports in the cartridge interface; and
         (3) one or more pumps configured to move liquids and/or gasses from the sources into and/or out of the one or more fluid ports;
      (iii) a subsystem comprising an actuator to that engages and actuates a tissue disruptor in a cartridge engaged with a cartridge interface; and
   (b) one or more cartridges, each engaged with one of the cartridge interfaces, wherein at least one cartridge comprises:
      (i) one or more cartridge ports communicating with at least one of the fluid ports in the cartridge interface;
      (ii) a preprocessing chamber comprising a bottom surface and an opening and, positioned in the opening, a tissue disruptor configured for mechanical disruption of tissue, wherein the tissue disruptor comprises a plunger comprising a shaft and a head, wherein the plunger is configured to rotate and be raised or lowered within the preprocessing chamber, wherein the plunger comprises a coupler to engage the actuator,
   wherein the head (l) has a circumference which, when the head moves within the preprocessing chamber, provides a gap between the head and a wall of the preprocessing chamber between about 25 microns and 400 microns, and (II) comprises grinding teeth for disrupting tissue; and
      (iii) a processing chamber communicating with the preprocessing chamber, and with one or more cartridge ports and configured to collect a suspension of biological material from the preprocessing chamber.

2. The system of claim 1, wherein the instrument further comprises:
   one or a plurality of valves configured to direct positive or negative pressure from the one or more pumps through fluid lines and/or the one or more containers connecting the one or more fluid lines to the fluid ports.

3. The system of claim 1, wherein the instrument further comprises:
   a magnetic processing module comprising a source of a magnetic field, wherein the source is positioned to form a magnetic field in a processing chamber of an engaged cartridge.

4. The system of claim 1, wherein the instrument further comprises:
   a measurement subsystem.

5. The system of claim 1, wherein the instrument further comprises:
   a control subsystem comprising a processor and memory, wherein the memory comprises code that, when executed by the processor, operates the system.

6. The system of claim 1, wherein the instrument further comprises:
   a waste container communicating with the one or more pumps.

7. The system of claim 1, wherein the instrument further comprises:
   a temperature subsystem configured to regulate temperature in a chamber of the cartridge.

8. The system of claim 1, wherein the pump communicates through a fluid line with a fluid port in the cartridge interface that engages a cartridge port that communicates with the processing chamber, wherein vacuum applied through the fluid line pulls fluid from the preprocessing chamber into the processing chamber.

9. The system of claim 1, wherein each cartridge interface further comprises a reagent inlet port that communicates with a port in the preprocessing chamber configured to introduce reagent directly into the prepossessing chamber.

10. The system of claim 1, wherein the preprocessing chamber communicates with the processing chamber directly through a fluid line, or indirectly, through one or more fluid lines in the interface that communicate with ports in each of the preprocessing chamber and the processing chamber.

11. The system of claim 1, wherein the tissue disruptor comprises:
   (i) a sheath, and
   (ii) a bias mechanism that biases the plunger toward a retracted position, wherein actuation is required to actuate the plunger to a forward position.

12. The system of claim 11, wherein the plunger also can rotate around the longitudinal axis of the sheath.

13. The system of claim 11, wherein the plunger comprises a top side comprising a feature for engaging the actuator.

14. The system of claim 11, wherein the tissue disrupter head comprises an annular bevel, and the seat in the preprocessing chamber is configured to mate with the bevel such that when the plunger is actuated toward the bottom of the preprocessing chamber, there is a defined annular gap between the head and a wall of the preprocessing chamber, and no gap or a defined minimum gap between the disruption surface of the head and the bottom of the preprocessing chamber.

15. The system of claim 1, wherein the preprocessing chamber communicates with the processing chamber through a port in a side of the preprocessing chamber which is positioned above the bottom of the preprocessing chamber.

16. The system of claim 1, wherein the tissue disrupter is seated on a seat in the preprocessing chamber.

17. The system of claim 1, wherein the bottom surface comprises raised features for disrupting tissue.

18. The system of claim 1, wherein the preprocessing chamber communicates with the processing chamber through a fluidic channel connecting a port in a side of the preprocessing chamber with a port in a top of the processing chamber.

19. A method comprising:
(a) providing a system of claim 1, wherein the prepossessing chamber comprises a tissue sample;
(b) disrupting the tissue sample by using the actuator to actuate the tissue disrupter to produce a suspension of biological material; and
(c) using the fluidic subsystem to move the suspension of biological material from the preprocessing chamber into the processing chamber.

20. The method of claim 19, comprising lowering the head in the preprocessing chamber to push the suspension around and above the head through the gap between the head and a wall of the preprocessing chamber, and moving the suspension from the preprocessing chamber to the processing chamber through a port in a side of the preprocessing chamber.

21. The method of claim 19, wherein disrupting comprises positioning a disruption surface of the head a defined distance from a bottom surface of the preprocessing chamber and rotating the head to disrupt tissue in the preprocessing chamber.

22. The method of claim 19, wherein disrupting comprises positioning a disruption surface of the head with respect to a bottom surface of the preprocessing chamber at a plurality of different gap distances and, at each gap distance, rotating the head.

23. The method of claim 19, comprising:
disrupting tissue with the tissue disrupter;
incubating the disrupted tissue with at least one enzyme that digests extracellular matrix; and
disrupting the incubated tissue with the tissue disrupter.

24. The method of claim 19, wherein the fluidic subsystem applies a vacuum to a port communicating with the processing chamber to move the suspension of biological material.

25. The method of claim 19, wherein the cartridge further comprises a strainer and the suspension of biological material entering the processing chamber is strained to remove particulate matter.

26. The method of claim 19, wherein the tissue comprises a target cell and the method further comprises:
contacting the suspension of biological material in the processing chamber with solid particles comprising binding agents that bind to the target cells and sequester bound target cells within the suspension of biological material.

27. The method of claim 19, further comprising isolating nuclei from the suspension.

28. The method of claim 19, further comprising isolating cells from the suspension.

29. The system of claim 1, wherein the cartridge further comprises a strain chamber comprising a strainer fluidically positioned between the preprocessing chamber and the processing chamber.

30. The system of claim 1, wherein the actuator comprises a Z axis stepper motor and a rotary motor.

31. A cartridge comprising:
(i) a preprocessing chamber comprising:
(1) an opening and, positioned in the opening, a tissue disruptor configured for mechanical disruption of tissue, wherein the tissue disruptor comprises a plunger comprising a shaft and a head wherein the plunger is configured to rotate and be raised or lowered within the preprocessing chamber, and comprising a coupler to engage an actuator and a head for disrupting tissue,
wherein the head (1) has a circumference which when the head moves within the preprocessing chamber, provides a gap between the head and a wall of the preprocessing chamber between about 25 microns and 400 microns, and (II) comprises grinding teeth; and
(2) a preprocessing chamber port; and
(ii) a processing chamber comprising a processing chamber port communicating with the preprocessing chamber port through a fluid line, and
(iii) a cartridge port that communicates with the processing chamber, wherein a vacuum applied to the cartridge port pulls material from the preprocessing chamber into the processing chamber.

32. The cartridge of claim 31, wherein the tissue disruptor comprises:
(i) a sheath, and
(ii) a bias mechanism, that biases the plunger toward a retracted position, wherein actuation is required to actuate the plunger to a forward position.

33. The cartridge of claim 31, wherein the preprocessing chamber communicates with the processing chamber through a port in a side of the preprocessing chamber which is positioned above the bottom of the preprocessing chamber.

34. The cartridge of claim 31, wherein the bottom surface comprises raised features for disrupting tissue.

35. The cartridge of claim 31, wherein the cartridge further comprises a strain chamber comprising a strainer fluidically positioned between the preprocessing chamber and the processing chamber.

36. The cartridge of claim 31, wherein the actuator comprises a Z axis stepper motor and a rotary motor.

37. A method of creating a microtissue comprising:
(a) providing a cartridge comprising:
(i) a preprocessing chamber comprising an opening and, positioned in the opening, a tissue disruptor configured for mechanical disruption of tissue;
(ii) a strain chamber comprising a strainer, wherein the strain chamber communicates with the preprocessing chamber;
(iii) a first processing chamber communicating with the strain chamber, wherein the first processing chamber comprises an element configured to produce a hanging drop of liquid from the strain chamber;
(iv) an optional second processing chamber communicating with the first processing chamber;
(v) one or more cartridge ports communicating with the processing chamber and the second processing chamber if present;
and further comprising a tissue;
(b) disrupting the tissue with the tissue disruptor to produce a cell suspension;
(c) straining the cell suspension with the strainer to produce strained cell suspension; and
(d) forming a hanging drop from the strained cell suspension using the element.

38. The method of claim 37, comprising the second processing chamber.

39. The method of claim 37, wherein the element comprises a nozzle.

40. The method of claim 37, wherein the microtissue is an organoid.

41. The method of claim 37, wherein forming the hanging drop comprises pulling the cell suspension from the strain chamber until a droplet is formed on the element.

42. The method of claim 37, further comprising:
after forming the hanging drop, adding a liquid or gas to the processing chamber to support survival of the cells in the hanging drop.

* * * * *